US009023972B2

(12) United States Patent
Chu et al.

(10) Patent No.: US 9,023,972 B2
(45) Date of Patent: May 5, 2015

(54) POLYESTERS, METHODS OF MAKING POLYESTERS AND USES THEREFOR

(75) Inventors: Hunghao Chu, Cambridge, MA (US); Yadong Wang, Allison Park, PA (US); Zhengwei You, Shanghai (CN)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 4 days.

(21) Appl. No.: 13/522,996

(22) PCT Filed: Jan. 25, 2011

(86) PCT No.: PCT/US2011/022381
§ 371 (c)(1),
(2), (4) Date: Oct. 9, 2012

(87) PCT Pub. No.: WO2011/091411
PCT Pub. Date: Jul. 28, 2011

(65) Prior Publication Data
US 2013/0071930 A1 Mar. 21, 2013

Related U.S. Application Data

(60) Provisional application No. 61/298,052, filed on Jan. 25, 2010, provisional application No. 61/299,404, filed on Jan. 29, 2010.

(51) Int. Cl.
| | | |
|---|---|---|
| C08G 63/00 | (2006.01) | |
| A61K 47/34 | (2006.01) | |
| A61L 27/34 | (2006.01) | |
| A61L 27/54 | (2006.01) | |
| C08G 63/42 | (2006.01) | |
| C08F 2/00 | (2006.01) | |
| C08F 8/00 | (2006.01) | |
| C08F 8/14 | (2006.01) | |
| C08F 8/32 | (2006.01) | |
| C08F 8/40 | (2006.01) | |
| C08F 8/46 | (2006.01) | |
| C08F 222/10 | (2006.01) | |
| C08G 63/78 | (2006.01) | |
| C08G 63/91 | (2006.01) | |

(52) U.S. Cl.
CPC ............... *C08G 63/00* (2013.01); *A61K 47/34* (2013.01); *A61L 27/34* (2013.01); *A61L 27/54* (2013.01); *A61L 2300/258* (2013.01); *A61L 2300/406* (2013.01); *A61L 2300/41* (2013.01); *A61L 2300/416* (2013.01); *C08G 63/42* (2013.01); *C08F 2/00* (2013.01); *C08F 8/00* (2013.01); *C08F 8/14* (2013.01); *C08F 8/32* (2013.01); *C08F 8/40* (2013.01); *C08F 8/46* (2013.01); *C08F 222/10* (2013.01); *C08G 63/78* (2013.01); *C08G 63/91* (2013.01)

(58) Field of Classification Search
None
See application file for complete search history.

(56) References Cited

U.S. PATENT DOCUMENTS

| 3,925,319 | A | * | 12/1975 | Hiatt et al. ..................... 528/67 |
|---|---|---|---|---|
| 5,843,573 | A | | 12/1998 | Itoh et al. |
| 5,852,163 | A | | 12/1998 | Chen et al. |
| 5,962,621 | A | | 10/1999 | Beckerdite et al. |
| 6,074,758 | A | | 6/2000 | Barbee |
| 6,521,717 | B1 | | 2/2003 | Itoh |
| 7,538,178 | B2 | | 5/2009 | Sato et al. |
| 8,529,928 | B2 | * | 9/2013 | Wang et al. ................... 424/422 |
| 2003/0050432 | A1 | | 3/2003 | Ramesh et al. |
| 2006/0052510 | A1 | | 3/2006 | Haggman et al. |
| 2009/0297607 | A1 | | 12/2009 | Wang et al. |

FOREIGN PATENT DOCUMENTS

JP 2000265003 A 9/2000

OTHER PUBLICATIONS

Kim, Hon Sung et al; "Gene transferring efficiencies of novel diamino cationic lipids with varied hydrocarbon chains." . Bioconjugate Chem. (2004) 15 (5) p. 1095-1101.*
Kallinteri, Paraskevi et al; "Novel functionalized biodegradable polymers for nanoparticle drug delivery systems." Biomacromolecules (2005) 6 p. 1885-1894.*
Zern et al., Control Growth Factor Release Using a Self-Assembled [polycation:heparin] Complex, PLoS ONE, 2010, 1-7, 5-6.
Zern et al., A Biocompatible Arginine-Based Polycation, Advanced Functional Materials, 2010, 434-440, 21.
Zhang et al., Synthesis and characterization of poly(butylene succinate-co-butylene malate): a new biodegradable copolyester bearing hydroxyl pendant groups, Biomacromolecules, 2003, 437-445, 4.
Zimmermann, Polymers flex their muscles, Nature Materials, Dec. 2008, 932-933, 7.
Ifkovits et al., Review: photopolymerizable and degradable biomaterials for tissue engineering applications, Tissue Engineering, 2007, 2369-2385, 13-10.
Ingber, Mechanical signalling and the cellular response to extracellular matrix in angiogenesis and cardiovascular physiology, Circulation Research, 2002, 877-887, 91.
Jerome et al., Recent advances in the synthesis of aliphatic polyesters by ring-opening polymerization, Advanced Drug Delivery Reviews, 2008, 1056-1076, 60.
Jiao et al., Surface modification of polyester biomaterials for tissue engineering, Biomedical Materials, 2007, R24-R37, 2.
Kallinteri et al., Novel functionalized biodegradable polymers for nanoparticle drug delivery systems, Biomacromolecules, 2005, 1885-1894, 6.

(Continued)

*Primary Examiner* — Maury Audet
*Assistant Examiner* — Fred Reynolds
(74) *Attorney, Agent, or Firm* — The Webb Law Firm

(57) ABSTRACT

Polyester compositions and functionalized polyester compositions are provided along with methods of making the compositions as well as methods of using the compositions, for example as a tissue engineering bioscaffold and as a drug-delivery vehicle.

59 Claims, 44 Drawing Sheets

(56) References Cited

OTHER PUBLICATIONS

Kaneko et al., Environmentally degradable, high-performance thermoplastics from phenolic phytomonomers, Nature Materials, Dec. 2006, 966-970, 5.
Kano et al., VEGF-A and FGF-2 synergistically promote neoangiogenesis through enhancement of endogenous PDGF-B-PDGFRβ signaling, Journal of Cell Science, 2005, 3759-3768, 118.
Kasper et al., Synthesis of poly(propylene fumarate), Nature Protocols, 2009, 518-525, 4-4.
Kawai et al., In vitro apatite formation on polyamide containing carboxyl groups modified with silanol groups, J Mater Sci: Mater Med, 2007, 1037-1042, 18.
Kester et al., Glycidyl esters of aliphatic acids, J Org Chem, 1943, 550-556, 8-6.
Kim et al., Gradient polymer surfaces for biomedical applications, Progress in Polymer Science, 2008, 138-164, 33.
Klim et al., A defined glycosaminoglycan-binding substratum for human pluripotent stem cells, Nature Methods, Dec. 2010, 1-8, 7-12.
Kline et al., One-step biocatalytic synthesis of linear polyesters with pendant hydroxyl groups, J. Am. Chem. Soc., 1998, 9475-9480, 120.
Kramer et al., Polymerization of Enantiopure Monomers Using Syndiospecific Catalysts: A New Approach to Sequence Control in Polymer Synthesis, J. Am. Chem. Soc., 2009, 16042-16044, 131.
Kreuger et al., Interactions between heparan sulfate and proteins: the concept of specificity, Journal of Cell Biology, Jul. 31, 2006, 323-327, 174-3.
Kumar et al., Versatile route to polyol polyesters by lipase catalysis, Macromolecules, 2003, 8219-8221, 36.
Kumar et al., Polarization of hydroxyapatite: influence on osteoblast cell proliferation, Acta Biomaterialia, 2010, 1549-1554, 6.
Kwon et al., Polymeric micelles as new drug carriers, Advanced Drug Delivery Reviews, 1996, 107-116, 21.
Laham et al., Local perivascular delivery of basic fibroblast growth factor in patients undergoing coronary bypass surgery: results of a phase I randomized, double-blind, placebo-controlled trial, Circulation, 1999, 1865-1871, 100.
Lambiase et al., Experimental and clinical evidence of neuroprotection by nerve growth factor eye drops: Implications for glaucoma, PNAS, Aug. 11, 2009, 13469-13474, 106-32.
Langer et al., Tissue engineering, Science, May 14, 1993, 920-926, 260.
Langer et al., Designing materials for biology and medicine, Nature, Apr. 1, 2004, 487-492, 428.
Lecomte et al., New prospects for the grafting of functional groups onto aliphatic polyesters. Ring-opening polymerization of α- or γ-substituted ε-caprolactone followed by chemical derivatization of the substituents, Macromol. Symp., 2006, 157-165, 240.
Lee et al., Strain Rate Effects on Tensile Failure Properties of the Common Carotid Artery and Jugular Veins of Ferrets, J. Biomechanics, 1992, 925-927, 25-8.
Leemhuis et al., Functionalized poly(α-hydroxy acid)s via ring-opening polymerization: Toward hydrophilic polyesters with pendant hydroxyl groups, Macromolecules, 2006, 3500-3508, 39.
Lendlein et al., Biodegradable, Elastic Shape-Memory Polymers for Potential Biomedical Applications, Science, May 31, 2002, 1673-1676, 296.
Lendlein et al., Light-induced shape-memory polymers, Nature, Apr. 14, 2005, 879-882, 434.
Lindahl et al., Pericyte loss and microaneurysm formation in PDGF-B-deficient mice, Science, Jul. 11, 1997, 242-245, 277.
Liu et al., Preparation and Characterization of a Biodegradable Polyester Elastomer with Thermal Processing Abilities, Journal of Applied Polymer Science, 2005, 2033-2041, 98.
Liu et al., Review of progress in shape-memory polymers, Journal of Materials Chemistry, 2007, 1543-1558, 17.
Liu et al., Structure and Properties of Thermoplastic Poly(glycerol sebacate) Elastomers Originating from Prepolymers Different Molecular Weights, Journal of Applied Polymer Science, 2007, 1131-1137, 104.
Liu et al., Study on the control of the compositions and properties of a biodegradable polyester elastomer, Biomedical Materials, 2009, 025015 (9 pages), 4.
Lutolf et al., Repair of bone defects using synthetic mimetics of collagenous extracellular matrices, Nature Biotechnology, May 2003, 513-518, 21.
Lutz et al., A controlled sequence of events, Nature Chemistry, Feb. 2010, 84-85, 2.
Macri et al., Growth factor binding to the pericellular matrix and its importance in tissue engineering, Advanced Drug Delivery Reviews, 2007, 1366-1381, 59.
Maerker et al., Glycidyl Esters. I. Method of Preparation and Study of Some Reaction Variables, J. Org. Chem., Aug. 1961, 2681-2688, 26.
Marklein et al., Controlling Stem Cell Fate with Material Design, Advanced Materials, 2010, 175-189, 22.
Mather et al., Shape Memory Polymer Research, Annual Review of Materials Research, 2009, 445-471, 39.
Matyjaszewski et al., Nanostructured functional materials prepared by atom transfer radical polymerization, Nature Chemistry, Jul. 2009, 276-288, 1.
Migneco et al., Poly(glycerol-dodecanoate), a biodegradable polyester for medical devices and tissue engineering scaffolds, Biomaterials, 2009, 6479-6484, 30.
Millette et al., Platelet-derived growth factor-BB-Induced human smooth muscle cell proliferation depends on basic FGF release and FGFR-1 activation, Circulation Research, 2005, 172-179, 96.
Miyazaki et al., Apatite deposition on polyamide films containing carboxyl group in a biomimetic solution, Journal of Materials Science: Materials in Medicine, 2003, 569-574, 14.
Motlagh et al., Hemocompatibility evaluation of poly(glycerol-sebacate) in vitro for vascular tissue engineering, 2006, 4315-4324, 27.
Moy et al., Properly oriented heparin-decasaccharide-induced dimers are the biologically active form of basic fibroblast growth factor, Biochemistry, 1997, 4782-4791, 36.
Nair et al., Biodegradable polymers as biomaterials, Progress in Polymer Science, 2007, 762-798, 32.
Nakaoka et al., Effects of surface chemistry prepared by self-assembled monolayers on osteoblast behavior, J Biomed Mater Res Part A, 2010, 524-532, 94A.
Neeley et al., A microfabricated scaffold for retinal progenitor cell grafting, Biomaterials. 2008, 418-426, 29.
Nehls et al., Heterogeneity of microvascular pericytes for smooth muscle type alpha-actin, The Journal of Cell Biology, Apr. 1991, 147-154, 113-1.
Nijst et al., Synthesis and Characterization of photocurable elastomers from poly(glycerol-co-sebacate), Biomacromolecules, 2007, 3067-3073, 8.
Albertsson et al., Aliphatic Polyesters: Synthesis, Properties and Applications, 2002, 1-40, 157.
Aviezer et al., Differential structural requirements of heparin and heparin sulfate proteoglycans that promote binding of basic fibroblast growth factor to its receptor, The Journal of Biological Chemistry, Jan. 7, 1994, 114-121, 269-1.
Barrett et al., Design and applications of biodegradable polyester tissue scaffolds based on endogenous monomers found in human metabolism, Molecules, 2009, 4022-4050, 14.
Benoit et al., Small functional groups for controlled differentiation of hydrogel-encapsulated human mesenchymal stem cells, Nature Materials, Oct. 2008, 816-823, 7.
Borselli et al., Functional muscle regeneration with combined delivery of angiogenesis and myogenesis factors, PNAS Early Edition, 2010, 1-6, 107-8.
Bruggeman et al., Biodegradable Xylitol-Based Polymers, Advanced Materials, 2008, 1922-1927, 20.
Bueno et al., Cell-free and cell-based approaches for bone regeneration, Nature Reviews Rheumatology, Dec. 2009, 685-697, 5.
Cao et al., Angiogenic synergism, vascular stability and improvement of hind-limb ischemia by a combination of PDGF-BB and FGF-2, Nature Medicine, May 2003, 604-613, 9-5.
Cao et al., Spatiotemporal control over growth factor signaling for therapeutic neovascularization, Advanced Drug Delivery Reviews, Nov. 10, 2007, 1340-1350, 59-13.

(56) References Cited

OTHER PUBLICATIONS

Capila et al., Heparin—Protein interactions, Angew. Chem. Int. Ed., 2002, 390-412, 41.

Chen et al., Characterisation of a soft elastomer poly(glycerol sebacate) designed to match the mechanical properties of myocardial tissue, Biomaterials, 2008, 47-57, 29.

Chen et al., Release characteristics and bioactivity of gelatin-tricalcium phosphate membranes covalently immobilized with nerve growth factors, Biomaterials, 2005, 6579-6587, 26.

Chen et al., Ultra-low fouling peptide surfaces derived from natural amino acids, Biomaterials, 2009, 5892-5896, 30.

Chen et al., Versatile Synthesis of Functional Biodegradable Polymers by Combining Ring-Opening Polymerization and Postpolymerization Modification via Michael-Type Addition Reaction, Macromolecules, 2010, 201-207, 43.

Chu et al., A [polycation:heparin] complex releases growth factors with enhanced bioactivity, Journal of Controlled Release, 2011, 157-163, 150.

Chu et al., Design, synthesis and biocompatibility of an arginine-based polyester, Biotechnol. Prog., 2012, 257-264, 28.

Cross et al., FGF and VEGF function in angiogenesis: signalling pathways, biological responses and therapeutic inhibition, TRENDS in Pharmacological Sciences, Apr. 2001, 201-207, 22-4.

Cukierman et al., Taking cell-matrix adhesions to the third dimension, Science, Nov. 23, 2001, 1708-1712, 294.

Dado et al., Cell-scaffold mechanical interplay within engineered tissue, Seminars in Cell & Developmental Biology, 2009, 656-664, 20.

Deblois et al., Heparin-fibroblast growth factorfibrin complex: in vitro and in vivo applications to collagen-based materials, Biomaterials, 1994, 665-672, 15-9.

De Jong et al., Dimethylmethylene blue-based spectrophotometry of glycosaminoglycans in untreated urine: a rapid screening procedure for mucopolysaccharidoses, Clinical Chemistry, 1989, 1472-1477, 35-7.

Deng et al., RGD peptide grafted biodegradable amphiphilic triblock copolymer poly(glutamic acid)-b-poly(L-lactide)-b-poly(glutamic acid): Synthesis and self-assembly, J Polym Sci Part A: Polym Chem, 2007, 3218-3230, 45.

Discher et al., Tussue cells feel and respond to the stiffness of their substrate, Science, Nov. 18, 2005, 1139-1143, 310.

Dityatev et al., Compartmentalization from the outside: the extracellular matrix and functional microdomains in the brain, Trends in Neuroscience, Nov. 2010, 503-512, 33-11.

Fischer et al., In vitro cytotoxicity testing of polycations: influence of polymer structure on cell viability and hemolysis, Biomaterials, 2003, 1121-1131, 24.

Gallagher et al., Heparin-sulfate in the binding and activation of basix fibroblast growth-factor, Glycobiology, 1992, 523-528, 2-6.

Gao et al., Co-expression of elastin and collagen leads to highly compliant engineered blood vessels, J Biomed Mater Res, 2008, 1120-1128, 85A.

Gao et al., Macroporous elastomeric scaffolds with extensive micropores for soft tissue engineering, Tissue Engineering., 2006, 917-925, 12-4.

Gerhardt et al., Functional lactide monomers: methodology and polymerization, Biomacromolecules, Jun. 2006, 1735-1742, 7-6.

Ghosh et al., Micromechanical control of cell and tissue development: implications for tissue engineering, Advanced Drug Delivery Reviews, 2007, 1306-1318, 59.

Gill et al., Direct brain infusion of glial cell line-derived neurotrophic factor in Parkinson disease, Nature Medicine, May 2003, 589-595, 9-5.

Gorsi et al., Tinkering with heparan sulfate sulfation to steer development, Trends in Cell Biology, 2007, 173-177, 17-4.

Gosline et al., Elastic proteins: biological roles and mechanical properties, Phil. Trans. R. Soc. Lond. B, 2002, 121-132, 357.

Gotte et al., Heparanase, hyaluronan, and CD44 in cancers: A breast carcinoma perspective, Cancer Res, Nov. 1, 2006, 10233-10237, 66-21.

Gumera et al., Modulating neuronal responses by controlled integration of acetylcholine-like functionalities in biomimetic polymers, Advanced Materials, 2007, 4404-4409, 19.

Gumera, New materials and scaffold fabrication method for nerve tissue engineering, Dissertation Presented to the Academic Faculty, Georgia Institute of Technology, May 2009, 1-162.

Gumera et al., Materials for central nervous system regeneration: bioactive cues, Journal of Materials Chemistry, 2011, 7033-7051, 21.

Gupta et al., Human studies of angiogenic gene therapy, Circ Res, Oct. 9, 2009, 724-736, 105-8.

Hacker et al., Heparan sulphate proteoglycans: The sweet side of development, Nature Reviews Molecular Cell Biology, Jul. 2005, 530-541, 6.

Hanson et al., A blue spectral shift of the hemoglobin Soret band correlates with the age (time since deposition) of dried bloodstains, PLoS ONE, Sep. 2010, 1-11, 5-9.

Hao et al., New facile approach to novel water-soluble aliphatic poly(butylene tartarate)s bearing reactive hydroxyl pendant groups, Biomacromolecules, 2005, 3474-3480, 6.

Hench et al., Third-generation biomedical materials, Science, Feb. 8, 2002, 1014-1017, 295.

Henry et al., The VIVA Trial Vascular endothelial growth factor in ischemia for vascular angiogenesis, Circulation, 2003, 1359-1365, 107.

Hersel et al., RGD modified polymers: biomaterials for stimulated cell adhesion and beyond, Biomaterials, 2003, 4385-4415, 24.

Hoogenboom et al., Microwave-assisted polymer synthesis: recent developments in a rapidly expanding field of research, Macromolecular Rapid Communications, 2007, 368-386, 28.

Hori et al., Controlled-release of epidermal growth factor from cationized gelatin hydrogel enhances corneal epithelial wound healing, Journal of Controlled Release, 2007, 169-176, 118.

Hsieh et al., Controlled delivery of PDGF-BB for myocardial protection using injectable self-assembling peptide nanofibers, The Journal of Clinical Investigation, 2006, 237-248, 116-1.

Huebsch et al., Harnessing traction-mediated manipulation of the cell/matrix interface to control stem-cell fate, Nature Materials, Jun. 2010, 518-526, 9.

Nilasaroya et al., Structural and functional characterisation of poly(vinyl alcohol) and heparin hydrogels, Biomaterials, 2008, 4658-4664, 29.

Nishikubo et al., Addition reactions of cyclic ethers with various carbonyl compounds and their application for polymer synthesis, Prog. Polym. Sci., 1993, 963-995, 18.

Noga et al., Synthesis and modification of functional poly(lactide) copolymers: toward biofunctional materials, Biomacromolecules, 2008, 2056-2062, 9.

Pang et al., Review of conventional and novel polymerization processes for polyesters, Progress in Polymer Science, 2006, 1009-1037, 31.

Park et al., Vascular endothelial growth-factor (VEGF) isoforms: differential deposition into the subepithelial extracellular-matrix and bioactivity of extracellular matrix-bound VEGF, Molecular Biology of the Cell, Dec. 1993, 1317-1326, 4.

Parrish et al., Strategies in Aliphatic Polyester Synthesis for Biomaterial and Drug Delivery Applications, ACS Symposium Series, American Chemical Society, Degradable Polymers and Materials, 2006, 248-266.

Patel et al., Dual delivery of an angiogenic and an osteogenic growth factor for bone regeneration in a critical size defect model, Bone, 2008, 931-940, 43.

Phadke et al., Templated Mineralization of Synthetic Hydrogels for Bone-Like Composite Materials: Role of Matrix Hydrophobicity, Biomacromolecules, 2010, 2060-2068, 11.

Ponsart et al., A novel route to poly($\epsilon$-caprolactone)-based copolymers via anionic derivatization, Biomacromolecules, 2000, 275-281, 1.

Radisic et al., Biomimetic approach to cardiac tissue engineering: oxygen carriers and channeled scaffolds, Tissue Engineering, 2006, 2077-2091, 12-8.

Rajangam et al,. Heparin binding nanostructures to promote growth of blood vessels, Nano Letters, 2006, 2086-2090, 6-9.

(56) References Cited

OTHER PUBLICATIONS

Raman et al., Structural insights into biological roles of protein-glycosaminoglycan interactions, Chemistry & Biology, Mar. 2005, 267-277, 12.

Redenti et al., Engineering retinal progenitor cell and scrollable poly(glycerol-sebacate) composites for expansion and subretinal transplantation, Biomaterials, 2009, 3405-3414, 30.

Saif et al., Combination of Injectable Multiple Growth Factor-Releasing Scaffolds and Cell Therapy as an Advanced Modality to Enhance Tissue Neovascularization, Arterioscler Thromb Vasc Biol, 2010, 1897-1904, 30.

Sakiyama-Elbert et al., Controlled release of nerve growth factor from a heparin-containing fibrin-based cell ingrowth matrix, Journal of Controlled Release, 2000, 149-158, 69.

Saksela et al., Endothelial cell-derived heparansulfate binds basic fibroblast growth factor and protect it from proteolytic degradation, The Journal of Cell Biology, Aug. 1988, 743-751, 107.

Sales et al., Protein precoating of elastomeric Tissue-Engineering Scaffolds Increased Cellularity, Enhanced extracellular matrix protein production, and differentially regulated the phenotypes of circulating endothelial progenitor cells, Circulation, 2007, I55-I63, 116-suppl I.

Sarkar et al., Adenoviral transfer of HIF-1α enhances vascular responses to critical limb ischemia in diabetic mice, PNAS, Nov. 3, 2009, 18769-18774, 106-44.

Seal et al., Physical polymer matrices based on affinity interactions between peptides and polysaccharides, Biomacromolecules, 2003, 1572-1582, 4.

Sellke et al., Vascular growth factors and angiogenesis in cardiac surgery, The Annals of Thoracic Surgery, 2003, 685-690, 75.

Shi et al., Photo-cross-linking and cleavage induced reversible size change of bio-based nanoparticles, Macromolecules, 2008, 8167-8172, 41.

Sirko et al., Chondroitin sulfate glycosaminoglycans control proliferation, radial glia cell differentiation and neurogenesis in neural stem/progenitor cells, Development, 2007, 2727-2738, 134.

Sokolowski et al., Medical applications of shape memory polymers, Biomedical Materials, 2007, S23-S27, 2.

Stayshich et al., New insights into poly(lactic-co-glycolic acid) microstructure: Using repeating sequence copolymers to decipher complex NMR and thermal behavior, J. Am. Chem. Soc., 2010, 10920-10934, 132.

Studer et al., Amino end-functionalized poly(ethylene oxide)-block-poly(methylidene malonate 2.1.2) block copolymers: synthesis, characterization, and chemical modification for targeting purposes, European Polymer Journal, 2008, 1714-1721, 44.

Tae et al., PEG-cross-linked heparin is an affinity hydrogel for sustained release of vascular endothelial growth factor, J. Biomater. Sci. Polymer Edn, 2006, 187-197, 17-1-2.

Taipale et al., Growth factors in the extracellular matrix, FASEB J., 1997, 51-59, 11.

Tanaka et al., Solvent-free organic synthesis, Chem. Rev., 2000, 1025-1074, 100.

Tang et al., Biomaterials from sugars: ring-opening polymerization of a carbohydrate lactone, Chem. Commun., 2009, 941-943.

Taniguchi et al., Functional modification of biodegradable polyesters through a chemoselective approach: application to biomaterial surfaces, Polymer International, 2006, 1385-1397, 55.

Tayalia et al., Controlled Growth Factor Delivery for Tissue Engineering, Advanced Materials, 2009, 3269-3285, 21.

Thomas et al., Stereocontrolled ring-opening polymerization of cyclic esters: synthesis of new polyester microstructures, Chem. Soc. Rev., 2010, 165-173, 39.

Toole, Hyaluronan: From extracellular glue to pericellular cue, Nature Reviews Cancer, Jul. 2004, 528-539, 4.

Uebersax et al., Biopolymer-Based Growth Factor Delivery for Tissue Repair: From Natural Concepts to Engineered Systems, Tissue Engineering: Part B, 2009, 263-289, 15-3.

Van Der Ende et al., Approach to formation of multifunctional polyester particles in controller nanoscopic dimensions, J. Am. Chem. Soc., 2008, 8706-8713, 130.

Van Royen et al., A critical review of clinical arteriogenesis research, Journal of the American College of Cardiology, 2010, 17-25, 55-1.

Vasita et al., Improved biomaterials for Tissue engineering applications: surface modification of polymers, Current Topics in Medical Chemistry, 2008, 341-353, 8.

Vert, Aliphatic polyesters: great degradable polymers that cannot do everything, Biomacromolecules, 2005, 538-546, 6.

Wang et al., The roles of matrix polymer crystallinity and hydroxyapatite nanoparticles in modulating material properties of photo-crosslinked composites and bone marrow stromal cell responses, Biomaterials, 2009, 3359-3370, 30.

Wang et al., A tough biodegradable elastomer, Nature Biotechnology, Jun. 2002, 602-606, 20.

Wang et al., In vivo degradation characteristics of poly(glycerol sebacate), J Biomed Mater Res, 2003, 192-197, 66A.

Wang et al., Silk coatings on PLGA and alginate microspheres for protein delivery, Biomaterials, 2007, 4161-4169, 28.

Whitelock et al., Diverse Cell Signaling Events Modulated by Perlecan, Biochemistry, 2008, 11174-11183, 47.

Whitelock et al., The degradation of human endothelial cell-derived perlecan and release of bound basic fibroblast growth factor by stromelysin, collagenase, plasmin, and heparanases, Journal of Biological Chemistry, Apr. 26, 1996, 10079-10086, 271-17.

Williams, Synthesis of functionalized biodegradable polyesters, Chem. Soc. Rev., 2007, 1573-1580, 36.

Williams, Strategies for Biodegradeable, Resorbable Polymers, European Medical Device Technology, Apr. 1, 2010, 1-4.

Winkler et al., [2+2] Photocycloaddition/fragmentation strategies for the synthesis of natural and unnatural products, Chem. Rev., 1995, 2003-2020, 95.

Yang, et al. Novel Citric Acid-Based Biodegradable Elastomers for Tissue Engineering, Advanced Materials, Mar. 18, 2004, 511-516, 16-6.

You et al., A functionalizable polyester with free hydroxyl groups and tunable physiochemical and biological properties, Biomaterials, 2010, 3129-3138, 31.

Younes et al., Synthesis, characterization and in vitro degradation of a biodegradable elastomer, Biomaterials, 2004, 5261-5269, 25.

Jain, Molecular regulation of vessel maturation, Nature Medicine, Jun. 2003, 685-693, vol. 4, No. 6.

Akabori, et al., The Novel Syntheses of Photoreversible Cyclobutanocrown Ethers by the Intramolecular Photoaddition of a w-Dicinnamoyl Polyethylene Blycol Derivatives, The Chemical Society of Japan, Sep. 1987, 3453-3455, vol. 60.

Akabori, et al., The Preparation of Photoresponsive Cyclobutanocrown Ethers by Means of Intramolecular [2+2] Photocycloaddition, The Chemical Society of Japan, Jul. 1988, 2459-2466, vol. 61.

\* cited by examiner

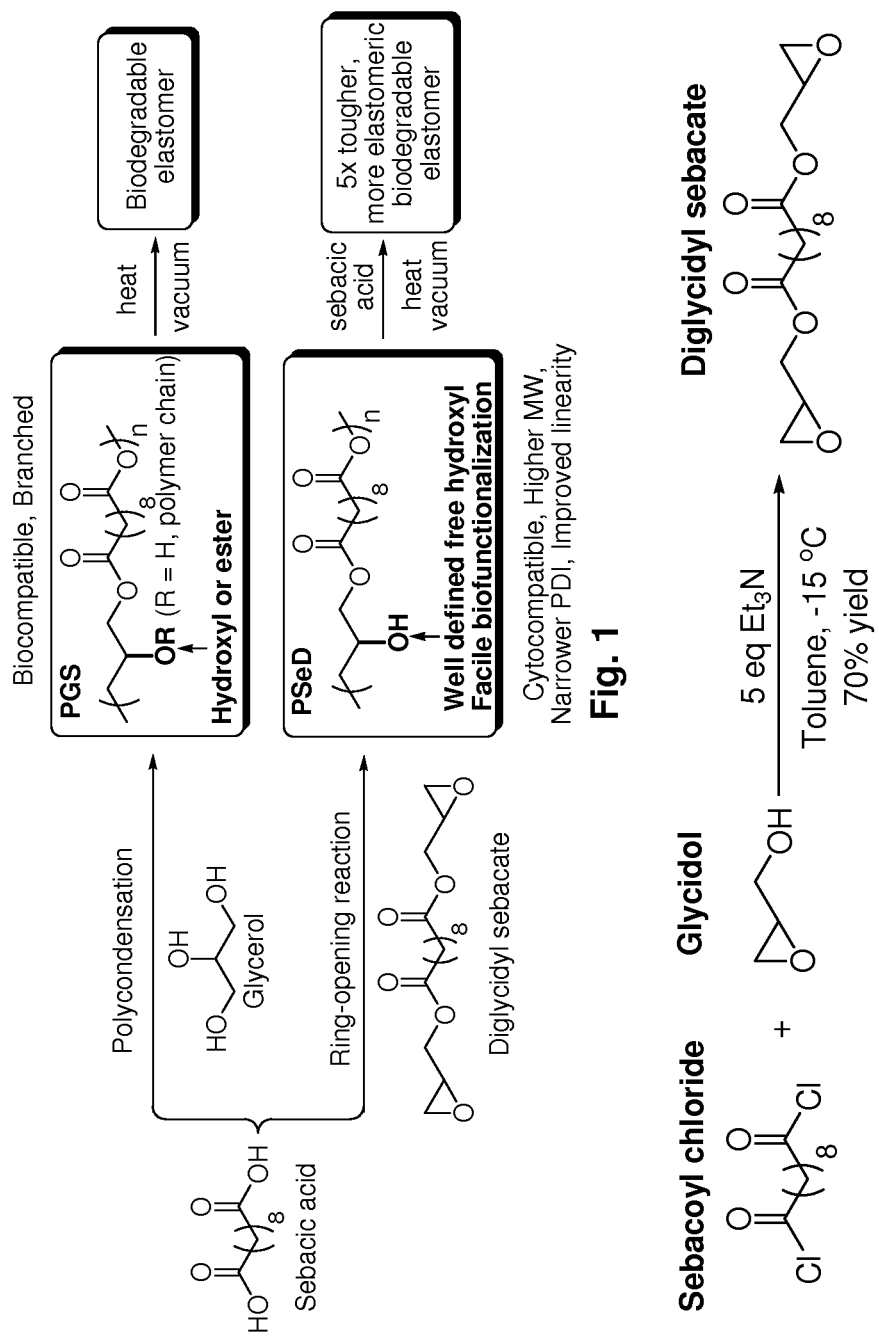

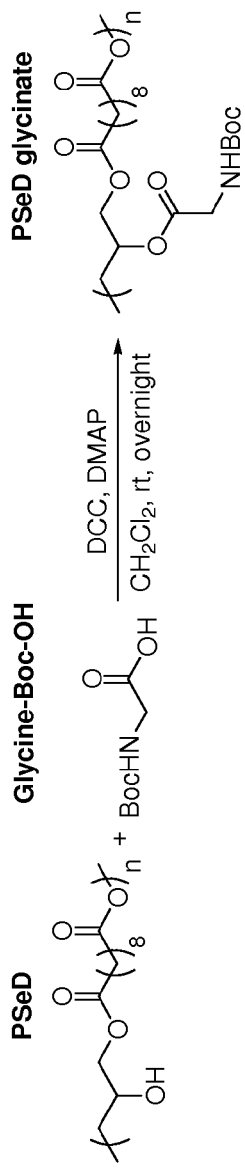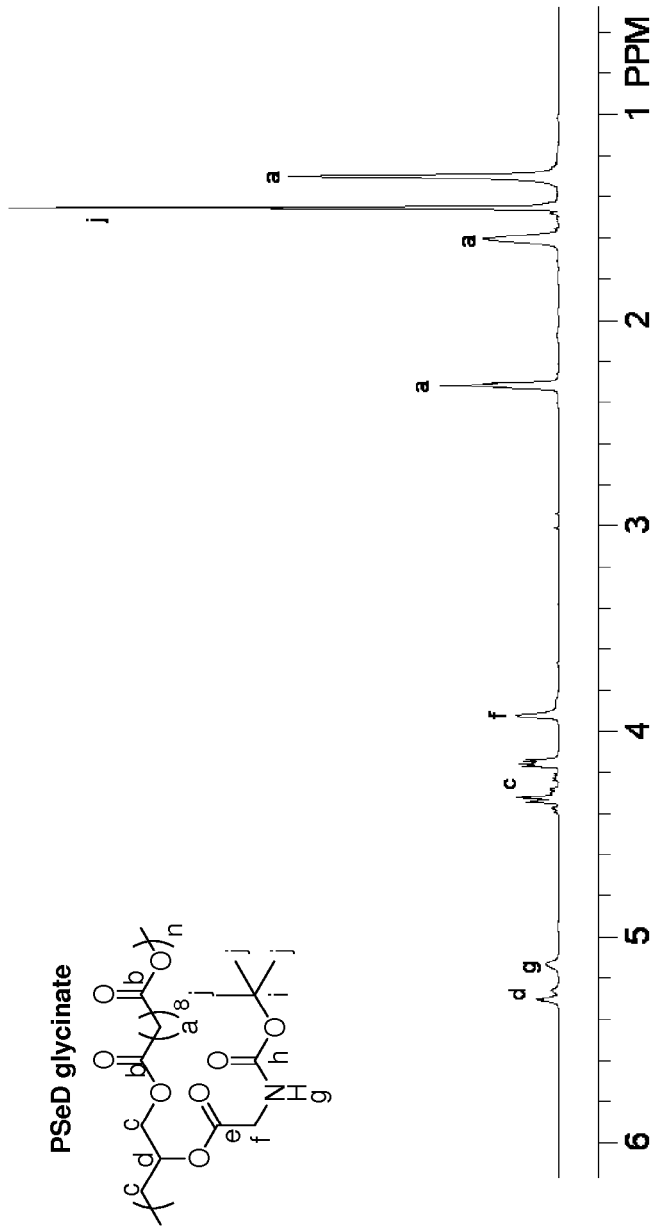
Fig. 7
Fig. 8A

| No | Diacid | Di-epoxide | Generation 1 polymers | yield |
|---|---|---|---|---|
| 1A | 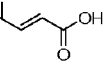 | 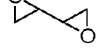 | 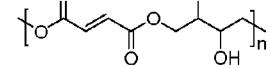 | >99% |
| 1B | 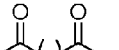 | 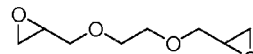 | 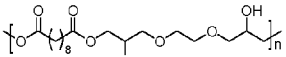 | 75% |
| 1C | 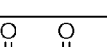 | 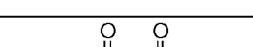 | 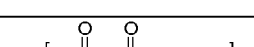 | 87% |
| 1D | 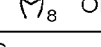 | 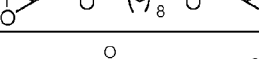 | 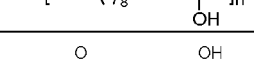 | >99% |
| 1E | 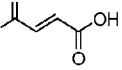 | 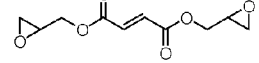 | 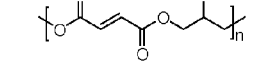 | 73% |
| 1F |  | 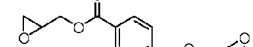 | 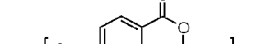 | 98% |
| 1G | 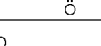 | 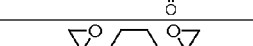 |  | 87% |
| 1H | 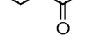 | 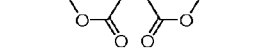 | 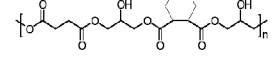 | 99% |

[a] The reactions were performed in N, N-dimethylformamide (DMF) at 90 °C, within a $N_2$ atmosphere using 0.6 mol% initiator bis(tetrabutylammonium) sebacate for 26 h. The polymerization could be efficiently controlled by altering reaction conditions providing an additional way to modulate the polymer properties (Table 7).

Fig. 23

ATRP: Atom transfer radical polymerization

| Charge nature | Neutral | Positive | Negative | Zwitterion |
|---|---|---|---|---|
| Polymer | 1C | 2A, 2D, 3A | 2E, 2G | 2B |

| Polymer | Modulus | Fracture stress | Fracture strain |
|---|---|---|---|
| 2H | 0.939 ± 0.485 kPa | 1.359 ± 0.637 kPa | 34.9 ± 5.3% |
| 2I | 0.386 ± 0.034 MPa | 0.567 ± 0.010 MPa | 233.0 ± 28.0% |
| 2J | 2.155 ± 0.557 GPa | > 0.207 GPa[a] | > 85.0%[a] |

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: Biofunctional peptide

<400> SEQUENCE: 1

Ile Lys Val Ala Val
1               5

<210> SEQ ID NO 2
<211> LENGTH: 4
<212> TYPE: PRT
<213> ORGANISM: Artificial Sequence
<220> FEATURE:
<223> OTHER INFORMATION: Biofunctional peptide

<400> SEQUENCE: 2

Arg Gly Asp Ser
1
```

```
<210> SEQ ID NO 3
<211> LENGTH: 6
<212> TYPE: PRT
<213> ORGANISM: Artificial Sequence
<220> FEATURE:
<223> OTHER INFORMATION: Biofunctional peptide

<400> SEQUENCE: 3

Lys Gln Ala Gly Asp Val
1               5

<210> SEQ ID NO 4
<211> LENGTH: 6
<212> TYPE: PRT
<213> ORGANISM: Artificial Sequence
<220> FEATURE:
<223> OTHER INFORMATION: Biofunctional peptide

<400> SEQUENCE: 4

Val Ala Pro Gly Val Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Biofuntional peptide

<400> SEQUENCE: 5

Ala Pro Gly Val Gly Val
1               5

<210> SEQ ID NO 6
<211> LENGTH: 6
<212> TYPE: PRT
<213> ORGANISM: Artificial Sequence
<220> FEATURE:
<223> OTHER INFORMATION: Biofunctional peptide

<400> SEQUENCE: 6

Pro Gly Val Gly Val Ala
1               5

<210> SEQ ID NO 7
<211> LENGTH: 5
<212> TYPE: PRT
<213> ORGANISM: Artificial Sequence
<220> FEATURE:
<223> OTHER INFORMATION: biofunctional peptide

<400> SEQUENCE: 7

Gly Val Gly Val Ala
1               5

<210> SEQ ID NO 8
<211> LENGTH: 4
<212> TYPE: PRT
<213> ORGANISM: Artificial Sequence
<220> FEATURE:
<223> OTHER INFORMATION: Biofunctional peptide

<400> SEQUENCE: 8

Val Ala Pro Gly
1

<210> SEQ ID NO 9
```

```
<211> LENGTH: 6
<212> TYPE: PRT
<213> ORGANISM: Artificial Sequence
<220> FEATURE:
<223> OTHER INFORMATION: Biofunctional peptide

<400> SEQUENCE: 9

Val Gly Val Ala Pro Gly
1               5

<210> SEQ ID NO 10
<211> LENGTH: 4
<212> TYPE: PRT
<213> ORGANISM: Artificial Sequence
<220> FEATURE:
<223> OTHER INFORMATION: Biofunctional peptide

<400> SEQUENCE: 10

Val Gly Val Ala
1

<210> SEQ ID NO 11
<211> LENGTH: 5
<212> TYPE: PRT
<213> ORGANISM: Artificial Sequence
<220> FEATURE:
<223> OTHER INFORMATION: Biofunctional peptide

<400> SEQUENCE: 11

Val Ala Pro Gly Val
1               5

<210> SEQ ID NO 12
<211> LENGTH: 6
<212> TYPE: PRT
<213> ORGANISM: Artificial Sequence
<220> FEATURE:
<223> OTHER INFORMATION: Biofunctional peptide

<400> SEQUENCE: 12

Gly Val Ala Pro Gly Val
1               5

<210> SEQ ID NO 13
<211> LENGTH: 6
<212> TYPE: PRT
<213> ORGANISM: Artificial Sequence
<220> FEATURE:
<223> OTHER INFORMATION: Biofunctional peptide

<400> SEQUENCE: 13

Ile Lys Val Ala Val Ser
1               5
```

POLYESTERS, METHODS OF MAKING POLYESTERS AND USES THEREFOR

CROSS-REFERENCE TO RELATED APPLICATIONS

This application is a National Stage of International Patent Application No. PCT/US2011/022381, filed Jan. 25, 2011, which claims the benefit under 35 U.S.C. §119(e) of U.S. Provisional Patent Application No. 61/298,052, filed Jan. 25, 2010, and U.S. Provisional Patent Application No. 61/299,404, filed Jan. 29, 2010, each of which is incorporated herein by reference in its entirety.

STATEMENT REGARDING FEDERALLY-SPONSORED RESEARCH AND DEVELOPMENT

This invention was made with government support under Grant Nos. HL089658 and EB008565 awarded by the National Institutes of Health. The government has certain rights in the invention.

The Sequence Listing associated with this application is filed in electronic format via EFS—Web and is hereby incorporated by reference into the specification in its entirety. The name of the text file containing the Sequence Listing is 6527_122160.ST25.txt. The size of the text file is 2,602 bytes, and the text file was created on Jul. 18, 2012.

Provided herein are novel polymer compositions useful in drug delivery and tissue engineering, among other uses, and methods of making and using the polymer compositions.

Synthetic polymers are widely used in various fields including transportation, construction, packaging, electronics, and healthcare, and have made a tremendous impact on modern materials. However traditional polymers are petrochemical-based and nondegradable, which lead to huge consumption of limited petroleum resources and poses environmental concerns. Moreover, biodegradable polymers have been recognized to play a central role in modern biomedical technologies including tissue engineering, regenerative medicine, gene therapy, and drug delivery. All these have spurred the development of renewable, biodegradable, environmentally friendly, and biocompatible polymers, where aliphatic polyesters such as polylactide are the most widely utilized. However, most of these aliphatic polyesters lack free functional groups and thus their properties are difficult to modulate. Most are semi-crystalline, hydrophobic, stiff, and lack functionalization cites, which greatly limit their application. Introduction of functional groups to polymers can efficiently modulate various polymer properties including hydrophilicity, degradability, physical, chemical, and biologic properties. Furthermore, these functional groups provide versatile routes to conjugate a variety of bioactive molecules such as peptides, saccharides, and biotin. This can lead to novel biomaterials with diverse bioactivities. The reaction of pendant groups can further convert corresponding polymers to branched and network polymers, which provide more means to modulate their properties. Therefore functionalized polyesters are very promising new generation biodegradable materials. However the synthesis of functionalized polyesters is still a formidable challenge. Current strategies, either polycondensation or lactone ring-opening polymerization are inefficient. Chemical synthesis usually involves a tedious multistep route with a low overall yield and toxic catalyst. Enzyme catalyzed polycondensation provides a relatively simple method, however it is usually compromised by poor product quality with low molecular weight and large polydispersity index (PDI), and limited choices of substrates. In light of this, a new strategy to efficiently synthesize functionalized polyesters is highly desirable.

SUMMARY

Herein we describe a simple and powerful synthetic platform to a large variety of functionalized polyesters. Methods are provided that utilize ring-opening polymerization between polyacids and poly-cyclic ethers (epoxide and oxetane etc.) or using monomers containing both acid and cyclic ether groups would produce polyester with free —OH groups. The key point of the synthetic strategy is that the cyclic ethers serves as both the active polymerization functionality and the precursor of the polyol moiety. Thus the polyester backbone and the pendant hydroxyl groups are formed in just one step without protection and deprotection.

A method is provided for making a polyester composition. In its most general sense, the method comprises polymerizing a first compound having either one or two cyclic ether groups having the structure

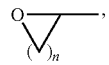

in which n is 1-4 and no additional reactive groups. The first compound is polymerized in a polymerization reaction with a second compound that is the same or different from the first compound, comprising one or two carboxyl groups and no additional reactive groups. In the context of the initial polymerization in which the polyester is formed, a reactive group means a group that will substantially interfere with or participate in reactions between the cyclic ether groups and the carboxyl groups in the polymerization reactionwithout a further modification. As such, B and B', described below, may comprise groups or blocked groups, such as blocked (protected, e.g., with tboc, FMOC or cbz) amines, that under different reaction conditions, such as conditions suitable for deprotection of a protected amine and then reacting the amine with another reactive group, the groups become reactive. Determining whether a group is reactive and under what conditions is for the large part within the skill of a person of ordinary skill in the chemical arts, and even if a group cannot be determined as being reactive by textbook chemistry, interference with the polymerization reaction can be readily determined by analyzing the resultant composition using standard methods, including NMR and IR spectroscopy, among many other commonly-available methods.

The reaction proceeds equally well when the first compound comprises two of the cyclic ether groups, and the second compound comprises two carboxyl groups, and when each of the first and second compounds comprises one cyclic ether group and one carboxyl group, such that wherein if the first compound has only one cyclic ether group, then it also comprises a carboxyl group and the second compound comprises a cyclic ether group having the structure

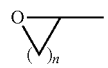

in which n is 1-4.

Thus in one embodiment, the method comprises (co)polymerizing a compound having the structure A-B-A' with a compound having the structure HOC(O)—B'—C(O)OH (a dicarboxylic acid), where A and A' are cyclic ethers having the structure

in which n is 1-4 and A and A' can be the same or different. B' may not be present. B and B' are non-reactive organic (carbon-containing) groups, including, but not limited to: alkyl, ether, tertiary amine, ester, amide, or alcohol, and can be linear, branched or cyclic, saturated or unsaturated, aliphatic or aromatic, and optionally comprise one or more protected active groups, such as, without limitation, protected amines and acids. B and B' can be the same or different. The compound A-B-A' may be prepared by direct esterification of glycidol with a compound, such as XOC(O)—B—C(O)OX' in which X and X' are independently halide, for example in the presence of triethylamine at less than 0° C.

In an alternate embodiment, the method comprises polymerizing a compound having the structure A-B—C(O)OH with a compound having the structure A'-B'—C(O)OH that is the same or different than A-B—C(O)OH. A and A' are cyclic ethers having the structure

in which n is 1-4 and A and A' can be the same or different. B and B' are non-reactive organic groups, including, but not limited to: alkyl, ether, tertiary amine, ester, amide, or alcohol, and can be linear, branched or cyclic, saturated or unsaturated, aliphatic or aromatic, and optionally comprise one or more protected active groups, such as, Without limitation, protected amines and acids, and B and B' can be the same or different, to produce a polyester. In one embodiment, A-B—C(O)OH and A'-B'—C(O)OH are the same. In another, A-B—C(O)OH and A'-B'—C(O)OH are different.

As illustrated in the Examples below, B and B' may be a variety of structures. In the Examples, one or both of B and B' are selected from the group consisting of: —O(O)C—(CH$_2$)$_8$—C(O)O—, —CH═CH—, —CH$_2$—CH$_2$—, phenyl, —O—CH$_2$—CH$_2$—O—, —O—CH═CH—O—, —O(O)C—CH═CH—C(O)O—, —O(O)C-phenyl-C(O)O—, —O(O)C-cyclohexy-C(O)O—, —CH(OH)—CH(OH)—, —O(O)C—C(NHY)—CH$_2$—C(O)O— where Y is a protective group, and —O(O)C—C(NHY)—CH$_2$—CH$_2$—C(O)O where Y is a protective group. One or both of B and B' are alkyl groups that may have any number of carbon atoms so long as the polymerization reaction can proceed. As can be seen in the Examples below, there is a great deal of flexibility as to the choice of B and B'. In one embodiment, one or both of B and B' are aliphatic alkyl groups. In another, one or both of B and B' are saturated alkyl groups. In a further embodiment, one or both of B and B' are saturated straight-chain alkyl groups (e.g., C$_{0-20}$, such as a sebacic group (C$_8$)). Likewise, there is some variation expected with respect to the cyclic ether group. Two embodiments to the cyclic ether group are epoxy groups and oxetane groups. As shown below, one embodiment of the polyester is produced by reacting diglycidyl sebacate with sebacic acid (HOC(O)—(CH$_2$)$_8$—C(O)OH) to produce poly(sebacoyl diglyceride) PSeD.

The polymerization reaction occurs spontaneously, though use of an initiator or other reagents increases speed and efficiency. Therefore, the method is conducted in the presence of one or more nucleophilic reagent, such as bromide, iodide, alkoxide, sulfide, carboxylate. Cations, such as organic cations, including ammonium, phosphonium, or inorganic cations, such a lithium, sodium can assist the ring opening reaction by interaction with the oxygen atom in the cyclic ether ring. Potential initiators can be obtained by combine the nucleophilic group and cation in one compound, as with tetrabutylammonium bromide, tetrabutylammonium fluoride, tetrabutylammonium iodide, tetrabutylammonium sebacate, tetraphenylphosphonium chloride, tetramethylphosphonium iodide, sodium methoxide, lithium acetate, and sodium sulfide. The method may be conducted at any useful temperature As shown herein, the compositions prepared by the described methods can be functionalized with virtually any suitable functional group at the pendant OH groups that are generated by the polymerization, such as by a dicarboxylic acid, including as a group maleic acid or succinic acid. Because B and B' may contain blocked or otherwise non-reactive groups in the original polymerization conditions, those groups may be reacted under different conditions or after deprotection, to functionalize the composition. As indicated below, use of blocked aspartic or glutamic acid for B or B' is such a case (e.g., cbz-boc-FMOC-protected amino acids or amines). In one embodiment, pendant OH groups are functionalized with one or more protected amino acids (such as (e.g., N-tert-butoxylcarbonyl (Boc)-protected glycine or (Boc)-or (FMOC)-protected aspartic acid). A nerve cell growth scaffold may be prepared by functionalizing the pendant OH with an acetylcholine group (e.g., 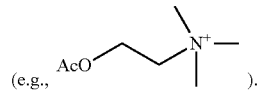 ).

A photolithography composition useful in MEMS, NEMS or other microstructure fabrication methods is produced when pendant OH is functionalized to produce a reversibly photo-crosslinkable polymer network. In another embodiment, the polyester, for instance the pendant OH is functionalized with a peptide, such as a biofunctional peptide for instance one or more of Ile-Lys-Val-Ala-Val (IKVAV) (SEQ ID NO: 1), Arg-Gly-Asp (RGD), Arg-Gly-Asp-Ser (RGDS) (SEQ ID NO: 2), Ala-Gly-Asp (AGD), Lys-Gln-Ala-Gly-Asp-Val (KQAGDV) (SEQ ID NO: 3), Val-Ala-Pro-Gly-Val-Gly (VAPGVG) (SEQ ID NO: 4), APGVGV (SEQ ID NO: 5), PGVGVA (SEQ ID NO: 6), VAP, GVGVA (SEQ ID NO: 7), VAPG (SEQ ID NO: 8), VGVAPG (SEQ ID NO: 9), VGVA (SEQ ID NO: 10), VAPGV (SEQ ID NO: 11) and GVAPGV (SEQ ID NO: 12). In one example, the pendant OH is functionalized with IKVAVS (SEQ ID NO: 13) by reacting the polymer with Boc-IK(Boc)VAVS(tBu)-OH.

The polymer composition can be prepared with and/or functionalized with compounds that are charged. Thus the overall charge of the resultant polymer composition can be modulated, and the composition can be used to bind other charged compositions in a non-covalent manner. In one instance, the charge is positive. In another, the charge is negative. As show below, the composition can be functionalized with positively-charged groups by incorporating amino acids into the structure. An example is the poly(ethylene argininylaspartate diglyceride) (PEAD) composition described below. The positively-charged compound may be bound to a negatively-charged polyanion, such as heparin or heparin sulfate. The resultant structure is highly effective as a delivery vehicle for growth factors, such as NGF and especially FGF-2. Thus also provided herein is an active agent delivery composition and a method of delivering an active agent to a patient comprising binding the active agent to a composition as described herein and delivering the bound active agent to a patient in an amount to achieve a desired therapeutic end-point.

In one embodiment, HOC(O)—B'—C(O)OH is blocked aspartic acid and the method comprises reacting the blocked amino group with blocked arginine to produce poly(ethylene argininylaspartate diglyceride) (PEAD). The composition is then bound to one of heparan sulfate or heparin to the PEAD to produce polyanion-modified PEAD. A growth factor (e.g., a heparin-binding growth factor, including, but not limited to, VEGF, FGF, BMP, PDGF, NGF, BDNF, CDNF, HGF, and heparin-binding IGF,) is then bound to the polyanion-modified PEAD. In two non-limiting embodiments, the growth factor is nerve growth factor (NGF) or basic fibroblast growth factor (FGF-2). As seen below, the FGF-2 active agent delivery composition is useful in producing angiogenesis in a patient and the NGF active agent delivery composition is useful in promoting nerve growth. Thus provided are methods of increasing angiogenesis or nerve growth in a patient comprising administering the FGF-2 active agent delivery composition or the NGF active agent delivery composition to the patient at a site to cause respectively increased angiogenesis or nerve growth at the site in the patient.

The compositions described herein may be functionalized to contain a negatively-charged group, such as with a dicarboxyl compound, such as succinate or maleate, and then reacted with calcium to produce a calcium salt, which can then be reacted with phosphate to produce a calcium phosphate (CAP) functionalized composition. This is expected to be useful in hard-tissue regeneration.

The compositions described herein also are useful as cell-growth scaffolds that can be used in methods of growing cells in vitro or in vivo. The compositions can be mixed to achieve a useful end-result. For instance, the above-described active-agent delivery vehicle can be mixed with a peptide-functionalized and/or a CAP-functionalized polymer composition to produce an enhanced cell-growth environment.

In one further embodiment, the pendant OH groups of the polyester, such as PSeD, are functionalized with a compound comprising a phosphate group or a phosphate group. This composition is shown below to have excellent ability to as a cell growth scaffold for supporting hard tissue regeneration. Thus provided is a method of repairing hard tissue (e.g., bone) comprising implanting the phosphate-functionalized composition in a patient to produce bone growth at the site of implantation. Related to these embodiments are a method of inducing neurite formation in a neuron comprising contacting a neuron with an active-agent delivery vehicle comprising NGF, prepared as described herein.

A photolithography method also is provided. The method comprising depositing onto a substrate a polymer composition prepared when the pendant OH of the polyesters described above is functionalized to produce a reversibly photo-crosslinkable polymer network; and either exposing the polymer-coated surface to ultraviolet light at a wavelength for cross-linking the polymer (e.g., λ=approximately 365 nm) composition in a pattern and removing non-polymerized polymer; or exposing the polymer-coated surface to ultraviolet light at a wavelength for cross-linking the polymer composition, and exposing a portion of the cross-linked polymer-coated surface to ultraviolet light at a wavelength for cleaving the photo-cross-linked polymer (e.g., λ<approximately 220 nm) in a pattern and removing non-crosslinked (i.e., the cleaved) polymer.

A polymer composition is therefore provided. The composition comprises the structure [—OC(O)—B'—CH(OR1)-B—]$_n$ or —[OC(O)—B—C(O)O—CH$_2$—CH(O—R1)-CH$_2$—B'—CH$_2$—CH(O—R2)-CH$_2$—]$_n$, in which B and B' are the same or different and are organic groups, or B' is not present, including, but not limited to: alkyl, ether, tertiary amine, ester, amide, or alcohol, and can be linear, branched or cyclic, saturated or unsaturated, aliphatic or aromatic, and optionally comprise one or more protected active groups, such as, without limitation, protected amines and acids, and R1 and R2 are the same or different and are hydrogen or a functional group (e.g., as described herein). As seen below, the composition exhibits low polydispersity, with a polydispersity index of less than 3.0, and in many cases less than 2.0. The functional groups may vary as indicated above. For example, in certain embodiments, R1 and R2 are independently groups comprising

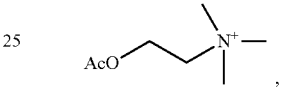

a carboxy-containing group, an α, β unsaturated carboxylic acid (such as cinnamic group (e.g., functionalized with cinnamic acid, p-coumaric acid, ferulic acid, caffeic acid); an amine-containing group, a quaternary ammonium containing group, maleic acid, a peptide; maleate; succinate or phosphate, halo-containing groups. In one embodiment, one or more of B, B', R1 and R2 are charged such that it is possible to bind various water insoluble organic or inorganic compounds to the polymer, such as magnetic inorganic compounds. As above, in one embodiment, one or more of B, B', R1 and R2 are positively charged. In one embodiment, one or both of R1 and R2 are functionalized with a phosphate group. In another embodiment, the composition is attached non-covalently to a calcium phosphate (including as a group, for example and without limitation: hydroxyapatite, apatite, tricalcium phosphate, octacalcium phosphate, calcium hydrogen phosphate, and calcium dihydrogen phosphate). In yet another embodiment, R1 and R2 are independently one Ile-Lys-Val-Ala-Val (IKVAV) (SEQ ID NO: 1), Arg-Gly-Asp (RGD), Arg-Gly-Asp-Ser (RGDS) (SEQ ID NO: 2), Ala-Gly-Asp (AGD), Lys-Gln-Ala-Gly-Asp-Val (KQAGDV) (SEQ ID NO: 3), Val-Ala-Pro-Gly-Val-Gly (VAPGVG) (SEQ ID NO: 4), APGVGV (SEQ ID NO: 5), PGVGVA (SEQ ID NO: 6), VAP, GVGVA (SEQ ID NO: 7), VAPG (SEQ ID NO: 8), VGVAPG (SEQ ID NO: 9), VGVA (SEQ ID NO: 10), VAPGV (SEQ ID NO: 11) and GVAPGV (SEQ ID NO: 12)). In specific embodiments, the composition may be PSeD, functionalized PSeD.

In another embodiment, B and B' are derived from blocked aspartic acid or blocked glutamic acid, which are optionally further derivatized with an amine-containing group, for example, the blocked amines of the aspartic acid or glutamic acid are further derivatized with lysine or arginine. The composition also may be complexed with heparin or heparan sulfate, which then may be further complexed with a growth factor. In one embodiment, the composition comprises PEAD and optionally further comprises heparin or heparin sulfate complexed (that is non-covalently bound) with the PEAD to produce a PEAD vehicle, which then may further comprise an active agent complexed with the PEAD vehicle. The active agent may be any physiologically active compound or composition, such as a small molecule, cytokine, growth factor, drug, etc. In one embodiment, the active agent is a growth factor, such as one or more of a FGF, an EGF and a VEGF.

BRIEF DESCRIPTION OF THE DRAWINGS

FIG. 1. Example of the newly designed synthetic strategy of PSeD (poly(sebacoyl diglyceride)) leads to a biodegradable polymer that retains the biocompatibility of PGS but with a more defined structure that is advantageous for subsequent functionalization.

FIG. 2. Direct esterification under optimized conditions produced the monomer diglycidyl sebacate in one step with simpler procedure and higher yield than the previous two-step route (Gumera C B, Wang, Y. Modulating neuronal responses by controlled integration of acetylcholine-like functionalities in biomimetic polymers. Adv Mater 2007; 19(24):4404-9).

FIG. 7. A model reaction for the conjugation of biomolecules to PSeD.

FIGS. 23. Epoxide ring opening polymerization—a simple and versatile synthetic platform to functionalized polyesters with free hydroxyl groups.

(FIG. 25A) Diverse modification of the free hydroxyl groups—a model of linear post-functionalization of generation 1 polymers. (FIG. 25B) Diverse polymeric networks yielded by various crosslinking of generation 1 polymers—another efficient way for post-functionalization. (FIG. 25C) Two examples for further functionalization of generation 2 polymers to generation 3 polymers either by linear conjugation or crosslinking. Reagents and conditions: (a) i. Boc-Gly-OH (Boc, tert-butyloxycarbonyl; Gly, glycine), N, N'-dicyclohexylcarbodiimide (DCC), 4-dimethylaminopyridine (DMAP), CH$_2$Cl$_2$, room temperature (rt), 18 h; ii. CF$_3$CO$_2$H, rt, 1 h (b) i. Boc-Glu-OtBu (Glu, glutamic acid; tBu, certbutyl), DCC, DMAP, CH$_2$Cl$_2$, rt, overnight; ii. CF$_3$CO$_2$H, rt, 0.5 h; (c) Cinnamic acid, DCC, DMAP, CH$_2$Cl$_2$, rt, overnight; (d) i. Boc-IK(Boc)VAVS(tBu)-OH (I, isoleucine; K, lysine; V, valine; A, alanine; S, serine), DCC, DMAP; ii. CF$_3$CO$_2$H, rt, 0.5 h. (e) Succinic anhydride, DMF, 45-115° C., 2 h; (f) ClCH$_2$CO$_2$Cl, Pyridine, DMAP, CH$_2$Cl$_2$, −78° C.-rt, 24 h; (g) POCl$_3$, −10-5° C., 2.5 h; (h) 50 wt % PEG-diacrylate (PEG, polyethylene glycol), 0.5 wt % Igracure 2959, 365 nm UV, 24 min; (i) 0.9 wt % Citric acid, 95-120° C. for 19 h, 120° C., vacuum for 45 h; (j) 10 wt % 1,6-Hexyldiisocyanate, rt—140° C., vacuum for 50 h; (k) $Me_2NCH_2CH_2OAc$, acetone, rt, 17 h; (l) 365 nm UV.

(FIG. 36A) Chemical structure of poly (ethylene argininylaspartate diglyceride) (PEAD). The backbone of PEAD composed of aspartic acid and ethylene glycol diglyceride is linked together by ester bonds. The conjugation of arginine renders the polymer two positive charges, ammonium and guanidinium moieties, per repeating unit at the physiological condition. (FIG. 36B) Heparin has high solubility in the aqueous solution. Once addition of PEAD, the solution becomes turbid due to neutralization of negative charges. [PEAD:Heparin] complex forms coacervate and precipitates to the bottom after 24 h incubation. (FIG. 36C) SEM micrograph revealed the fibrous and globular features of [PEAD:Heparin] complex. Scale bar, 1 µm. (FIG. 36D) Schematic representation of the interaction between the heparin-binding growth factors and [PEAD:Heparin] complex. The Coulombic attraction between PEAD and heparin is able to incorporate heparin-binding growth factors into the complex. (FIG. 36E) The loading efficiency examined by western blot suggested that [PEAD:Heparin] can incorporate the majority of FGF-2 in the solution. Continuing increasing the ionic strength of the solution to 5 folds of the normal saline condition disrupted the interaction between PEAD, heparin and FGF-2. Therefore, FGF-2 was not precipitated after centrifugation. (FIG. 36F) In vitro tube formation of HUVECs in the 30 fibrin gel. HUVECs mixed with bolus FGF-2 or the delivery matrix were encapsulated in the fibrin gel. After incubation for 3 days, the image of the delivery matrix group revealed an evident tube network connected by differentiated cells. On the contrary, bolus FGF-2 only induced sparse cells scattering in the gel. Scale bar: 100 µm.

(FIG. 37B) Hemoglobin quantification compared the extent of angiogenesis between different groups. The result suggested that delivered matrix group had a higher amount of hemoglobin 2 weeks post-injection whereas bolus FGF-2 did not have statistical difference between the control and delivery vehicle groups. This difference lasted at least for 4 weeks. (mean±s.d., n=4-8 for each condition) One-way ANOVA followed by Bonferroni correction was applied for multiple comparisons. *$p<0.05$, ** $p<0.01$. (FIG. 37C) The ratio of hemoglobin at the injection sites and the contralateral sites. For the delivered matrix, the ratio was significantly higher than that of the bolus group. The result explained that FGF-2 was well localized at the injection site by the delivery vehicle. Student's t-test was used as a statistical tool. *$p<0.05$, ** $p<0.01$. (FIG. 37D) Hematoxylin and eosin staining of subcutaneous tissues after 4 weeks. For the control, delivery vehicle and bolus FGF-2 groups, there were no clear vasculature in the hypodermis region. The delivered matrix, however, revealed the feature of blood vessel which had a closed inner layer of nucleated cells surrounded by smooth muscle bundles. Magnification of the representative images is 200×.

(FIG. 38A) Representative confocal micrographs (200×) showed the distribution of the blood vessel associated markers CD31 (endothelial cell, red) and SMA (mural cell, green) of each group at three time points. Both the bolus and delivered groups revealed a higher quantity of CD31-positive cells than the control group after 1 week whereas only the delivered group had an obvious increase of the expression of alpha-SMA after 2 weeks. The circular vessel-like structures were also found in the field. After 4 weeks, more CD31-positive and alpha-SMA -positive cells observed in the field possibly implied the long term efficacy of the delivered FGF-2. (FIG. 38B) High magnification (600×) imaging revealed the maturation of the blood vessels by delivered FGF-2. The enclosed arrangement of CD31-positive cells was surrounded by the alpha-SMA-positive cells. (FIG. 38C) Quantitative comparison of the expression of CD31 and α-SMA at week 4. Random fields were chosen for the number of CD31-positve and alpha-SMA-positive cells. The number was divided by the area of the tissue and normalized by the value of the control group. The result indicated the number of CD31-positive cells of the delivery matrix group was higher than those of other groups by roughly 40% to 70%. More significantly, the number of alpha-SMA-positive cells of the delivered group was 2.8 folds of that of the bolus group. Both indicators demonstrated the higher bioactivity of the delivery matrix. One-way ANOVA followed by Bonferroni correction was utilized as a statistical tool for multiple comparisons. *p<0.05, ** p<0.01.

(FIG. 39A) The co-localization of CD31-positive and PDFGR-β-positive cells suggested the controlled delivery matrix had rapidly recruited pericytes to interact with endothelial cells. This phenomenon, nonetheless, was not seen in the bolus FGF-2 group. (FIG. 39B) Significant co-localization of vWF- and CD31-positive cells supported that the newly proliferated endothelial cells were effective in hemostasis. (FIG. 39C) Both alpha-SMA and desmin are markers for mural cells. The expression pattern revealed that larger vessels co-expressed these markers whereas smaller vessels were dominant in the expression of desmin. (arrows) (FIG. 39D) SMMHC, the marker of the contractility of vascular smooth muscle cells, was expressed in the larger vessels in the delivery matrix group. Smaller vessels did not have evident SMMHC expression (arrows). On the other hand, the SMMHC expression was not detected in the bolus FGF-2 group even with the vessel expressing abundant alpha-SMA, suggesting the smooth muscle cells did not progress into contractile pheontype. Magnification of the large area: 200×. Magnification of the local area: 600×.

(FIG. 41A) 1H NMR spectrum and (FIG. 41B) FTIR spectrum of PFB-maleate.

DETAILED DESCRIPTION

Figure 3A:
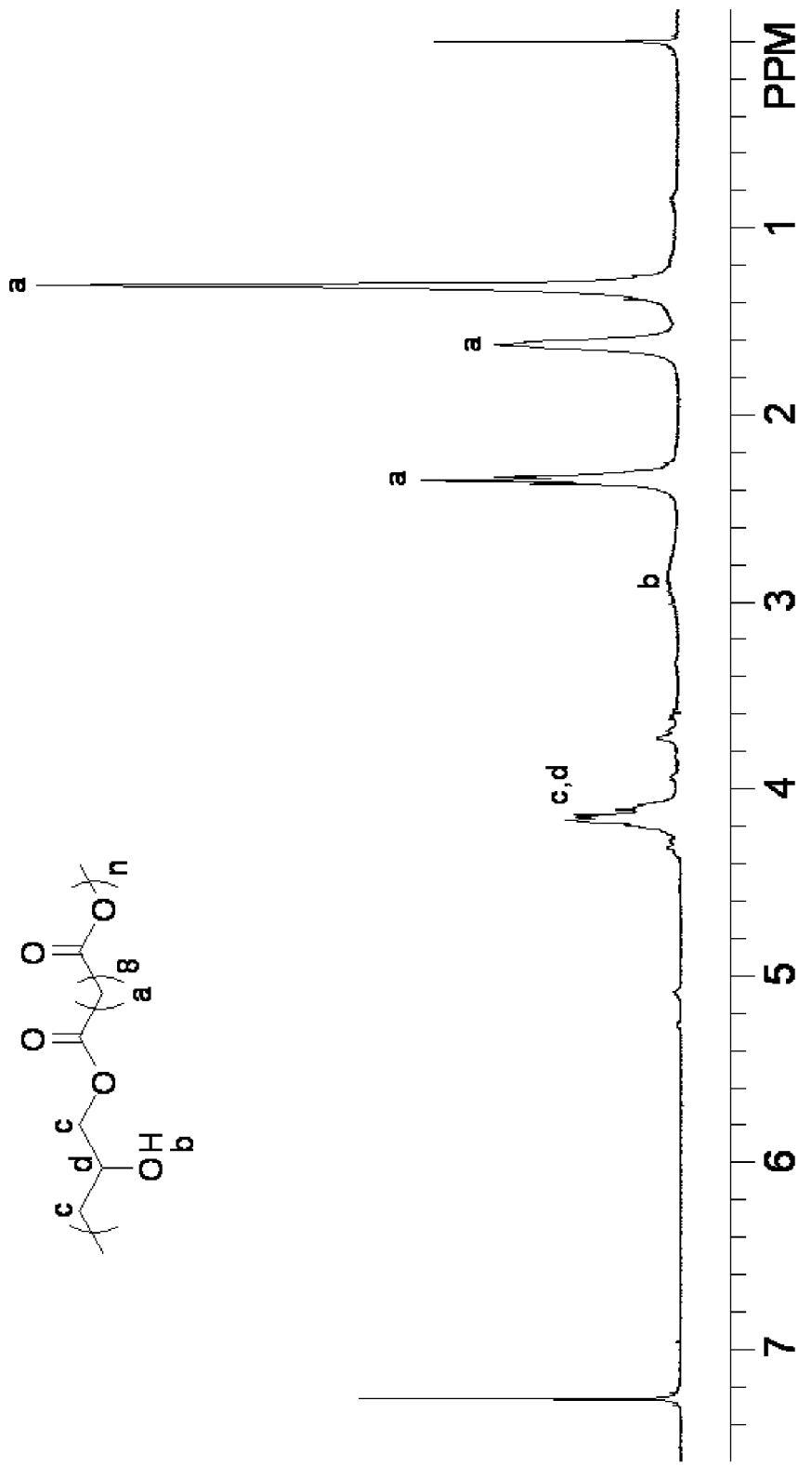
FIG. 3. (A) The $^1$H NMR spectrum of PSeD is consistent with the proposed structure with glyceryl moiety at δ from 3.55-4.54 ppm, sebacoyl moiety at δ 1.31, 1.62, and 2.35 ppm, and —OH group at δ 2.89 ppm. (B) The $^{13}$C NMR spectrum of PSeD corroborates well with the $^1$H NMR. The resonance of the glyceryl moiety occurs at δ 61.31-72.08 ppm, the sebacoyl moiety at δ 24.78, 28.95, and 34.05 ppm, and the ester group at δ 173.94 ppm.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As indicated above. methods are provided that utilize ring-opening polymerization between polyacids and poly-cyclic ethers (epoxide and oxetane etc.) or using monomers containing both acid and cyclic ether groups would produce polyester with free —OH groups (Scheme 1, using diacids and diepoxides as example). The key point of the synthetic strategy is that the cyclic ethers serve as both the active polymerization functionality and the precursor of the polyol moiety. Thus the polyester backbone and the pendant hydroxyl groups are formed in just one step without protection and deprotection.

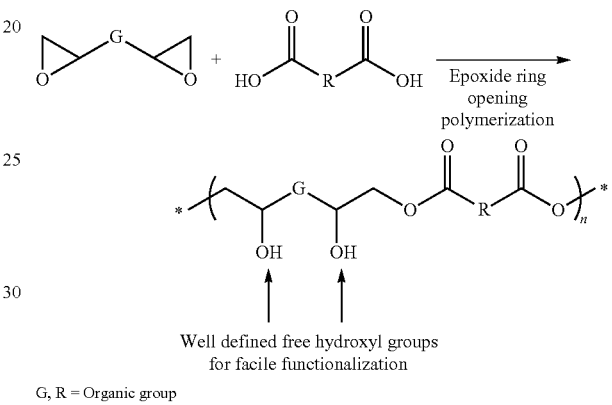

Scheme 1. A simple and versatile synthetic strategy to functionalizable polyester.

G, R = Organic group

By varying the starting materials, reaction conditions, and functionalization of the polymers, polyesters with a wide range of physical, thermal, mechanical, chemical, and biological properties can be obtained. It is a versatile platform leading to various functionalized polyesters with tailored properties.

Such polymer compositions, with or without further modification, can support a myriad of uses. In the medical field, the wide range of mechanical properties from very soft hydrogel to stiff polymers and the wide range of biodegradability are expected to be useful for controlled drug delivery for various medical applications. The drug delivery device may be tailored to deliver drugs to many tissues, such as, for example, the eye, muscle, skin, GI tract, cardiovascular system, lung, kidney, bladder, etc. As a tissue engineering scaffold, the compositions may be used for applications in the heart, lung, blood vessels, kidney, liver, nervous system, cartilage, skin, tendon, muscle, GI tract, trachea etc. The compositions exhibit a wide range of physical properties from liquid to solid. They can be fabricated to various shapes, topologies, and patterns. They can be made to be water soluble or to be very hydrophobic. As a non-limiting example, electro-spinning makes solid materials to micro- to nano-fibers, and lithography techniques make crosslinkable liquid materials to various microtopologies. The polymers may be elastomeric, and can exhibit shape memory properties. The materials can be used to make biodegradable sutures, actuators, catheters, stents, and smart scaffolds, which can also be coupled with drug delivery for sophisticated medical applications. For example, the materials can be designed to be water soluble and photocrosslinkable materials for drug, gene, and cells delivery. They can be crosslinked in water in the presence of drug, gene, and cells to serve as their delivery vehicles.

The materials described herein are also highly functionalizable. They can be functionalized by various chemical moieties for a desirable effect. For example, they may be functionalized with biological molecules to obtain bioactive polyesters with various functionalities to modulate their properties for regenerative biomaterials, medical devices, and other medical engineering applications. For example, as shown below, the polyester can be functionalized with phosphate for orthopedic applications, bone regeneration, or load bearing graft. They also can be coupled with growth factors to encourage vascularized bone regeneration. They can be functionalized with bioactive peptides, acetylcholine-like motif, and other nerve active molecules for nerve regeneration. In one example, they are functionalized with cationic groups, such as quaternary amines or an ammonium group, to produce an antimicrobial polymer. They also may be functionalized with zwitterions to produce a non-fouling polymer.

Antimicrobial derivatives, such as such as quaternary amine or ammonium group functionalized polymer compositions also may be used in clothing, such as socks, insoles, undergarments, shields, etc. or in disposable personal care items, such as tooth brushes, dental floss, dental fixtures, such as retainers and expanders, tampons, personal lubricants, condoms, etc.

The polymer compositions may be functionalized with amino groups, for example: amino acids like aspartic and glutamic acid (also blocked versions thereof, such as tboc- or cbz-aspartic or glutamic acids) may be reacted with a di-epoxide to produce the polyester having pendant amino groups. In another embodiment, they are functionalized with maleic anhydride to produce photocrosslinkable materials, which can easily be fabricated into various shapes and patterns for biomedical applications. In yet another embodiment, they are functionalized with cinnamyl group and similar groups so it can be reversibly photocrosslinked.

The compositions can be used for micro- and nano-patterned device for drug delivery and tissue engineering, prepared, e.g., by reversible photolithography as described below. They can be used as photo-reversible thermoset polymers. They integrate the advantages of both thermoset and thermoplastic. After photo-crosslinking, they can be used as thermoset polymers with corresponding properties. But unlike other thermoset polymers, their crosslinking can be photolitically cleaved to regenerate thermoplastic prepolymer such as PSeD-cinnamate and thus can be refabricated as thermoplastic polymers. This coupled with photolithography can be a powerful tool to easily fabricate intricate structures, including microelectromechanical (MEMS) and nanoelectromechanical (NEMS) structures and devices.

The compositions can be functionalized with superhydrophobic moieties, (e.g.) perfluoroalkanes, perfluoro(alkylsilanes), and/or siloxanes to produce superhydrophobic materials. These compositions can be used for self cleaning medical diagnostic and bioanalytic devices, lab-on-a-chip, microfluidic devices etc.

The compositions can be used to produce compostable materials, such as a variety of environmentally degradable materials: such as plastics, elastomers, and fibers. After functionalization, thet can be used as various biodegradable functional materials, for example, as antimicrobial polymers for recyclable disposable food container and other household items. When aromatic starting materials, such as terephthalic acid, are used, a series of aromatic, functionalizable polymers are obtained that degrade much slower, to a point that they can be considered biostable. After functionalization, various functional polymeric materials can be produced. When functionalized with superhydrophobic moieties, (e.g.) perfluoroalkanes, perfluoro(alkylsilanes), and/or siloxanes superhydrophobic materials are produced for use in coatings, paints, roof tiles, fabrics and other surfaces that can stay dry and clean themselves.

As indicated above, a method is provided for preparing a linear polyester, e.g., poly(sebacoyl diglyceride) bearing pendant hydroxyl groups by reacting a compound comprising a cyclic ester group, such as an epoxide group with an organic acid. As an example, the monomer diglycidyl sebacate was prepared via direct esterification of glycidol with sebacoyl chloride under mild conditions. Subsequently sebacic acid opens the epoxy rings of diglycidyl sebacate to produce poly (sebacoyl diglyceride) (Mn=16.6 kDa, PDI=2.5) with an excellent yield (90%). The resultant polymer was characterized by NMR, FTIR, DSC, and TGA. MTT assay using primary baboon smooth muscle cells demonstrated its in vitro biocompatibility. This synthetic strategy provides a versatile platform to a family of biodegradable, functionalized polymers with tunable physiochemical and biological properties useful for a wide variety of biomedical applications.

Polyesters with free functional groups allow facile modifications with biomolecules, which can lead to versatile biomaterials that afford controlled interactions with cells and tissues. Efficient synthesis of functionalizable polyesters is still a challenge that greatly limits the availability and widespread applications of biofunctionalized synthetic polymers. The methods described herein also provide a simple route to prepare a functionalizable polyester by the use of epoxide ring-opening polymerization instead of the traditional polycondensation reaction that produces poly(glycerol sebacate) (PGS). As an example, PSeD has a more defined structure with mostly linear backbone, more free hydroxyl groups, higher molecular weight, and lower polydispersity than PGS. Crosslinking PSeD with sebacic acid yields a polymer five times tougher and more elastic than cured PGS. PSeD exhibits good cytocompatibility in vitro. Furthermore, functionalization by glycine proceeds with high efficiency. This versatile synthetic platform can offer a large family of biodegradable, functionalized polymers with tunable physiochemical and biological properties useful for a wide range of biomedical applications.

Thus, described herein are methods of making polyester compositions.

polymerizing a first compound having either one or two cyclic ether groups having the structure

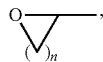

in which n is 1-4 and no additional reactive groups. The first compound is polymerized in a polymerization reaction with a second compound that is the same or different from the first compound, comprising one or two carboxyl groups and no additional reactive groups. In the context of the initial polymerization in which the polyester is formed, a reactive group means a group that will substantially interfere with or participate in reactions between the cyclic ether groups and the carboxyl groups in the polymerization reactionwithout a further modification. As such, B and B', described below, may comprise groups or blocked groups, such as blocked (protected, e.g., with tboc, FMOC or cbz) amines, that under different reaction conditions, such as conditions suitable for deprotection of a protected amine and then reacting the amine with another reactive group, the groups become reactive. Determining whether a group is reactive and under what conditions is for the large part within the skill of a person of ordinary skill in the chemical arts, and even if a group cannot be determined as being reactive by textbook chemistry, interference with the polymerization reaction can be readily determined by analyzing the resultant composition using standard methods, including NMR and IR spectroscopy, among many other commonly-available methods.

Thus in one embodiment, the method comprises (co)polymerizing a compound having the structure A-B-A' with a compound having the structure HOC(O)—B'—C(O)OH (a dicarboxylic acid), where A and A' are cyclic ethers having the structure

in which n is 1-4 and A and A' can be the same or different. B' may not be present. B and B' are non-reactive organic (carbon-containing) groups, including, but not limited to: alkyl, ether, tertiary amine, ester, amide, or alcohol, and can be linear, branched or cyclic, saturated or unsaturated, aliphatic or aromatic, and optionally comprise one or more protected active groups, such as, without limitation, protected amines and acids. B and B' can be the same or different. The compound A-B-A' may be prepared by direct esterification of glycidol with a compound, such as XOC(O)—B—C(O)OX' in which X and X' are independently halide, for example in the presence of triethylamine at less than 0° C.

Alternately, the method comprises
the method comprises polymerizing a compound having the structure A-B—C(O)OH with a compound having the structure A'-B'—C(O)OH that is the same or different than A-B—C(O)OH. A and A' are cyclic ethers having the structure

in which n is 1-4 and A and A' can be the same or different. B and B' are non-reactive organic groups, including, but not limited to: alkyl, ether, tertiary amine, ester, amide, or alcohol, and can be linear, branched or cyclic, saturated or unsaturated, aliphatic or aromatic, and optionally comprise one or more protected active groups, such as, without limitation, protected amines and acids, and B and B' can be the same or different, to produce a polyester. In one embodiment, A-B—C(O)OH and A'-B'—C(O)OH are the same. In another, A-B—C(O)OH and A'-B'—C(O)OH are different. It should be noted that it may be preferable, simpler and more cost-effective to polymerize a single compound A-B—C(O)OH (A'-B'—C(O)OH is the same as A-B—C(O)OH), though a copolymer is produced when A'-B'—C(O)OH that is different than A-B—C(O)OH.

According to certain embodiments, the methods described herein produce a polymer composition.

The composition comprises the structure [—OC(O)—B'—CH(OR1)-B—]$_n$ or —[OC(O)—B—C(O)O—CH$_2$—CH(O—R1)-CH$_2$—B'—CH$_2$—CH(O—R2)-CH$_2$—]$_n$, in which B and B' are the same or different and are organic groups, or B' is not present, including, but not limited to: alkyl, ether, tertiary amine, ester, amide, or alcohol, and can be linear, branched or cyclic, saturated or unsaturated, aliphatic or aromatic, and optionally comprise one or more protected active groups, such as, without limitation, protected amines and acids, and R1 and R2 are the same or different and are hydrogen or a functional group (e.g., as described herein). As seen below, the composition exhibits low polydispersity, with a polydispersity index of less than 3.0, and in many cases less than 2.0.

The polymers described herein can be functionalized, e.g., at B, B', R1 and R2, meaning they comprise one or more groups with an activity, such as a biological activity. For example and without limitation, as shown herein, the polymer may be functionalized with an acetylcholine-like group or moiety, a cross-linking agent (cross-linking agents contain at least two reactive groups that are reactive towards numerous groups, including sulfhydryls and amines, and create chemical covalent bonds between two or more molecules, functional groups that can be targeted with cross-linking agents include primary amines, carboxyls, sulfhydryls, carbohydrates and carboxylic acids. A large number of such agents are available commercially from, e.g., Thermo fisher Scientific (Pierce) and Sigma).

Other functions that can be provided by or enhanced by addition of functional groups include: increased hydrophobicity, for instance by functionalizing with a superhydrophobic moiety, such as a perfluoroalkane, a perfluoro(alkylsilane), and/or a siloxane; increased hydrophilicity, for instance by functionalizing with polyethylene glycol (PEG); anticoagulation, for instance, by functionalizing with heparin; or antimicrobial, for instance, by functionalizing with a quaternary amine. The polymer can be functionalized with a tag, such as a fluorescent tag (e.g., FITC, a cyanine dye, etc.). The polymer can be functionalized by linking to additional synthetic or natural polymers, including, without limitation: synthetic polymers, such as a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(1-lactide-co-dl-lactide), a polymer comprising a lactone monomer, a polycaprolactone, a polymer comprising carbonate linkages, a polycarbonate, a polyglyconate, a poly(glycolide-co-trimethylene carbonate), a poly(glycolide-co-trimethylene carbonate-co-dioxanone), a polymer comprising urethane linkages, a polyuretlfane, a poly(ester urethane) urea, a poly(ester urethane) urea elastomer, a polymer comprising ester linkages, a polyalkanoate, a polyhydroxybutyrate, a polyhydroxyvalerate, a polydioxanone, a polygalactin, or natural polymers, such as chitosan, collagen, elastin, alginate, cellulose, hyaluronic acid and gelatin. The compositions may be functionalized with organic or inorganic moieties to achieve desired physical attributes (e.g., hardness, elasticity, color, additional chemical reactivity, etc.), or desired functionality. For example, as shown below, the polymer composition may be derivatized with maleic acid or phosphate to achieve excellent compositions for use in hard tissue engineering.

The composition may be functionalized with active agents or polyanionic or polycationic groups to for sequestering active agents for controlled delivery in vivo. Drug products comprising the derivatized polyester compounds described herein may be delivered to a patient by any suitable route of delivery (e.g. oral or parenteral), or even as an implantable device for slow release of the active agent.

The functional groups may vary as indicated above. For example, in certain embodiments, R1 and R2 are independently groups comprising

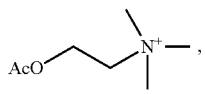

a carboxy-containing group, an α, β unsaturated carboxylic acid (such as cinnamic group (e.g., functionalized with cinnamic acid, p-coumaric acid, ferulic acid, caffeic acid); an amine-containing group, a quaternary ammonium containing group, maleic acid, a peptide; maleate; succinate or phosphate, halo-containing groups. In one embodiment, one or more of B, B', R1 and R2 are charged such that it is possible to bind various water insoluble organic or inorganic compounds to the polymer, such as magnetic inorganic compounds. As above, in one embodiment, one or more of B, B', R1 and R2 are positively charged. In one embodiment, one or both of R1 and R2 are functionalized with a phosphate group. In another embodiment, the composition is attached non-covalently to a calcium phosphate (including as a group, for example and without limitation: hydroxyapatite, apatite, tricalcium phosphate, octacalcium phosphate, calcium hydrogen phosphate, and calcium dihydrogen phosphate). In yet another embodiment, R1 and R2 are independently one Ile-Lys-Val-Ala-Val (IKVAV) (SEQ ID NO: 1), Arg-Gly-Asp (RGD), Arg-Gly-Asp-Ser (RGDS) (SEQ ID NO: 2), Ala-Gly-Asp (AGD), Lys-Gln-Ala-Gly-Asp-Val (KQAGDV) (SEQ ID NO: 3), Val-Ala-Pro-Gly-Val-Gly (VAPGVG) (SEQ ID NO: 4), APGVGV (SEQ ID NO: 5), PGVGVA (SEQ ID NO: 6), VAP, GVGVA (SEQ ID NO: 7), VAPG (SEQ ID NO: 8), VGVAPG (SEQ ID NO: 9), VGVA (SEQ ID NO: 10), VAPGV (SEQ ID NO: 11) and GVAPGV (SEQ ID NO: 12)). In specific embodiments, the composition may be PSeD, functionalized PSeD.

In another embodiment, B and B' are derived from blocked aspartic acid or blocked glutamic acid, which are optionally further derivatized with an amine-containing group, for example, the blocked amines of the aspartic acid or glutamic acid are further derivatized with lysine or arginine. The composition also may be complexed with heparin or heparan sulfate, which then may be further complexed with a growth factor. In one embodiment, the composition comprises PEAD and optionally further comprises heparin or heparin sulfate complexed (that is non-covalently bound) with the PEAD to produce a PEAD vehicle, which then may further comprise an active agent complexed with the PEAD vehicle. The active agent may be any physiologically active compound or composition, such as a small molecule, cytokine, growth factor, drug, etc. In one embodiment, the active agent is a growth factor, such as one or more of a FGF, an EGF and a VEGF.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

The term "alkyl" refers to both branched and straight-chain saturated aliphatic hydrocarbon groups. These groups can have a stated number of carbon atoms, expressed as $C_{x-y}$, where x and y typically are integers. For example, $C_{5-10}$, includes $C_{5-6}$, $C_7$, $C_8$, $C_9$, and $C_{10}$. Alkyl groups include, without limitation: methyl, ethyl, propyl, isopropyl, n-, s- and t-butyl, n- and s-pentyl, hexyl, heptyl, octyl, etc. Alkenes comprise one or more double bonds and alkynes comprise one or more triple bonds. These groups include groups that have two or more points of attachment (e.g., alkylene). Cycloalkyl groups are saturated ring groups, such as cyclopropyl, cyclobutyl, or cyclopentyl. As used herein, "halo" or "halogen" refers to fluoro, chloro, bromo, and iodo.

A polymer "comprises" or is "derived from" a stated monomer if that monomer is incorporated into the polymer. Thus, the incorporated monomer that the podlymer comprises is not the same as the monomer prior to incorporation into a polymer, in that at the very least, certain terminal groups are incorporated into the polymer backbone. A polymer is said to comprise a specific type of linkage if that linkage is present in the polymer.

The polymers described herein are said to be bioerodible or biodegradable. By that, it is meant that the polymer, once implanted and placed in contact with bodily fluids and tissues, or subjected to other environmental conditions, such as composting, will degrade either partially or completely through chemical reactions, typically and often preferably over a time period of hours, days, weeks or months. Non-limiting examples of such chemical reactions include acid/base reactions, hydrolysis reactions, and enzymatic cleavage. The polymers described herein contain labile ester linkages. The polymer or polymers may be selected so that it degrades over a time period. Non-limiting examples of useful in situ degradation rates include between 12 hours and 5 years, and increments of hours, days, weeks, months or years therebetween.

A cell growth matrix (bioscaffold or biological scaffold) is a matrix formed from a polymer composition described herein, for instance by molding, spraying, electrodeposition, etc. Cells and active agents can be incorporated into the matrix as desired. Although referred to as a cell growth matrix, it does not imply that the cells must grow on the matrix or propagate within the matrix, only that the matrix is biocompatible.

Active agents that may be incorporated into the polymer compositions, or derivatized polymer compositions include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, and antiinflammatory proteins or steroidal anti-inflammatory agents); antibiotics; anti-clotting factors such as heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, and streptokinase; growth factors. Other active agents include, without limitation: (1) immunosuppressants; glucocorticoids such as hydrocortisone, betamethisone, dexamethasone, flumethasone, isoflupredone, methylpred-nisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, becacizumab, neovastat; (3) antiproliferatives such as sirolimus, paclitaxel, perillyl alcohol, farnesyl transferase inhibitors, FPTIII, L744, anti-proliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; (4) antibodies; drugs acting on immunophilins, such as cyclosporine, zotarolimus, everolimus, tacrolimus and sirolimus (rapamycin), interferons, TNF binding proteins; (5) taxanes, such as paclitaxel and docetaxel; statins, such as atorvastatin, lovastatin, simvastatin, pravastatin, fluvastatin and rosuvastatin; (6) nitric oxide donors or precursors, such as, without limitation, Angeli's Salt, L-Arginine, Free Base, Diethylamine NONOate, Diethylamine NONOate/AM, Glyco-SNAP-1, Glyco-SNAP-2, (.+-.)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (7) antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, and silver salts such as chloride, bromide, iodide and periodate.

Cells may be microintegrated within a cell growth matrix using a variety of methods. For example, the matrix may be submersed in an appropriate growth medium for the cells of interest, and then directly exposed to the cells. The cells are allowed to proliferate on the surface and interstices of the matrix. The matrix is then removed from the growth medium, washed if necessary, and implanted. Cells of interest are dissolved into an appropriate solution (e.g., a growth medium or buffer) and then sprayed onto a growth matrix. This method is particularly suitable when a highly cellularized tissue engineered construct is desired. In one embodiment, pressure spraying (i.e., spraying cells from a nozzle under pressure) is used to deposit the cells. In another, the cells are electrosprayed onto the non-woven mesh during electrodeposition. Electrospraying involves subjecting a cell-containing solution with an appropriate viscosity and concentration to an electric field sufficient to produce a spray of small charged droplets of solution that contain cells.

The cells that may be incorporated on or into the bioerodibe matrix include but are not limited to stem cells, progenitor (precursor) cells, smooth muscle cells, skeletal myoblasts, myocardial cells, endothelial cells, endothelial progenitor cells, bone-marrow derived mesenchymal cells and genetically modified cells. In certain embodiments, the genetically modified cells are capable of expressing a therapeutic substance, such as a growth factor. Examples of suitable growth factors include angiogenic or neurotrophic factor, which optionally may be obtained using recombinant techniques. Non-limiting examples of growth factors include basic fibroblast growth factor (bFGF or FGF-2), acidic fibroblast growth factor (aFGF), nerve growth factor (NGF), vascular endothelial growth factor (VEGF), hepatocyte growth factor (HGF), insulin-like growth factors (IGF), transforming growth factor-beta pleiotrophin protein, midkine protein.

As suggested above, in one embodiment, the polymer compositions are used as drug-delivery devices. Drug products prepared according to the methods described herein comprise a polymer composition and an active agent. Suitable active agents are described above. In one embodiment, the polymer described above is derivatized with heparin or heparan sulfate, and a growth factor, such as basic fibroblast growth factor (bFGF or FGF-2), acidic fibroblast growth factor (aFGF), nerve growth factor (NGF), vascular endothelial growth factor (VEGF), hepatocyte growth factor (HGF), insulin-like growth factors (IGF), transforming growth factor-beta pleiotrophin protein, or midkine protein is mixed with the derivatized polymer composition. The drug product comprising the derivatized polymer composition and the active agent is administered to a patient in an amount effective to achieve a desired end-point, such as angiogenesis, tissue growth, inhibition of tissue growth, or any other desirable end-point. In one embodiment, a drug product, such as a growth-factor-containing polymer composition, such as a heparin-derivatized polyester composition comprising FGF-2, is combined with a second biocompatible polymer composition, such as a polyester composition as described herein, and is used as a biological scaffold for support of and/or propagation of tissue in a patient.

As shown below, functionalization of the polyester compositions described herein with maleate, results in a strong bioscaffold suitable for bone repair. Phosphorylation of the described polyesters also results in a highly promising composition for bone repair. Either composition or both compositions may be used for bone repair in a patient. Thus provided is a method of growing bone tissue in a patient comprising administering to a patient a polyester composition described herein, optionally derivatized with maleate, phosphate, or both, or a mixture of polymer compositions, optionally derivatized with maleate, phosphate, or both. The polymer composition can be injected or applied directly to a site in a patient to produce bone growth (e.g., repair of defects or traumatic injury). The composition may be molded into a desired shape prior to adminiatration to the patient. Active agents that promote bone growth may also be included in the composition, for instance by use of the heparin-derivatized polyester composition as described herein.

EXAMPLES

Aliphatic polyesters such as polylactide form an important class of biomaterial with controllable degradation and excellent biocompatibility. There have been extensive investigations on these biomaterials and many polyesters such as polyglycolide, polylactide, and other polyhydroxyalkanoates have been widely used as resorbable sutures, drug delivery matrices, and tissue-engineering scaffolds. Most of these polyesters are, however, semi-crystalline, hydrophobic, and lack free functional group(s) for further modification by biomolecules. One way to address these drawbacks is the introduction of functional groups. The presence of functionalizable groups such as hydroxyl and carboxylate in polyesters can efficiently increase their hydrophilicity and degradability, plus modulate their mechanical, thermal, chemical, and biologic. Furthermore, these functional groups provide access to versatile routes to conjugate a variety of bioactive molecules such as peptides, saccharides, and biotin. This can lead to novel biomaterials with diverse bioactivities. The reaction of pendant groups can further convert functionalizable linear polyesters to branched and network polymers, providing even more means to modulate their properties. Therefore, the properties of functionalized polyesters can be effectively tailored to meet a variety of demands in biomedical applications.

The state of the art in the synthesis of functionalizable polyesters has been well presented in several recent reviews (Lecomte P, et al. New prospects for the grafting of functional groups onto aliphatic polyesters. Ring-opening polymerization of alpha- or gamma-substituted epsilon-caprolactone followed by chemical derivatization of the substituents. Macromol Symp 2006; 240:157-65; Parrish B, et al. Strategies in Aliphatic Polyester Synthesis for Biomaterial and Drug Delivery Applications. ACS Symp Ser 2006; 939 (Degradable):248-66; Williams C K. Synthesis of functionalized biodegradable polyesters. Chem Soc Rev 2007; 36(10):1573-80; Taniguchi I, et al. Functional modification of biodegradable polyesters through a chemoselective approach: application to biomaterial surfaces. Polym Int 2006; 55(12):1385-97; and Jerome C., et al. Recent advances in the synthesis of aliphatic polyesters by ring-opening polymerization. Adv Drug Del Rev 2008; 60(9):1056-76). As mentioned in these reviews, chemical preparation of functionalizable polyesters is difficult because it usually involves a complex multistep synthetic route with a low overall yield. Two general strategies are used: one is pre-functionalization via polymerization of functionalized monomer; the other is post-polymerization functionalization via modification of non-functionalized polyester. The former usually requires complicated monomer preparation, and tedious protection and deprotection of functional groups. The latter often has to be performed under strict conditions and sometimes it is hard to control the final chemical structure. Moreover, both approaches are often associated with degradation in the transformation after polymerization.

In light of this, efficient synthesis of linear polyesters bearing suitable functionalities is highly valuable. We designed the title polymer according to three criteria. (1) Functionality: we chose the versatile hydroxyl group as the pendant functional group in the polymer. Hydroxyl group is one of the best understood organic functional groups, and many mild reactions are available for further modifications with biomolecules such as peptides. To minimize side reactions in subsequent biofunctionalization, hydroxyl group was designed to be the only functional group susceptible to further chemical modification. (2) Biocompatibility: this is required for the eventual application of any biomaterial. Thus, the resultant polymer and degradation products must be well tolerated by the cells and tissues. (3) Availability: this is important for widespread usage of the materials. Therefore, the principal polymer should be prepared from low-cost reagents by simple synthetic transformations in relatively fewer steps.

Poly(sebacoyl diglyceride) (PSeD) (FIG. 1) satisfies these design criteria. PSeD can be viewed as a linear analog of poly(glycerol sebacate) (PGS) (Wang Y D, et al. A tough biodegradable elastomer. Nat Biotechnol 2002; 20(6):602-6). PGS is synthesized directly by polycondensation of glycerol and sebacic acid and has a mixed structure: some of its secondary hydroxyl groups remain free and some are converted to ester groups that link two polymer chains. The distinct synthesis method of PSeD by an epoxide ring opening polymerization leads to a well defined polymer structure with free hydroxyl groups, which is important for control of subsequent functionalization with bioactive molecules. This versatile synthetic platform is applicable to other diglycidyl esters and diacids, which will lead to biodegradable and biofunctionalizable polymers with a variety of physiochemical properties.

The in vitro and in vivo biocompatibilities of PGS have been reported by multiple research groups and it is widely used in soft tissue engineering (Wang Y D, et al. Nat Biotechnol 2002; 20(6):602-6; Motlagh D, et al. 2006; 27(24):4315-24; Chen Q Z, et al. Biomaterials 2008; 29(1):47-57; Gao J, et al. J Biomed Mater Res A 2008; 85A(4):1120-8; Neeley W L, et al. Biomaterials 2008; 29(4):418-26; Radisic M, et al. Tissue Eng 2006; 12(8):2077-91; Sales V L, et al. Circulation 2007; 116(11):155-163; and Redenti S, et al. Biomaterials 2009; 30(20):3405-14). PSeD will likely have the same biocompatibility of PGS due to its structural relationship with PGS. To the best of our knowledge, common routes to synthesize polyesters by either polycondensation or ring-opening polymerization of lactones are not effective in the synthesis of linear polyesters with free functional groups without protection and deprotection steps. Glycerol-based polyesters prepared using direct chemical or lipase-catalyzed polycondensation are usually compromised by premature crosslinking, large polydispersity index (PDI), or low molecular weight. In the present synthetic strategy, glycidyl groups serve as both the active polymerization functionality and the precursor of the glyceryl moiety. Thus, the ring-opening polymerization would form the polyester backbone and the pendant hydroxyl groups in one step; as an added advantage, the reaction would not produce small molecule byproducts.

Example 1

A Biocompatible Polyester with Pendant Hydroxyl Groups

Here we present a simple route to prepare a linear polyester, poly(sebacoyl diglyceride) bearing pendant hydroxyl groups. The key monomer, diglycidyl sebacate, was prepared via direct esterification of glycidol with sebacoyl chloride under mild conditions. Subsequently sebacic acid opens the epoxy rings of diglycidyl sebacate to produce poly(sebacoyl diglyceride) (Mn=16.6 kDa, PDI=2.5) with an excellent yield (90%). The resultant polymer was characterized by NMR, FTIR, DSC, and TGA. MTT assay using primary baboon smooth muscle cells demonstrated its in vitro biocompatibility. This synthetic strategy can provide a versatile platform to a family of biodegradable, functionalized polymers with tunable physiochemical and biological properties useful for a wide variety of biomedical applications.

Materials and Equipment—Sebacoyl chloride (TCI America, 90%) and glycidol (Acros, 96%), were distilled under reduced pressure. Triethylamine (Alfa Aesar, 99%) was dried by anhydrous NaOH and distilled. Anhydrous solvents toluene, dioxane, and N,N-dimethylformamide (DMF), were purchased from EMD. Ethyl ether, ethyl acetate, and acetone were purchased from PHARMCO-AAPER. All solvents were used without further purification. Sebacic acid (Alfa Aesar, 98%) was recrystallized three times from 95% ethanol and dried under vacuum. Tetrabutylammonium bromide (Acros, 99+%), maleic anhydride (Alfa Aesar, 99%), Boc-Gly-OH (Peptides International), N,N'-Dicyclohexylcarbodiimide (DCC) (Alfa Aesar, 99%), and dimethylaminopyridine (DMAP) (99%, Avocado Research Chemicals Ltd) were used without further purification.

All compound characterization was carried out at ambient temperature. The molecular weight was determined via gel permeation chromatography (GPC) on a Viscotek GPCmax VE2001 system. For PSeD, the measurement was performed on a Viscotek organic I-MBMMW-3078 column and a VE3580 differential refractive index using DMF as the eluent. Polystyrene (Varian EasiVial PS-M, Part No. 2010-0301) was used for calibration. For PSeD glycinate and maleic monoester, the measurement was performed on a PSS SDV 1000 Å column and a Viscotek 270 dual detector (differential refractive index and right angle light scattering) using THF as the eluent. Polystyrene (American polymer standards PS170K) was used for calibration. $^1$H NMR spectra were recorded on a Varian Mercury-400 NMR in deuterated chloroform solution with tetramethylsilane as the internal chemical reference unless otherwise specially noted. $^{13}$C and 2D NMR spectra were recorded on a Bruker Avance 600 NMR. Fourier transformed infrared (FTIR) spectra were recorded on a Thermo Nicolet IR-100 spectrometer via sample films coated on NaCl crystal windows unless noted otherwise. Differential scanning calorimetry (DSC) and thermal gravimetric analysis (TGA) were performed on Seiko DSC 220C and TG/DTA 320 instruments, respectively, at a heating rate of 10° C./min under a nitrogen atmosphere.

Preparation of monomer diglycidyl sebacate—Sebacoyl chloride (11.37 g, 47.6 mmol) was added dropwise to a solution of glycidol (7.8 ml, 116.9 mmol) and triethylamine (31.5 ml, 224.1 mmol) in 180 ml of anhydrous toluene cooled in an ice/ethanol bath (−15° C.) under a nitrogen atmosphere over 30 min. The reaction mixture was stirred for another 6 h before it was filtered and concentrated. The residue was purified by flash chromatography on silica gel (3:1 hexane:ethyl acetate) to afford diglycidyl sebacate (10.4 g, 70% yield) as a white solid. $^1$H NMR (400 MHz, CDCl$_3$, Me$_4$Si) δ 4.42 (dd, J=12.6, 3.0 Hz, 2H), 3.91 (dd, J=11.8, 6.2 Hz, 2H), 3.19-3.23 (m, 2H), 2.85 (t, J=4.4 Hz, 2H), 2.65 (dd, J=5.2, 2.4 Hz, 2H), 2.35 (t, J=7.8 Hz, 4H), 1.60-1.65 (m, 4H), 1.25-1.31 (m, 8H).

Synthesis of PSeD—Diglycidyl sebacate, an equimolar amount of sebacic acid, and a catalytic amount of tetrabutylammonium bromide were mixed and dissolved in anhydrous DMF or dioxane in a Schlenk flask in a glove box filled with nitrogen. The flask was sealed, transferred out of the glove box, and connected to a Schlenk line. The flask was heated and its contents were stirred under a nitrogen atmosphere. The reaction mixture was purified via dilution in ethyl acetate, precipitation in ethyl ether, and dried under a vacuum at ambient temperature overnight. (See Table 1 for variations of the reaction parameters)

Functionalization of PSeD Using the —OH Groups

PSeD glycinate—PSeD (118.9 mg, 0.460 mmol), Boc-Gly-OH (88.7 mg, 0.506 mmol), DCC (189.9 mg, 0.921 mmol), and DMAP (2.81 mg, 0.023 mmol) were dissolved in anhydrous dichloromethane (8 ml). The mixture was stirred at room temperature under a nitrogen atmosphere for 18 h, before it was filtered and the filtrate was concentrated. The raw product was redissolved in acetone, precipitated using ethyl ether and washed with deionized water. The precipitate was dried to furnish PSeD glycinate (155 mg) as a colorless solid.

PSeD maleic monoester—PSeD (262.3 mg, 1.015 mmol) and maleic anhydride (199.1 mg, 2.031 mmol) were dissolved in 0.46 ml of anhydrous DMF in a Biotage 0.5-2 ml microwave vial and sealed in a glove box filled with nitrogen. The vial was transferred out of the glove box and reacted at 110° C. for 30 min using a Biotage Initiator 2.5 microwave reactor. The reaction mixture was precipitated in H$_2$O (18 Mohm-cm) and dried under vacuum at ambient temperature overnight to obtain the maleic monoester of PSeD (292.9 mg) as a transparent solid.

Crosslinking of PSeD and the mechanical properties of the resultant elastomer—A mixture of PSeD and sebacic acid (1.13 wt. %) was melted and poured into an aluminum mold coated with hyaluronic acid (mold release). The mixture was heated at 120° C. for 20 h to remove all the bubbles, then subjected to vacuum (1.1 Torr) at 120° C. for another 21 h to yield crosslinked PSeD elastomer.

Tensile strength testing was conducted on an MTS insight mechanical analyzer equipped with a 50 Newton load cell according to ASTM standard D142-06a. Three dog bone-shaped samples (D142-06a die A design scaled by 1/4, 14.75 mm×3 mm×1.3 mm, length×width×thickness) were tested and averaged. Deflection speed was kept at 125 mm/min. In the simple tensile strength test, the sample was elongated to failure. In the cyclic tensile strength test, the sample was pulled to 50%, then allowed to recover to 1% before immediately stretched to 50% five times.

Evaluation of in vitro biocompatibility of PSeD—The wells of a tissue culture-treated polystyrene (TCPS) 24-well plate were coated with 80 µl of 1 g/l PSeD solution in MeOH (0.2 µm filtered). The plate was dried under vacuum overnight after evaporation of the solvent in air. Both the TCPS plate and the polymer-coated plate were sterilized by UV light for 30 min, then washed with 1 ml phosphate buffered saline three times and with 1 ml culture medium once with gentle shaking (20 rpm). Each well was seeded with 50,000 nonimmortalized smooth muscle cells (passage 12) isolated from the carotid arteries of 4-year-old male baboons (*Papio cyncephalus*) in 1 ml of MCDB 131 medium supplemented with 10% FBS, 1% L-glutamine, and 20 µg/ml gentamycin. The cells were incubated at 37° C. with 5% CO$_2$. Medium was exchanged every 2 days. The number of metabolically active cells was determined colorimetrically by the 3-(4,5-dimethylthiazol-2-yl)-2,5-diphenyltetrazolium bromide (MTT) assay according to a previously published protocol via absorption at 570 nm measured with a Molecular Devices SpectraMax M2/M2e Microplate Reader. Statistical analysis was performed using a two-tailed Student's t test. A p value of ±0.05 was considered statistically significant. All values are reported as mean±standard deviation. Both polymer wells and the control were imaged on day 3 using an inverted phase contrast microscope [Nikon TE-2000U (Melville, N.Y.) equipped with a 4 MP Diagnostics Spot Flex digital camera (Sterling Heights, Mich.)].

Results

Synthesis of PSeD—The first step of the synthesis was the preparation of the monomer—diglycidyl sebacate. Due to the high reactivity of the epoxide groups, our preliminary attempts, including Tl(OAc)$_3$-catalyzed transesterification, DCC/DMAP-mediated condensation, and the reaction between sodium sebacate and epichlorohydrin (Maerker G, Carmichael J F, Port W S. Glycidyl esters. I. Method of preparation and study of some reaction variables. J Org Chem 1961; 26:2681-8), led to complex reaction mixture and very low yields, and were therefore considered to be failures. Later, we prepared diglycidyl sebacate by epoxidation of diallyl sebacate, which was prepared via esterification of allyl alcohol and sebacic acid (Gumera C B, et al. Adv Mater 2007; 19(24):4404-9). The yield was only approximately 60%, however, despite attempts to vary conditions such as reaction temperature, reaction time, and reactant ratio. Furthermore, excessive amounts of the oxidant m-chloroperoxybenzoic acid had to be used to accomplish the epoxidation. m-Chloroperoxybenzoic acid and its byproduct m-chlorobenzoic acid were difficult to remove completely and often led to lower purified yield (50%) in relatively large scale (2.6 g) reactions. Therefore, we explored the esterification of sebacoyl chloride by glycidol in toluene as a way to synthesize diglycidyl sebacate (FIG. 2). We found that the side reaction, ring-opening of the epoxide moiety by HCl, could be efficiently prevented using excessive triethylamine (5×) as an acceptor of HCl and lowering the reaction temperature to −15° C. No ring-opened byproducts were observed in the $^1$H NMR spectra of the reaction mixture. The purification was convenient because the byproduct, triethylamine hydrochloride, was only sparingly soluble in toluene and could be removed by a simple filtration. Under optimized conditions, diglycidyl sebacate was produced at 70% purified yield on a 10-g scale.

The second step of the synthesis was the epoxide ring-opening polymerization between diglycidyl sebacate and sebacic acid to yield PSeD. To minimize side reactions, we performed this reaction at relatively low temperature and, therefore, we chose solution polymerization instead of bulk polymerization because the melting point of sebacic acid is 132° C. Diglycidyl sebacate and sebacic acid were first polymerized in DMF without catalyst at 90° C. to produce PSeD (Table 1, entry 1). The resultant polymer had a moderate molecular weight (Mn=11.5 kDa) and a high PDI (6.5). Quaternary ammonium salts have been reported to be efficient catalysts for addition reactions of epoxy compounds (Nishikubo T, et al. Prog Polym Sci 1993; 18(5):963-95), so we hypothesized that they would be useful in our polymerization. When equimolar amount of diglycidyl sebacate and sebacic acid reacted in the presence of 3.4% $nBu_4NBr$ at 100° C. in dioxane (Table 1, entry 2), however, the catalyst induced gelation and the resultant polymer did not dissolve in common solvents such as $CH_2Cl_2$, THF, acetone, ethanol, and DMF. This indicated that the polymer was crosslinked Reducing the $nBu_4NBr$ concentration and lowering the reaction temperature successfully prevented crosslinking of the polymer (Table 1, entry 3); however, the resultant polymer had a high PDI (5.9). A more significant reduction in catalyst concentration and a slight elevation of reaction temperature [0.1% molar ratio $nBu_4NBr$ at 95° C. (Table 1, entry 4)] yielded PSeD with an increased molecular weight (Mn=16.6 kDa), a narrower polydispersity (PDI=2.5), and an excellent isolated yield (90%).

Figure 4A:
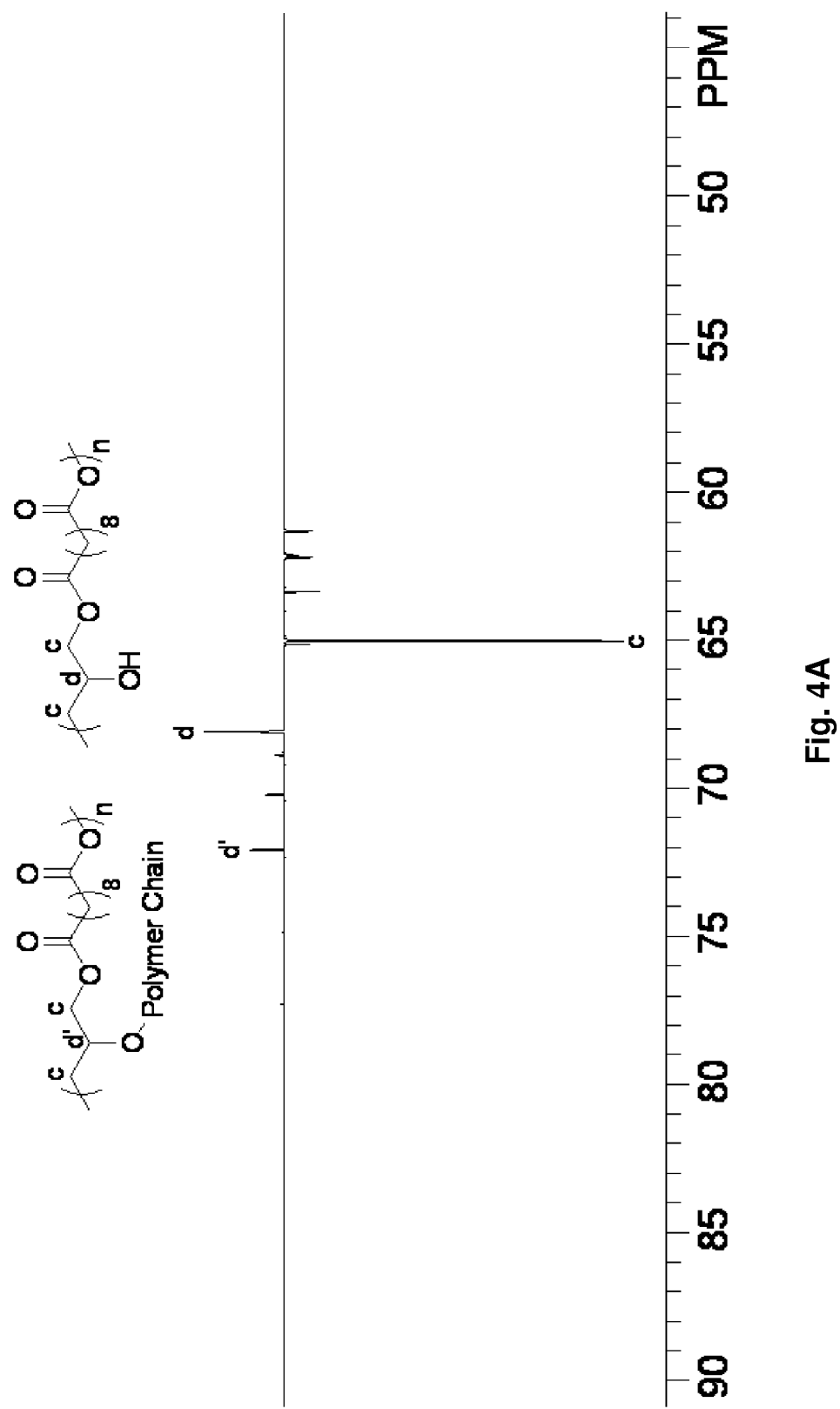
FIG. 4. (A) $^{13}$C DEPT 135 NMR spectrum of PSeD was used to distinguish the different carbons of PSeD. The positive peaks and negative peaks correspond to CH and $CH_2$ groups, respectively. (B) The $^1$H-$^{13}$C HETCOR NMR spectrum revealed the correlation of protons and carbons in PSeD. The strong peaks '*' represented most NMR signals of the glyceryl moiety, which displayed at the normal chemical shift region of a diglyceride and indicated a mostly linear structure of PSeD. The weak signal '#' revealed that the proton at 5.09 and 5.28 ppm was attached to the carbon at 72.06 ppm, which corresponded to the CH group of the glyceryl unit in the ester form (d'). (C) According to the relative chemical shifts and the results of $^{13}$C DEPT 135 and $^1$H-$^{13}$C HETCOR NMR spectra, the protons from 5.09-5.28 ppm were deduced to be the secondary hydrogen d', which corresponds to the triglyceride, branched part of PSeD. Thus, the relative integration (0.1) of protons from 5.09 to 5.28 ppm revealed the low crosslinking of PSeD (approximately 10%).
Figure 4B:
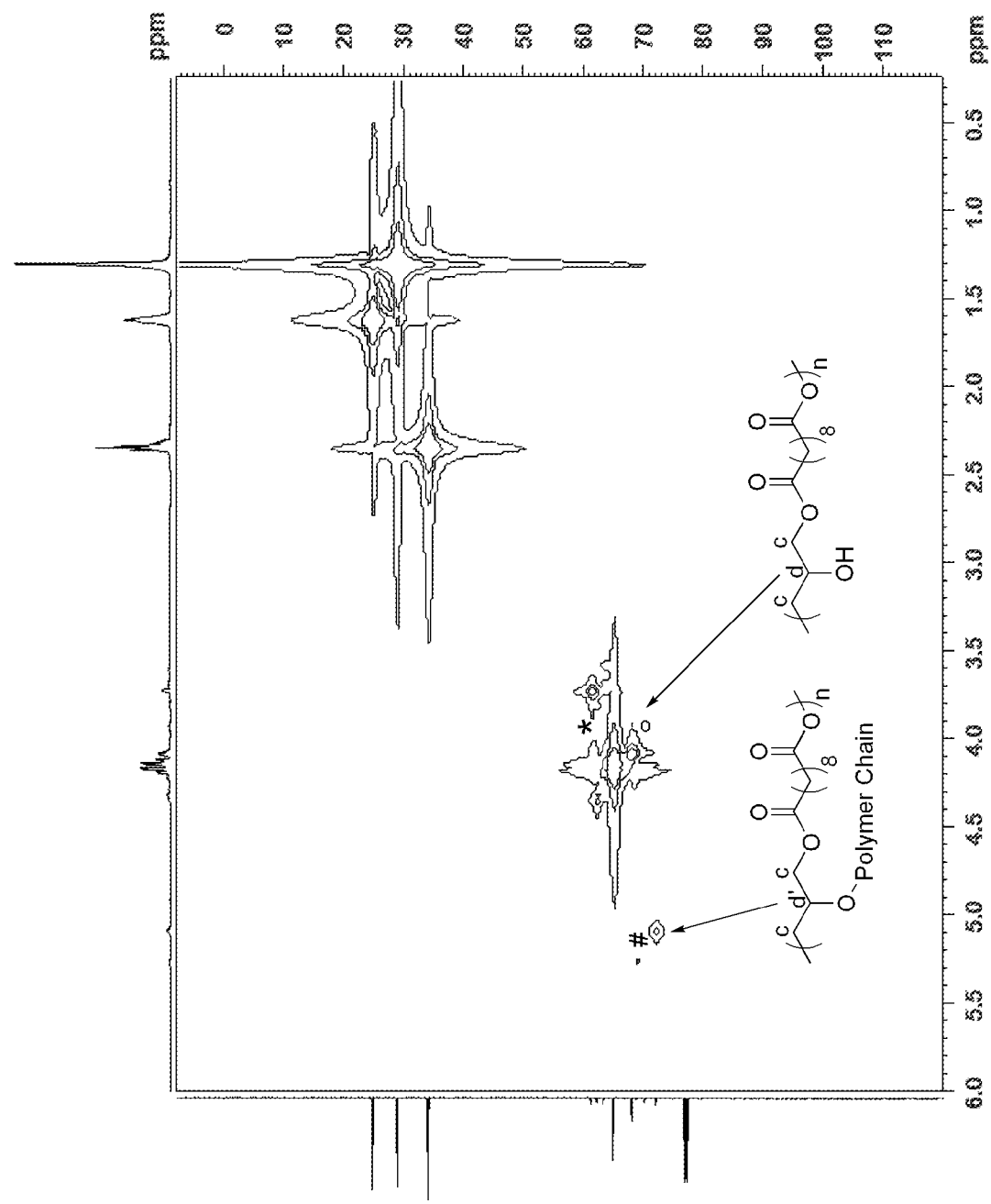
Figure 4C:
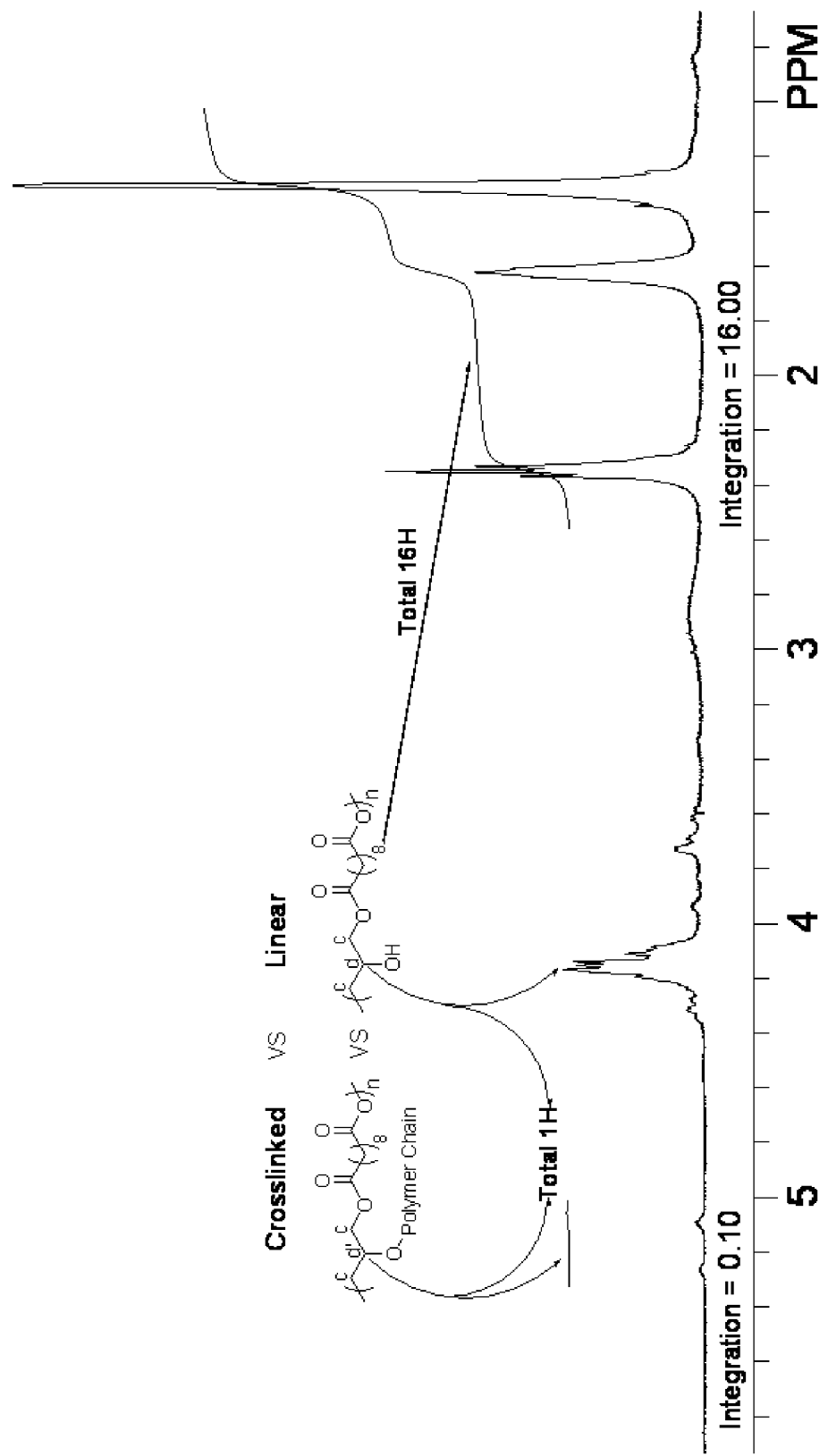

To examine the linearity of PSeD and the relative amount of free —OH groups, $^{13}C$ DEPT 135 (distortionless enhancement by polarization transfer) (FIG. 4A) and $^1H$-$^{13}C$ HETCOR (heteronuclear correlation) NMR experiments (FIG. 4B) were performed. In the $^{13}C$ DEPT 135 NMR spectrum (FIG. 4A), the glyceryl $CH_2$ groups (c) appeared as negative peaks and the CH (d) appeared as positive peaks. When glyceryl OH groups were converted to esters, their signals shifted downfield (d') because of the electron withdrawing effect of the carbonyl group. The intensity of d is much higher than that of d', indicating most of the —OH groups remain free. The $^1H$-$^{13}C$ HETCOR NMR spectrum (FIG. 4B) revealed that most of the proton signals of the glyceryl moiety appeared around δ 4.00 ppm (strong peaks marked with an *). The weak proton signal at 5.09 ppm (#) was associated with the carbon at 72.06 ppm (d'), a negative peak in the DEPT 135 NMR spectrum indicating a glyceryl CH group. Furthermore, the downfield chemical shift of the # peak suggested that it was an ester CH group (d'). The higher intensity of the d signal vs. d' again indicated the linear diglyceride structure of PSeD and the fact that most of the hydroxyl groups are free. A ratio of the free glyceryl OH groups vs. glyceryl ester group was estimated using $^1H$ NMR. We set the proton integration of sebacoyl moiety (δ 1.31, 1.62 and 2.35 ppm) as 16 protons and the integration of the CH group (d+d') in glyceryl moiety as 1 proton (FIG. 4C), which corresponded to one PSeD repeating unit. The resulting integration of 0.1 for the glyceryl ester moieties (δ5.09 to 5.28 ppm, d', FIG. 3C), representing the branched PSeD, corresponded to approximately 10%. In summary, about 90% of the glyceryl hydroxyl groups in PSeD are free, that is, PSeD is approximately 90% linear,

TABLE 1

Optimization of polymerization between diglycidyl sebacate and sebacic acid.

| Entry | $nBu_4NBr$ | Solvent | Temperature | Time | Mn | PDI | Yield[a] |
|---|---|---|---|---|---|---|---|
| 1 | none | DMF | 90° C. | 50 h | 11.5 kDa | 6.5 | 60% |
| 2 | 3.4 mol % | Dioxane | 100° C. | 114 h[b] | Crosslinked | — | 75% |
| 3 | 1.4 mol % | Dioxane | 80° C. | 160 h[b] | 12.7 kDa | 5.9 | 78% |
| 4 | 0.1 mol % | Dioxane | 95° C. | 174 h | 16.6 kDa | 2.5 | 90% |

[a]Unoptimized.
[b]The final reaction mixture formed a resin and could not be stirred.

Figure 3B:
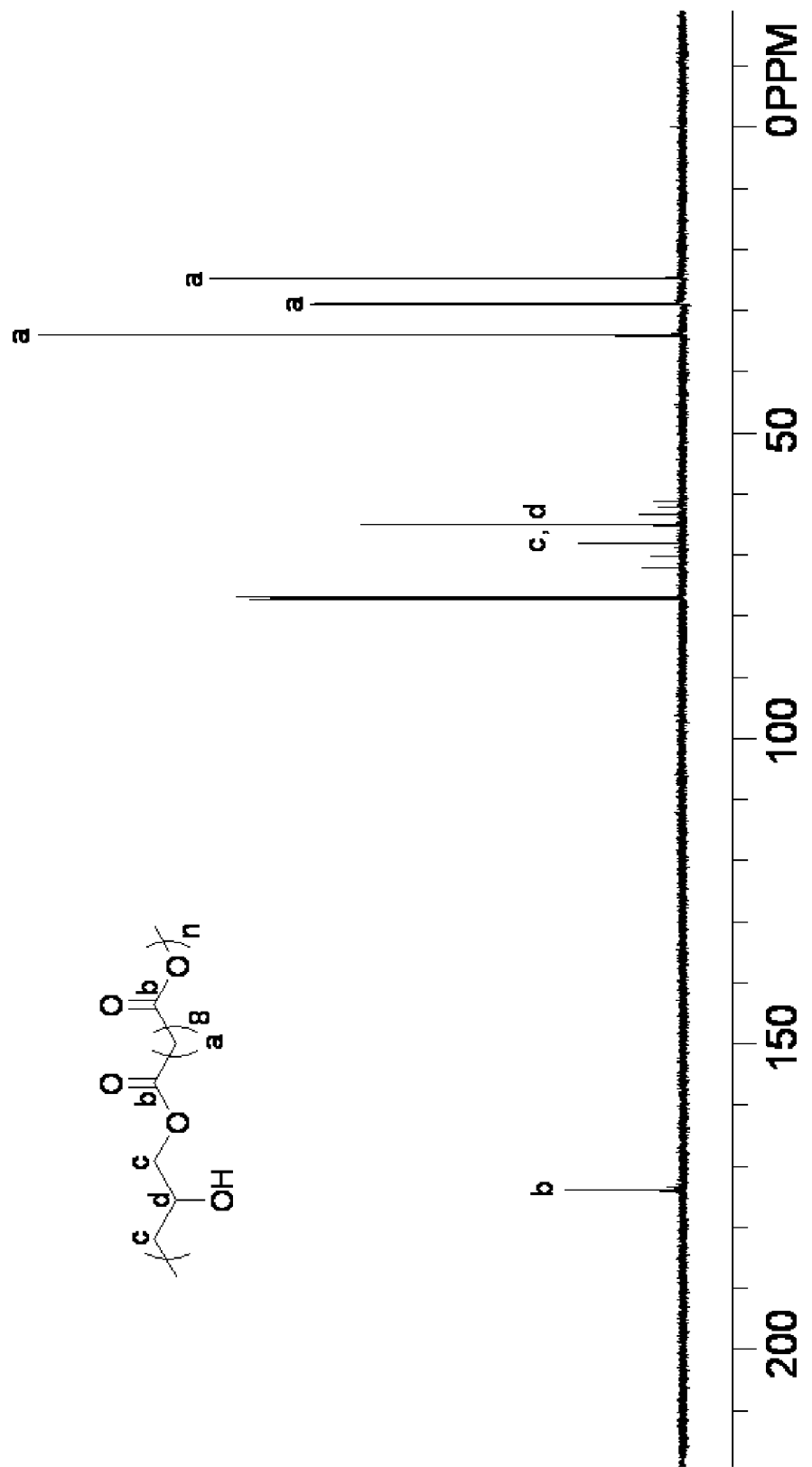

Structural Characterization of PSeD—The polymer was characterized by standard analytical methods. Its structure was analyzed by FT-NMR and MR spectroscopy. In the $^1H$ NMR spectrum (FIG. 3A), the three signals marked 'a' at δ 1.31, 1.62 and 2.35 ppm were ascribed to the sebacoyl moiety in the polymer backbone. The broad peak marked 'b' at δ 2.89 ppm indicated the presence of a hydroxyl group (—OH). The signal at chemical shift 3.55-4.54 ppm marked 'c, d' corresponded to the CH protons of the glyceryl moiety. Comparison of the integrations of the various protons suggested that each polymer repeating unit consisted of one —OH group. Moreover, it revealed that essentially all the epoxide functionalities had been consumed because no proton signals associated with epoxy groups (δ around 3.0 ppm, please see the NMR data of diglycidyl sebacate in the experimental section) were observed. The $^{13}C$ NMR spectrum of PSeD (FIG. 3B) further confirmed its structure. The three signals marked 'a' at δ 24.78, 28.95 and 34.05 ppm were attributed to the sebacoyl moiety in the backbone of the polymer. The signals at chemical shifts 61.31 and 72.08 ppm marked 'c, d' were attributed to the carbons of glyceryl moiety. The signal marked 'b' at δ 173.94 ppm corresponded to carbon of the ester group.

Figure 5:
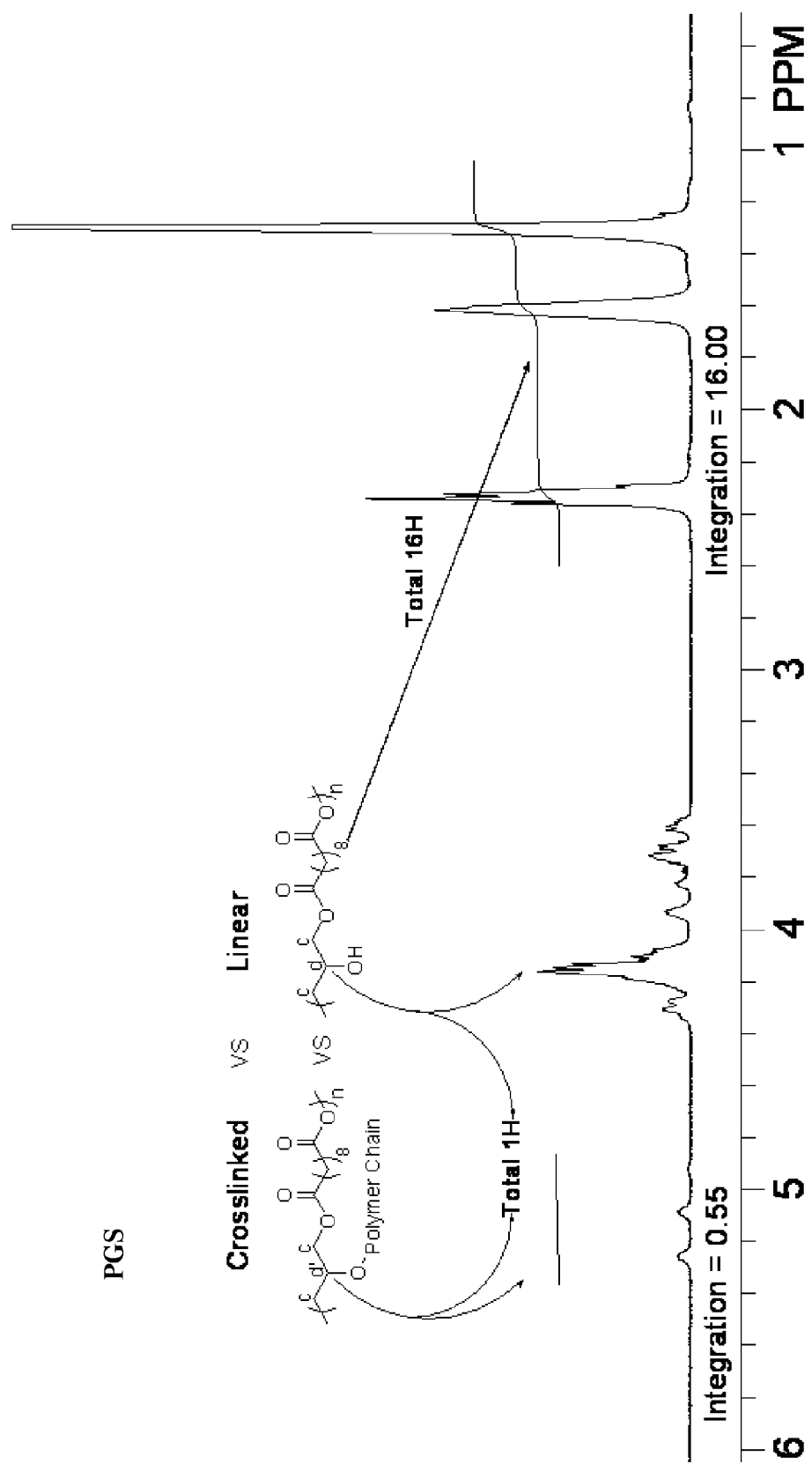
FIG. 5. The $^1$H NMR spectrum of PGS. The relative integration of d' vs. d protons indicated a higher degree of crosslinking (approximate 55%) than seen with PSeD.

10% branched. A similar analysis of PGS revealed that only 45% of the hydroxyl groups are free (see FIG. 5).

Figure 6:
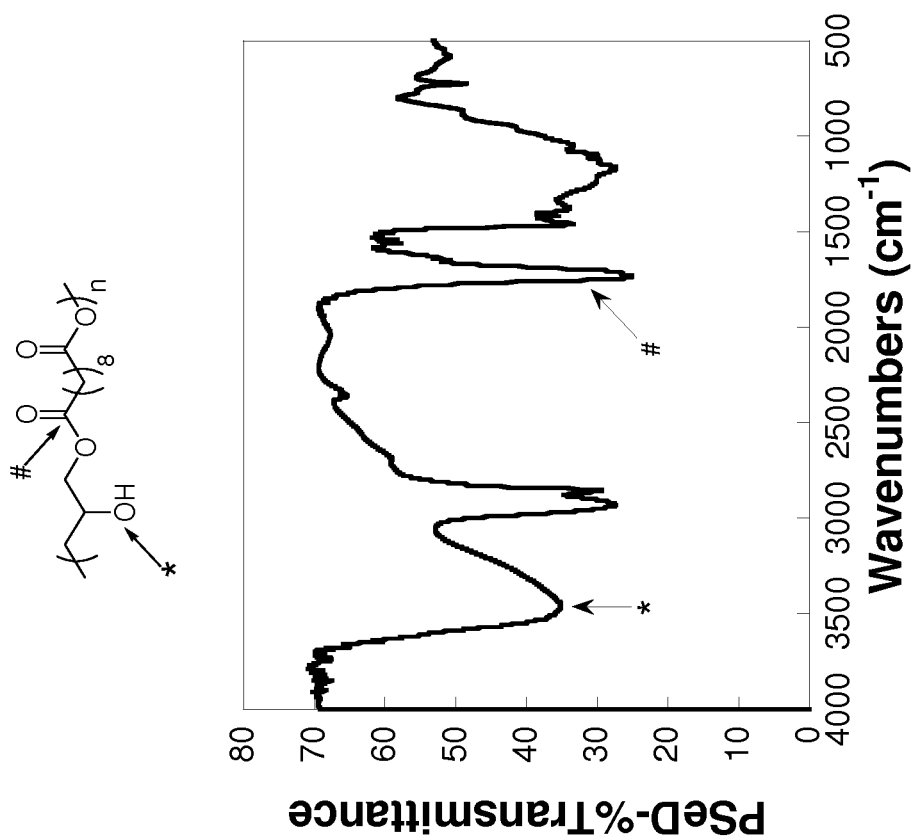
FIG. 6. The FTIR spectrum of PSeD displayed the signal of expected functionalities: O—H bonds at 3461 cm$^{-1}$ and ester C=O bonds at 1740 cm$^{-1}$.

The characteristic functional groups of PSeD were corroborated by FTIR investigation (FIG. 6). The ester bond in the backbone and the presence of hydroxyl groups on the side chain showed a sharp, intense C=O stretch at 1740 $cm^{-1}$ and a broad, intense O—H stretch at 3461 $cm^{-1}$, respectively.

Physical properties of PSeD and PGS prepolymer—In order to compare PSeD with PGS prepolymer synthesized by direct polycondensation of glycerol and sebacic acid, we prepared PGS prepolymer as previously reported (Gao J, et al. Tissue Eng 2006; 12(4):917-25) and characterized it under identical conditions as PSeD. The results are summarized in Table 2. The polymers' thermal properties were determined by DSC and TGA. Similar to PGS, the glass transition temperature ($T_g$) of PSeD was very low (<−100° C.), which suggested that, after curing, it would be an elastomer at ambient temperature. PSeD, however, showed higher melting ($T_m$) and crystallization ($T_c$) temperatures than PGS prepolymer. This was consistent with a linear structure for PSeD, different from the branched structure of PGS. Furthermore, the TGA experiment revealed that PSeD had a high decomposition temperature ($T_d$) at 382.9° C. and therefore, it could be used in a wide temperature range.

TABLE 2

Comparison of the properties of PSeD and PGS prepolymer.

| Compound | Mn (kDa) | PDI | Cross-linking (%)[a] | $T_m$ (° C.) | $T_c$ (° C.) | $T_g$ (° C.) | $T_d$ (° C.) |
|---|---|---|---|---|---|---|---|
| PSeD | 16.6 | 2.5 | 10 | 26.4, 52.3 | 1.2 | None[b] | 382.9 |
| PGS | 9.0 | 9.3 | 55 | −3.4, 15.0, 33.3 | −12.0 | None[b] | [c] |

[a]According to the analysis of NMR spectra. For PSeD please see FIG. 4C. For PGS please see FIG. 5.
[b]No glass transition temperature was observed above −100° C.
[c]Not measured.

PSeD was designed to be a versatile intermediate for further functionalization, so we tested its solubility in various solvents at ambient conditions. PSeD was soluble in most common organic solvents except those with low polarities (Table 3), which made it easy to be cast into various shapes and ready for further functionalization. It also indicated that the polymer had few crosslinks (Kumar A, et al. Macromolecules 2003; 36(22):8219-21 and Kallinteri P, et al. Biomacromolecules 2005; 6(4):1885-94). The polymer was insoluble in water, making it a candidate for a tissue engineering scaffold and various implantation applications. Moreover, PSeD can be stored for more than one year without significant change in solubility. In contrast, PGS became insoluble after storage under the same conditions for 3 months, likely due to crosslinking of the polymer. This improved property makes PSeD more amenable to practical use.

TABLE 3

Solubility of PSeD in various solvents.

| | Solvent[a] | | | | |
|---|---|---|---|---|---|
| | Hexane | Et$_2$O | CH$_2$Cl$_2$ | THF | CHCl$_3$ | Ethyl acetate |
| Solubility[b] | − | − | + | + | + | + |

| | Solvent[a] | | | | |
|---|---|---|---|---|---|
| | Dioxane | Acetone | MeOH | EtOH | DMF | H$_2$O |
| Solubility[b] | + | + | + | + | + | − |

[a]Ranked according to the polarity.
[b]−: insoluble; +: soluble

Figure 8B:
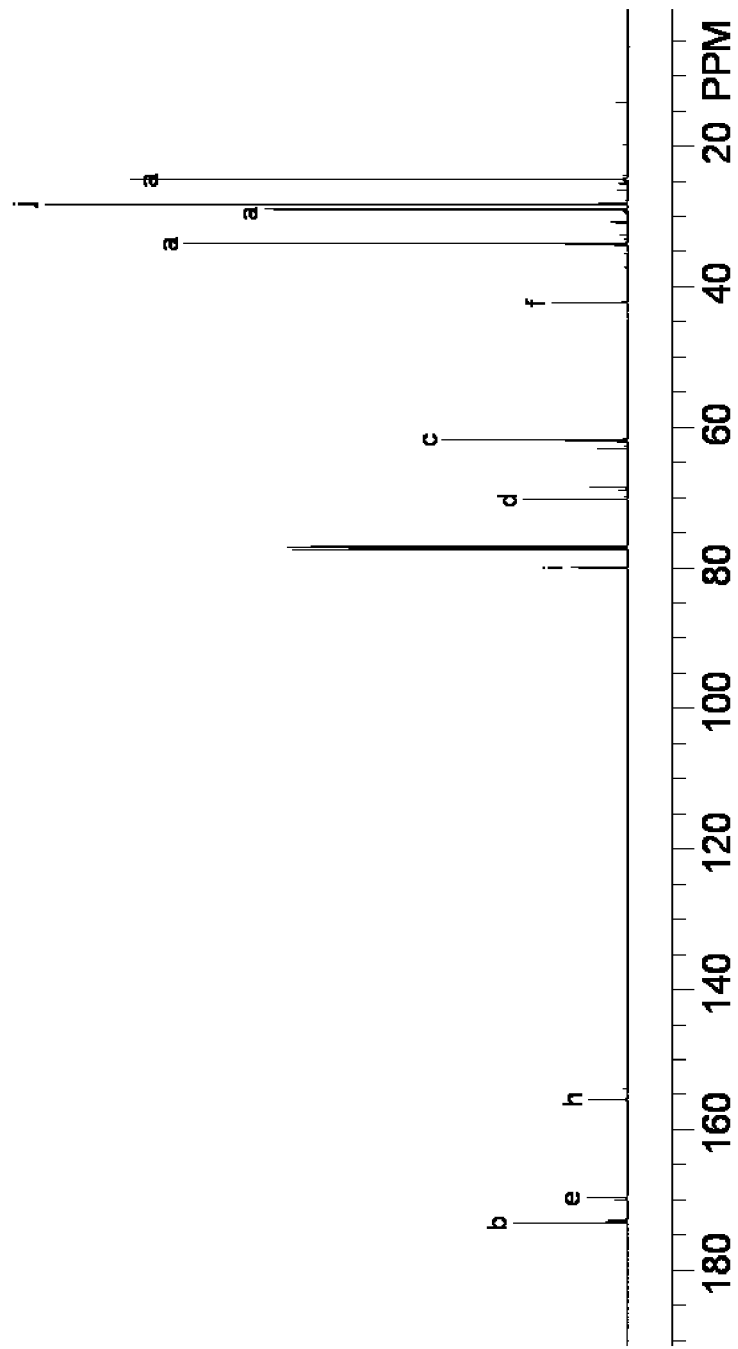
FIG. 8. Characterization of PSeD glycinate. (A) $^1$HNMR spectrum (600 MHz, CDCl$_3$) (B) $^{13}$C NMR spectra (600 MHz, CDCl$_3$). (C) FTIR-ATR spectrum (recorded on Thermo Nicolet IR iS10 spectrometer).
Figure 8C:
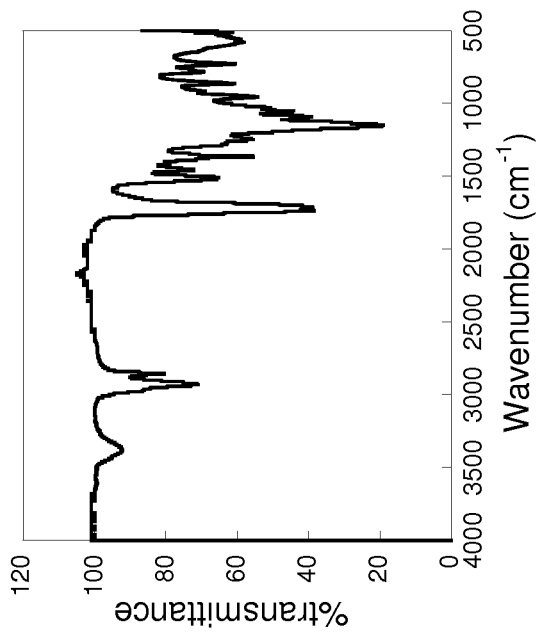

Functionalization of PSeD—To demonstrate the potential ability to use the —OH groups of PSeD for biofunctionalization, we investigated the coupling reaction between PSeD and glycine, a representative for biomolecules. PSeD readily reacted with N-tert-butoxylcarbonyl (Boc)-protected glycine in the presence of excess DCC and a catalytic amount of DMAP at room temperature to yield PSeD-glycinate (FIG. 7, Mn=25.1 kDa, PDI=1.4) with around 90% glycination (according to the relative integrations in $^1$HNMR spectrum; see FIG. 8).

Figure 9:
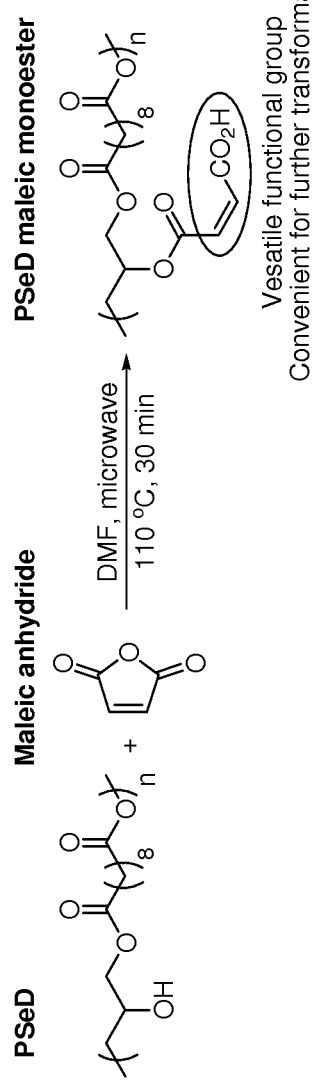
FIG. 9. A model reaction for further derivatization of PSeD. Maleic monoester derivative of PSeD was readily synthesized by microwave-assisted esterification, which yielded a polymer with free α, β-unsaturated carboxylic groups and provided more approaches to further functionalization.
Figure 10A:
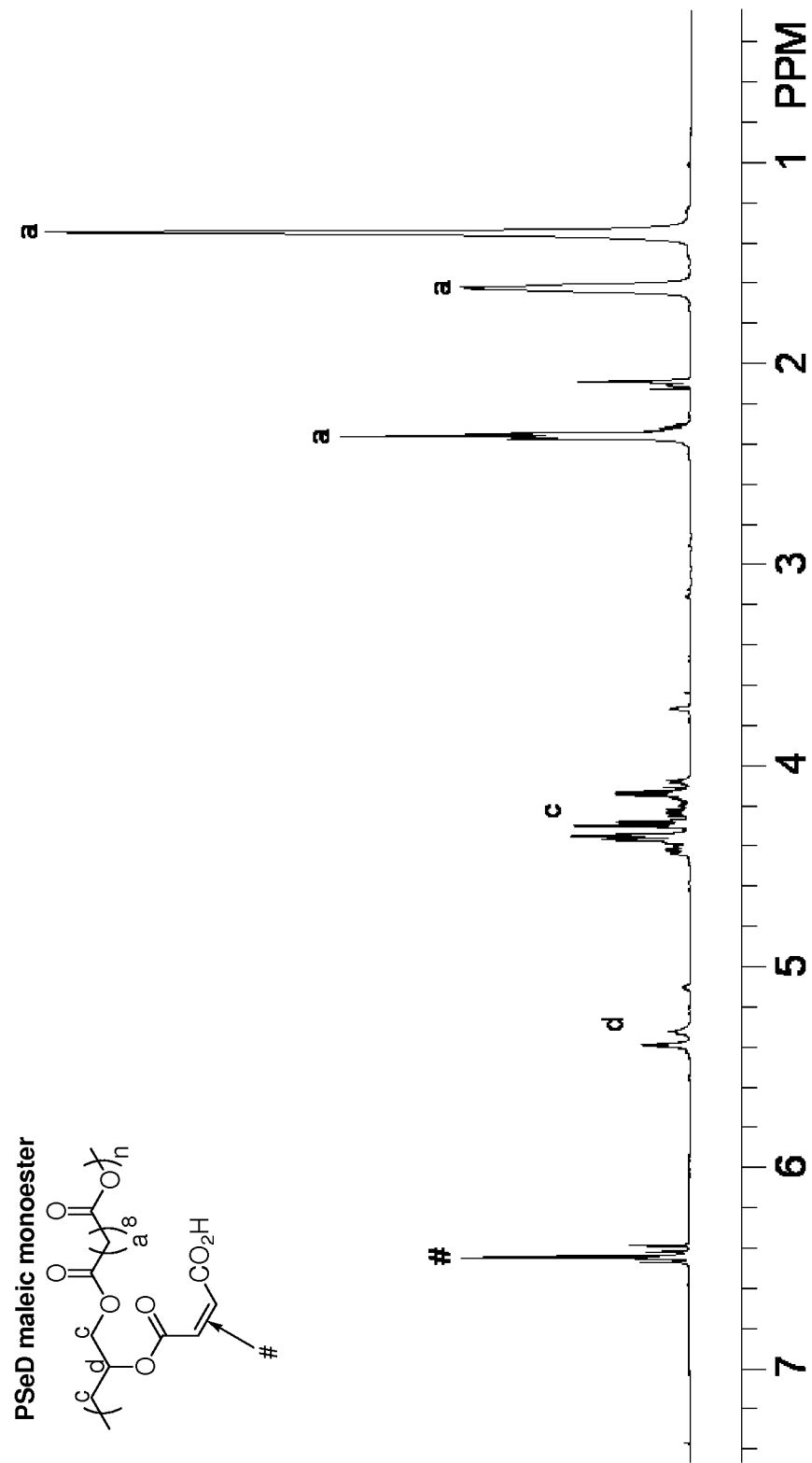
FIG. 10. Characterization of PSeD maleic monoester. (A) $^1$H NMR spectrum (600 MHz, acetone-d$_6$). (B) FTIR spectrum (recorded on Thermo Nicolet IR iS10 spectrometer using sample film coated on NaCl crystal windows). The signals of carbon-carbon double bond are marked as '#'.
Figure 10B:
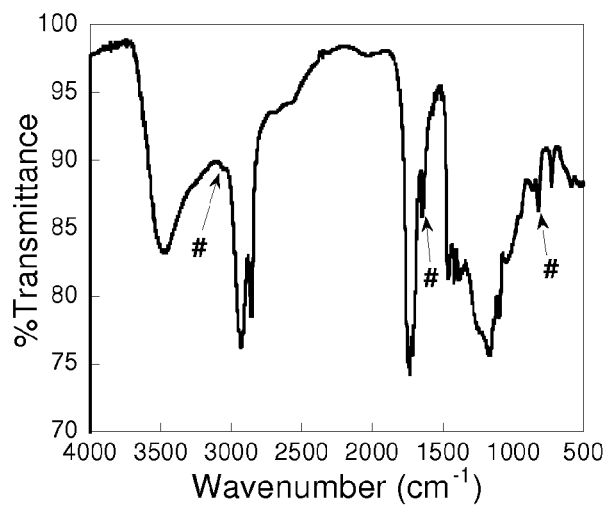

To further explore the potential of PSeD for derivatization and to illustrate the versatility of PSeD, we reacted PSeD with excess maleic anhydride at 110° C. in DMF by microwave-assisted esterification (FIG. 9). The reaction was performed for 30 min and produced PSeD-maleic monoester (Mn=20.3 kDa, PDI=2.0) with around 80% esterification (according to the relative integrations in $^1$HNMR spectrum; see supplementary data FIG. 10).

Figure 11A:
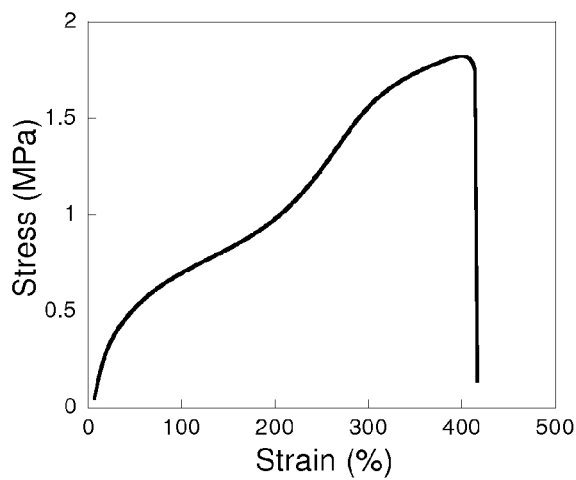
FIG. 11. Typical tensile stress vs. strain curve of cured PSeD elastomer. (A) Simple tensile test to failure. (B) Cyclic tensile test at 50% for 5 cycles. Note the reversibility of the deformation after the first cycle.
Figure 11B:
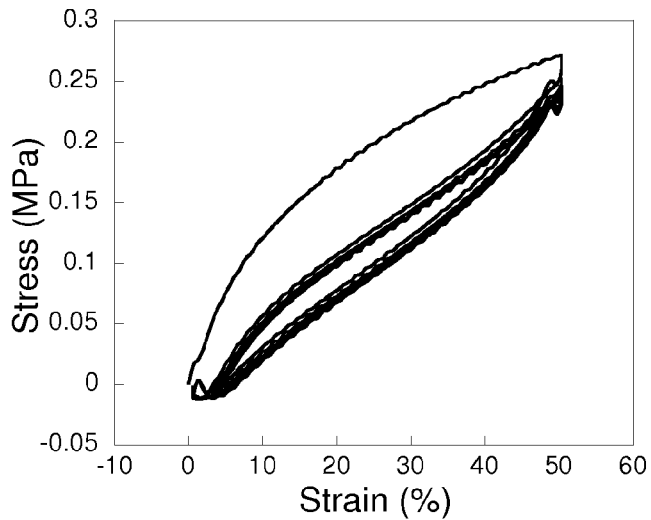

Curing PSeD and the mechanical properties of the resultant elastomer—To keep crosslinking low and elasticity high for the final network, PSeD was cured with a small amount sebacic acid (1.1% by weight) under moderate vacuum at 120° C., Tensile tests of the cured PSeD revealed a stress-strain curve characteristic of an elastomeric and tough material (Table 4, FIG. 11A). The Young's modulus of the original linear region was found to be 1.57±0.48 MPa and the ultimate tensile stress was found to be 1.83±0.06 MPa. The elongation at break was up to 409±29%. Moreover, cyclic tensile testing was performed with 50% strain for 5 cycles (FIG. 11B). Only limited hysteresis was observed.

TABLE 4

Mechanical properties of cured PSeD and PGS.

| Elastomer | Young's modulus (MPa) | Tensile strength (MPa) | Elongation (%) |
|---|---|---|---|
| PSeD | 1.57 ± 0.48 | 1.83 ± 0.06 | 409 ± 29 |
| PGS[a] | 0.282 ± 0.025 | 0.5 | 267 ± 59.4 |

[a]Representative data of PGS is shown [1]. PGS and PSeD were cured via different mechanisms; the crosslinking density were both low, but unlikely to be identical.

Biocompatibility of PSeD—The biocompatibility of PSeD was tested by examining the metabolic activity of nonimmortalized baboon smooth muscle cells seeded onto PSeD-coated 24-well plates. TCPS was used as a control. The cells showed similar long spindle morphology on PSeD and TCPS (FIGS. 12A and B). Identical numbers of cells were seeded on all surfaces. From day 1 to day 3, MTT assays revealed a significantly higher number of metabolically active cells (P<0.05) on PSeD surfaces than on TCPS surfaces (FIG. 12C). On day 4, cells approached confluence on both PSeD and TCPS surfaces and there was no difference in cell number statistically. This demonstrated that PSeD was at least as cytocompatible as TCPS in vitro.

Discussion

Functionalized polyesters are promising new biomaterials because they add tunable biodegradability, physical, chemical, and biological properties to established polyesters such as polylactide and polyglycolide. The free functional groups allow facile modifications with biomolecules that lead to versatile biomaterials with controlled interactions with cells and tissues. Efficient synthesis of functionalizable polyesters is, however, still a major challenge that greatly limits the availability and widespread applications of biofunctionalized synthetic polyesters. Here we have presented a simple strategy to prepare functionalizable polyester with free hydroxyl groups. The epoxide ring-opening polymerization between a dicarboxylic acid and the corresponding diglycidyl ester produces the target functionalizable polyester in one step without the need for protection and deprotection (FIG. 1, Table 1). The synthetic strategy is versatile and can be used with other diacids and diepoxides to yield various linear functionalizable polyesters. Compared to other current approaches to functionalized polyester, it is simpler and more efficient.

PSeD exhibits several unique advantages over PGS prepolymer synthesized by polycondensation of glycerol and sebacic acid (Table 2): better defined structure with more free —OH groups and higher linearity (10% vs. 55% branching); higher molecular weight (16.6 kD vs. 9.0 kD); narrower polydispersity (2.5 vs. 9.3); and longer shelf time (>1 year vs. 3 months). In addition, the direct polycondensation for PGS requires higher temperature (120° C.) and vacuum (40 mTorr) to remove H$_2$O and accelerate the reaction. PSeD synthesis proceeds at lower temperature (95° C.) with no need for vacuum to remove small molecule byproducts (FIG. 1).

The more defined structure of PSeD provides a suitable platform for further biofunctionalization. We selected glycine as the representative for biomolecules. The DCC coupling reaction ran smoothly and produced PSeD glycinate in high yield. Since many biomolecules, such as amino acids, peptides, proteins, glycans, and biotin contain free carboxylates, the reaction described here (FIG. 7) would serve as an effective bioconjugation route for PSeD. In addition, microwave-assisted esterification with maleic anhydride provides PSeD maleic monoester with good purity and yield (FIG. 9). This is a much more efficient synthetic route than a similar coupling reaction reported between hydroxylated polyester and succinic anhydride (reaction time: 30 min vs. 10 days) (Noga D E, et al. Biomacromolecules 2008; 9(7):2056-62). The free α, β-unsaturated carboxylic acid groups in PSeD-maleic monoester can easily react with a biomolecule through esterification, amidation, Michael addition, and photo-crosslinking (Noga D E, et al. Biomacromolecules 2008; 9(7):2056-62; Hersel U, Dahmen C, Kessler H. RGD modified polymers: biomaterials for stimulated cell adhesion and beyond. Biomaterials 2003; 24(24):4385-415; Jiao Y P, Cui F Z. Surface modification of polyester biomaterials for tissue engineering. Biomedical Materials 2007; 2(4):R24-R37; and Ifkovits J L, Burdick J A. Review: Photopolymerizable and degradable biomaterials for tissue engineering applications. Tissue Eng 2007; 13(10):2369-85). This further enriches the variety of chemistry that can be performed to functionalize PSeD to obtained biomaterials with unique mechanical and biological properties.

For applications in tissue engineering, biomaterials that mimic the mechanical aspect of native extracellular matrix by transducing mechanical stimuli to cells and tissues may be advantageous. Since many soft tissues such as blood vessels and lungs are elastic, several biodegradable elastomers have been developed. Among them, crosslinked elastomers made from aliphatic polyesters have received much attention recently. They show good biocompatibility and biodegradability. Their mechanical properties are in the range of soft tissues and they primarily degrade by surface erosion, retaining their structural integrity and mechanical stability during degradation in vivo. Most crosslinked polyester elastomers are typically synthesized by random polycondensation. This method produces prepolymers with relatively low molecular weight, high polydispersity, undefined branched structure, and are prone to premature crosslinking. This compromises the mechanical properties of the elastomer. Various approaches from several different laboratories have been used to improve the mechanical properties of PGS; these include modulating monomer feeding ratios, curing conditions, and crosslinking reagents (Chen Q Z, et al. Characterisation of a soft elastomer poly(glycerol sebacate) designed to match the mechanical properties of myocardial tissue. Biomaterials 2008; 29(1):47-57; Nijst C L E, et al. Biomacromolecules 2007; 8:3067-73; Liu Q Y, et al. J Appl Polym Sci 2005; 98(5):2033-41; Liu Q Y, et al. J Appl Polym Sci 2007; 104 (2):1131-7; and Liu Q Y, et al. Biomedical Materials 2009; 4(2):9), and all of these relied on polycondensation as the synthetic method. Consequently, the resultant polymers have mechanical properties very similar to the original PGS. We hypothesized that polymeric networks produced by crosslinking linear functionalized polyester with higher molecular weight and narrower polydispersity would provide more elastic materials than their counterparts obtained by direct polycondensation. Accordingly, we investigated the crosslinking of PSeD with sebacic acid to produce a biodegradable elastomer that would be structurally related to PGS. The motivation was to maintain the good biocompatibility of PGS while improving its mechanical properties. As illustrated herein, sebacic-acid cured PSeD demonstrated a much tougher (approximately 5 times greater area under curve) and more elastic properties than cured PGS (Table 4, FIG. 11): 5 times higher Young's modulus; >3 times higher tensile strength; and greater maximum strain at break. It therefore resembles bovine ligament elastin mechanically (tensile strength and Young's modulus of 2 MPa and 1.1 MPa, respectively (Gosline J, et al. Philos Trans R Soc Lond B Biol Sci 2002; 357(1418):121-32)). The strain at break was higher than that of most soft tissues (for examples, arteries and veins can be elongated up to 260% (Lee M C, et al. J Biomech 1992; 25(8):925-7)). To the best of our knowledge, the elongation at break of the cured PSeD is one of the highest among crosslinked polyester elastomers used in biomedical applications. In addition, the cyclic tensile test revealed the elastomer's ability to recover from deformations (FIG. 11B), indicating that it is suitable for applications in a mechanically dynamic environment. Moreover, the mechanical properties of PSeD can be further modulated via controlling curing conditions and selecting different types and amount of crosslinking reagents (data not shown).

Figure 12:
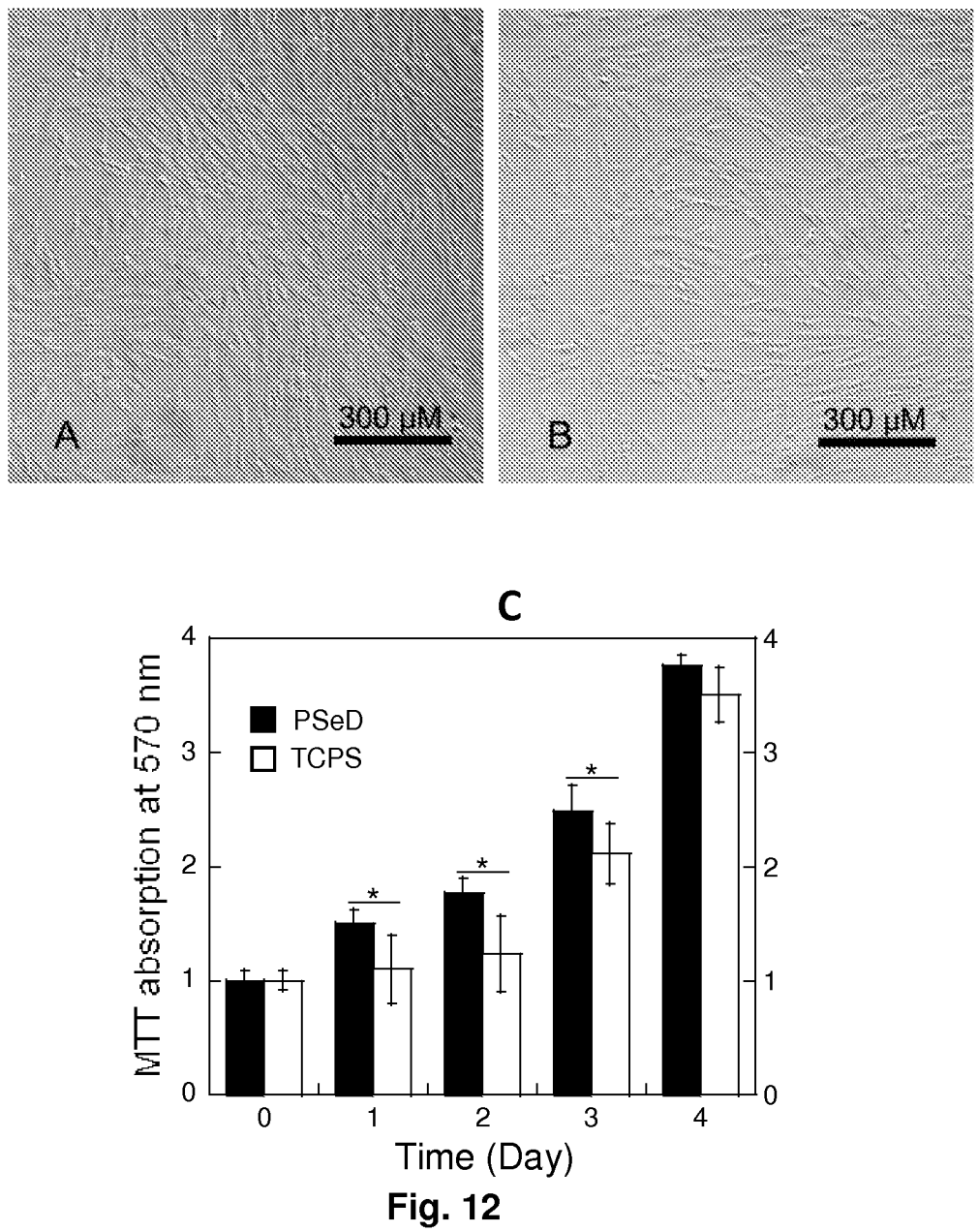
FIG. 12. Baboon smooth muscle cells cultured on PSeD surface exhibited normal morphology, similar to that on TCPS. Representative phase contrast photomicrographs of baboon smooth muscle cells at day 3 after seeding in PSeD-coated wells (A) and TCPS wells (B) (magnification 100×, scale bar=300 μm). (C) MTT assay of baboon smooth muscle cells in PSeD wells and TCPS wells showed that there were more metabolically active cells on PSeD than on TCPS in the first three days. Data represent mean±SD. * Statistical significance (p<0.05). Normalized values shown.

The in vitro cytocompatibility of PSeD was evaluated by monitoring metabolic activities of nonimmortalized baboon smooth muscle cells seeded on PSeD surfaces. Examination of the morphology of cells and the number of metabolically active cells on PSeD film suggested that cells on PSeD surfaces proliferate at least as well as those on TCPS surfaces (FIG. 12). This suggests that PSeD may be suitable for many biomedical applications including tissue engineering, wound healing, and drug delivery. We are currently investigating the in vivo biocompatibility of PSeD.

PSeD and PGS exhibit several $T_m$ values and one distinct Tc in their thermograms. This could be caused by melt-recrystallization during the DSC heating cycle. The polymer was first heated from room temperature to 100° C., and then cooled to −100° C. before being heated again. Cooling of the polymer might yield a less thermodynamically stable form. Upon heating the crystalline domains melted and the molten polymers recrystallized into a more stable form that subsequently melted. Because the two melting transitions were adjacent to each other, a distinct Tc was not observed. We are investigating possible deconvolution of the transitions using advanced software to further characterize the thermal behavior of the polymer.

Thus, a functionalizable polyester bearing free hydroxyl groups was designed and successfully synthesized in two simple steps from commercially available starting materials. The synthetic route is practical, featuring easily synthesized monomers, mild polymerization conditions, and no protection and deprotection steps. The usefulness of this approach has been demonstrated by the tougher and more elastic nature of the cured polymer as compared to the first generation PGS, and the ready functionalization with glycine. The enhanced mechanical properties and easy derivatizations of PSeD were enabled by virtue of its more defined polymer structure than that of PGS. Initial evaluation using nonimmortalized cells showed PSeD to be cytocompatible in vitro. The synthetic strategy is general and can be used to synthesize other glycerol-based linear polyesters. We are currently investigating modification of PSeD with oligopeptides, optimizing the curing conditions, and expanding the application of this synthetic platform to other diacids. We expect this new design platform will lead to a diverse family of biodegradable and bioactive polymers with versatile mechanical, physical, chemical, and biological properties tailored for a wide range of biomedical applications.

Example 2

A Reversible Photo-Crosslinked Polymeric Network

Figure 13:
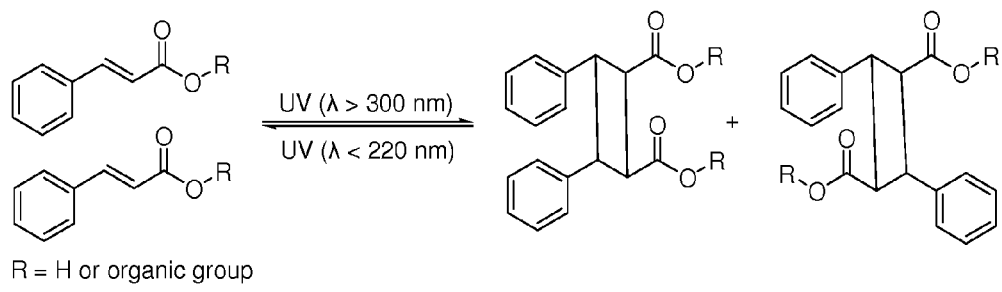
FIG. 13. Cinnamate can dimerize under UV light (λ>300 nm) and the cyclodimer can regenerate the starting monomer upon UV light (λ<220 nm).

[2+2] photocycloadditions of olefinic compounds have been invesitigated extensively and have become a useful tool for organic molecular design. For example, the cyclodimerization of cinnamic acid is one of the oldest and best known reactions of solid-state photochemistry (FIG. 13). Interestingly, this reaction is reversible when the dimer is exposed to UV light of short wavelength (FIG. 13). However the usefulness of this photo-reversible cycloaddition reaction has been seldom investigated in polymeric system. We hypothesize that attachment of cinnamate group to a polymer backbone will result in a novel polymer capable of photo-reversible crosslinking.

Figure 14:
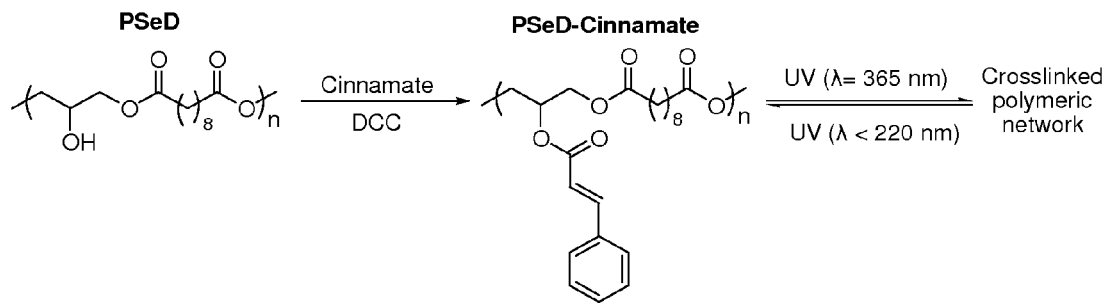
FIG. 14. A representative reversible photo-crosslinkable polymer system: PSeD-Cinnamate.
Figure 15:
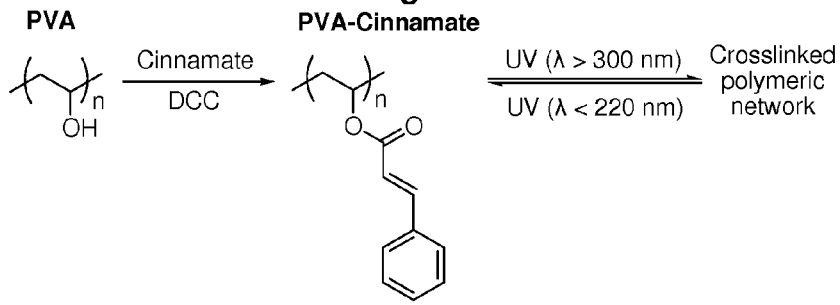
FIG. 15. Another example of reversibly photo-crosslinkable polymer system: PVA-Cinnamate.

To initially demonstrate the above conceptual design, currently we are investigating poly(sebacoyl diglyceride) (PSeD) cinnamate (FIG. 14). PSeD is biocompatible and biodegradable polymer recently developed by us. Dicylcohexyl carbodimide (DCC) mediated coupling reaction using cinnamate acid yielded PSeD-Cinnamate. The structure has been demonstrated by NMR. It can dissolve well in organic solvent such as chloroform. Exposure of colorless PSeD-Cinnmate film to UV ($\lambda$=365 nm) resulted in a yellow film which could not dissolved in chloroform. It meant that the photo-cycloaddition of cinnamate group had run successfully. Now we are exploring photo-cleavage reaction of crosslinked polymeric network at UV of short wavelength. Various backbone can be used to modulate the properties of the polymer system. For example, polyvinyl alcohol (PVA) is a commercially available polymer. The corresponding cinnamate would be also a reversibly photo-crosslinkable polymer system (FIG. 15).

Figure 16:
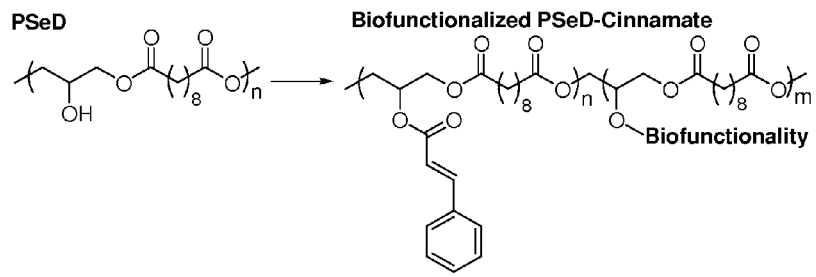
FIG. 16. An example of bioactive and reversibly photo-crosslinkable polymer.

Potential Applications
1. Photo-reversible thermoset polymer—There are two types of polymers: thermoplastic, which is physically crosslinked, and thermoset, which is chemically crosslinked. Thermoset polymer outperform thermoplastics in many aspects: strong crosslink, mechanical and thermal stability, uniform biodegradation. But usually the thermoset polymer is irreversibly covalently crosslinked, and thus it can't be refabricated, while thermoplastics is relative easily refabricated by melt or solvent processing. The proposal reversibly photo-crosslinkable polymer system such as PSeD-Cinnamate will integrate the advantages of both thermoset and thermoplastic. After photocrosslink, they can be used as thermoset polymers with corresponding properties. But unlike other thermoset polymers, their crosslinking can be photo-reversible cleaved to regenerate thermoplastic prepolymer such as PSeD-Cinnamate and thus can be refabricated as thermoplastic polymers.
2. Photo-reversible substrate for lithography—Photolithography can directly create a micro-pattern either on proposal photo-crosslinked polymeric network in which the portion exposed to light will be becomes soluble and removed, or on proposal photo-crosslinkable prepolymer in which the portion unexposed to light will be soluble and removed. An apparent feature of this photolithography substrate is that it can be photo-reversibly fabricated. When exposed to UV of short wavelength, the network can regenerate meltable and soluble prepolymer. Therefore it can be refabricated to a new pattern.
3. Applications in biomedical engineering—Since the cinnamate acid is nontoxic, when it is attached to a biodegradable and biocompatible polymeric backbone via hydrolyzable ester bond, the corresponding polymer such as PSeD-cinnamate can be expected to be biodegradable and biocompatible (FIGS. 14 and 16). In addition, the functional groups in the precursor can be just partly attached by cinnamate groups and the remains can be modified by other biofunctionalities to modulate the interaction between material and cells (FIG. 16). These polymers holding interesting chemical, physical, and biological properties will be useful for biomedical applications.

Example 3

Figure 17:
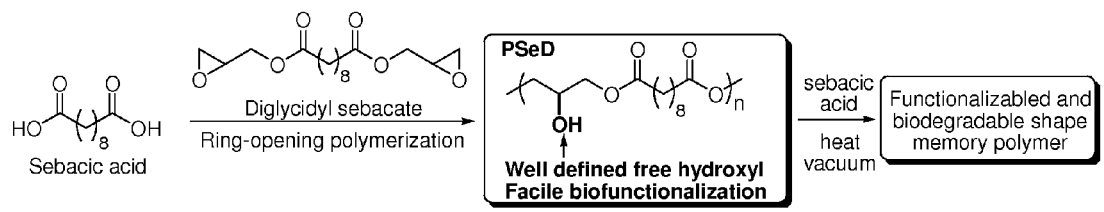
FIG. 17: Synthetic route of the functionalizable and biodegradable shape memory polymer.

A Functionalizable and Biodegradable Shape Memory Polymer Tailored for Biomedical Applications Shape-memory polymers are special family of elastomers. As a smart material, shape-memory polymers can store an elastic deformation fixed to a temporary, dormant, and relative stiff state, and recovery to a permanent, stable, elastic state upon thermal stimulation. For clinically practical interest, the transition temperature, which triggers the shape recovery, is adjusted to around body temperature. Then the device made from shape-memory polymer can be fabricated to a small, rigid, easy handling state during implantation at room temperature for minimally invasive surgical procedures, and deploys automatically to a designed shape fit the damage tissue, becoming soft and elastic at body temperature to serve as an ideal compliant material for soft tissue. Shape-memory polymers have already shown some optimistic biomedical applications such as sutures, actuators, catheters, and stents (see, e.g., Sokolowski, W., et al. *Biomedical Materials* 2007, 2, (1), S23-S27; Liu, C., et al. *J. Mater. Chem.* 2007, 17, (16), 1543-1558; and Langer, R., et al. *Nature* 2004, 428, (6982), 487-492). However few shape memory polymer are both functionalizable and biodegradable. Herein we address this challenge by well designed crosslinked polyester network using a biodegradable and functionalizable poly(sebacoyl diglyceride) (PSeD) as the prepolymer (FIG. 17). The polymeric network shows shape memory property around body temperature suitable for biomedical applications.

Figure 18:
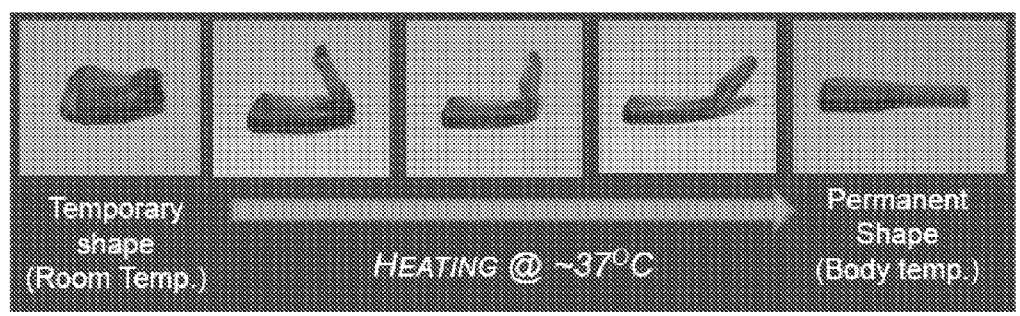
FIG. 18. Cured PSeD can be folded to a temporary shape and fixed at room temperature. When it is heated at 37° C., it can automatically deploy to permanent shape over a period of 5 minutes.
Figure 19:
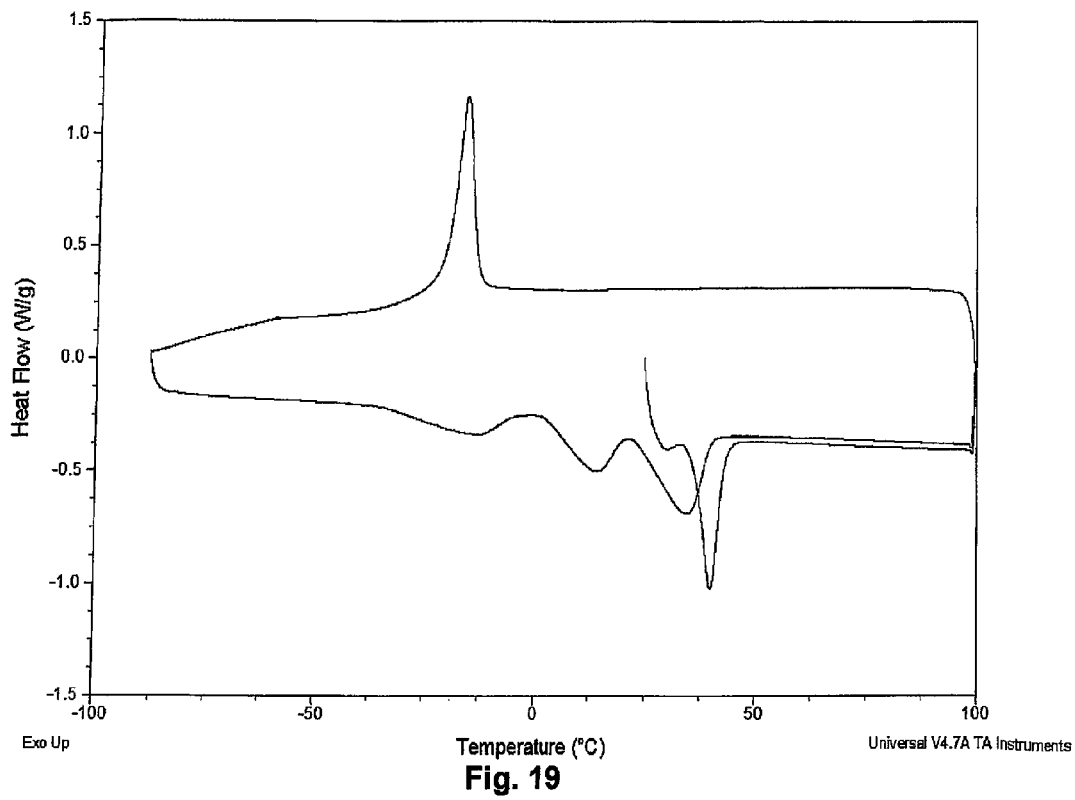
FIG. 19. Cured PSeD showed a melting temperature around 37° C. at both first and second heating cycles, which corresponded to its shape memory behavior at body temperature.

Microwave-assisted ring-opening reaction between diglycidyl sebacate and sebacic acid in presence of a catalytic amount of bis(tetrabutylammonium) sebacate provided PSeD (FIG. 17). Curing PSeD with 1.1 wt % sebacic acid in a vacuum oven yielded crosslinked PSeD. The polymer posed apparent shape memory properties at 37° C. (FIG. 18). DSC showed that it does have a melting temperature around 37° C., which corresponds to the transition temperature (FIG. 19).

Conclusions

We designed and synthesized a shape memory polymer with a transition temperature around 37° C. relevant to clinical interest. Its shape recovery period is around 5 minutes suitable for surgical procedure. Its shape memory properties can be further modulated by adjusting curing conditions and using prepolymer with different molecular weight. It is a biodegradable and functionalizable. Now we are modifying it with oligopeptides making it amenable for special application and investigating its potential to serve as a bioactive shape memory stem and scaffold.

Example 4

Neuroactive Polymer With Acetylcholine-Like Moieties

Figure 20:
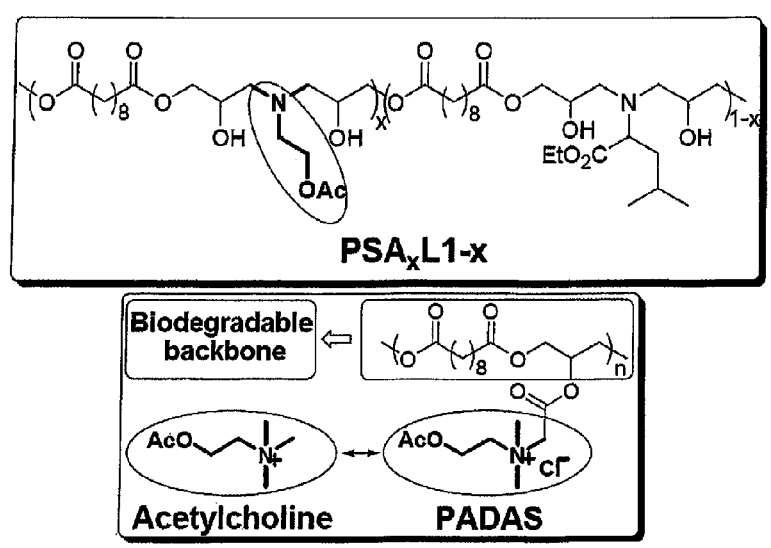
FIG. 20. Example of polymer functionalized with acetylcholine-like group PSA$_x$L$_{1-x}$, in particular, PSeDA100.

Neurotransmitters transmit nerve impulses and regulate neural activities. Thus, we hypothesize that integration of neurotransmitter functionalities into a biomaterial will produce a material that can interact with nerve cells. Acetylcholine (Ach) is an important neurotransmitter that induces neurite outgrowth and may promote the formation and strengthening of synapses. Recently we developed a series of biodegradable polymers with various concentration of Ach-like functional groups PSAxL1-x (Gumera, C. B.; Wang, Y. Adv. Mater. 2007, 19, 4404-4409). They promote dorsal root ganglia (DRG) neurite sprouting and extension depending on the concentration of the Ach groups. Further, the addition of Ach receptor antagonists greatly diminishes neuritogenesis. Accordingly we design the second generation of this series of polymers, 2-((2-acetoxyethyl)dimethylammonio)acetyl-substituted poly(sebacoyl diglyceride) (PSeDA100), integrating a pendant group that more closely resembles Ach via longer side chains. The better presentation of the Ach-like groups may assist potential interactions of PSeDA100 and neurons (See FIG. 20).

Figure 21A:
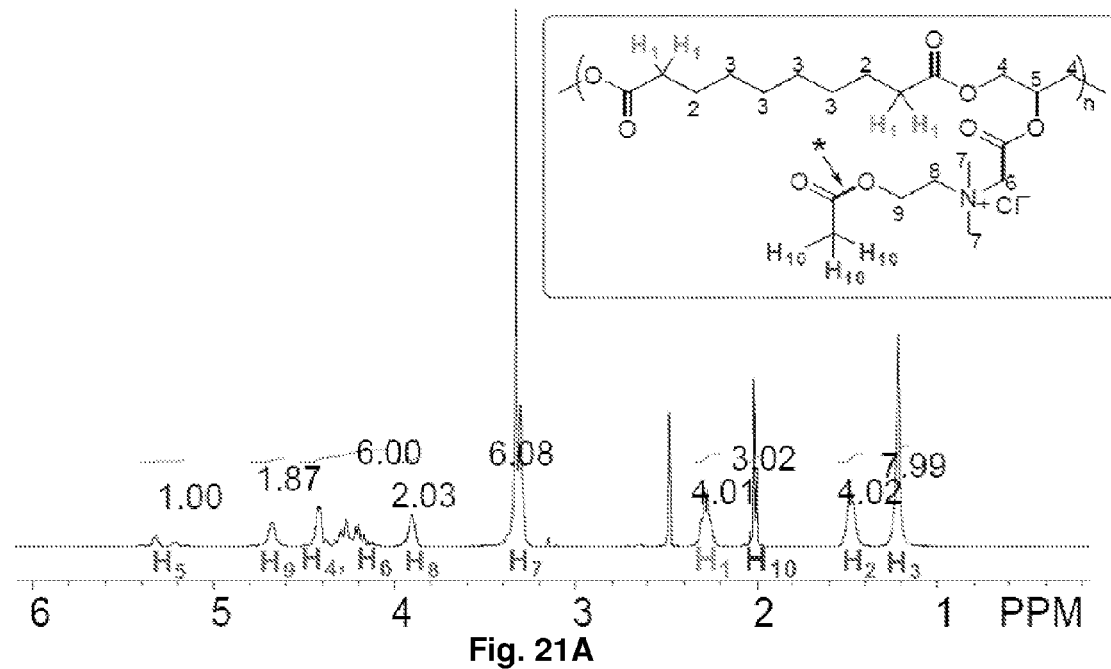
FIG. 21. NMR (FIG. 21A) and FTIR (FIG. 21B) of PSeDA.
Figure 21B:
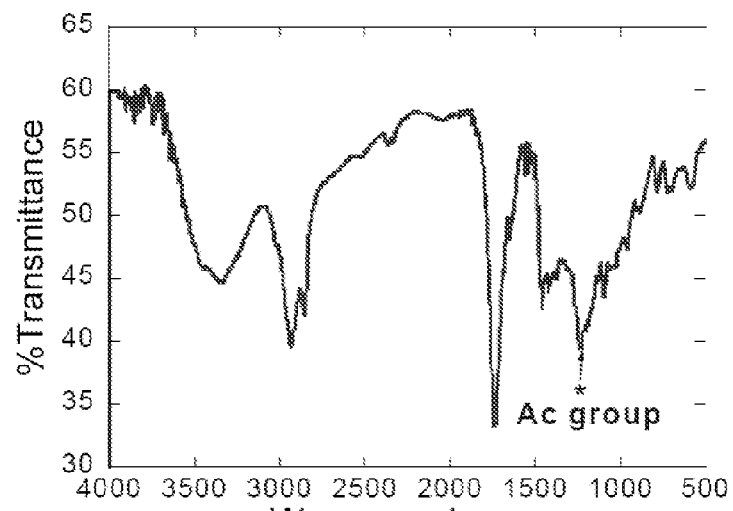

PSeD-A100 was synthesized in 3 steps with an isolated yield of 63%. Its structure was determined via NMR and FTIR (FIGS. 21A and 21B). The molecular weight and thermal properties of PSeDA100 were characterized by gel permeation chromatography, thermal gravimetric analysis and differential scanning calorimetry respectively:

$M_n$=82.3 kDa; PDI=2.9; $T_{decomposition}$=148.2° C.; and $T^a_{glass\ transition}$=-8.5° C.

Figure 22A:
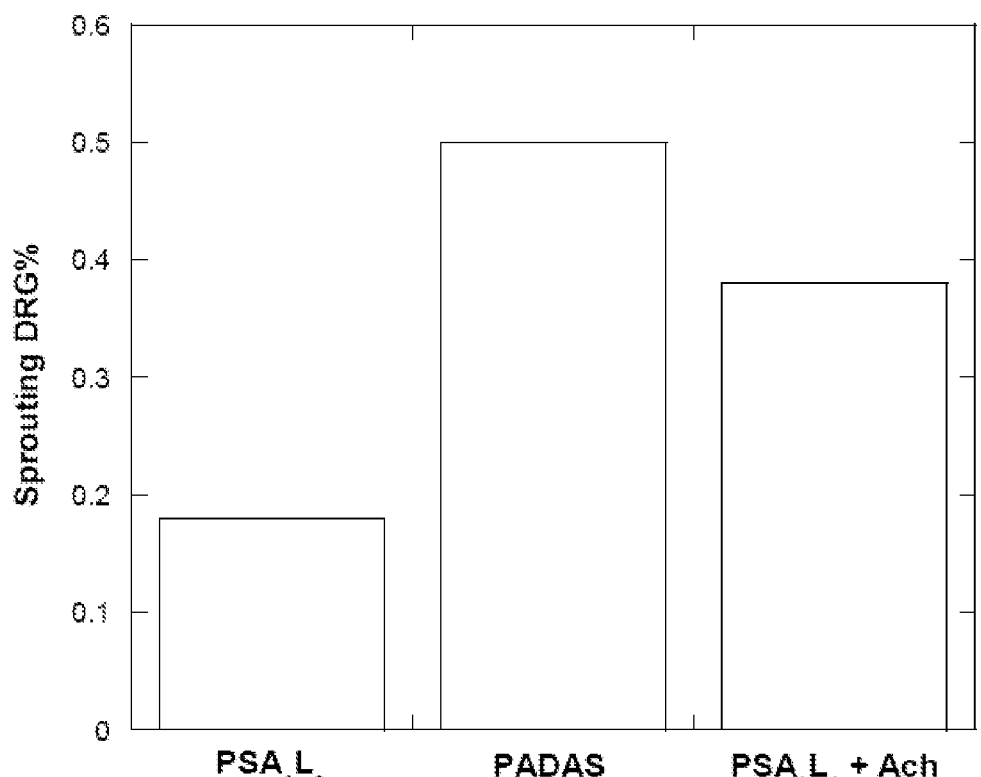
FIG. 22. PSeD-A100's ability to support neurite outgrowth was characterized using explanted rat DRG. It was found that 50% DRG showed significant neurite extension on PSeD-A100 Surface (DRG with >20 neurites projections around the majority of the perimeter were considered to have neurite sprouting) (FIGS. 22A and 22B).
Figure 22B:
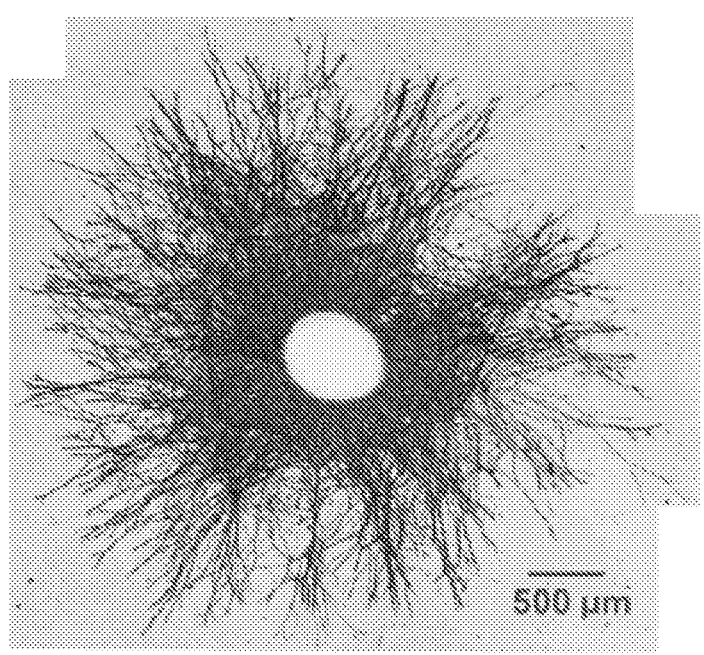

PSeD-A100's ability to support neurite outgrowth was characterized using explanted rat DRG. It was found that 50% DRG showed significant neurite extension on PSeD-A100 Surface (DRG with >20 neurites projections around the majority of the perimeter were considered to have neurite sprouting) (see FIGS. 22A and 22B). This is significantly higher than the corresponding 1st generation Ach-mimetic polymer (PSA1L0) and Ach itself (1 mM in medium) combining with control polymer (PASA0L1) (Gumera, C. B.; Wang, Y. Adv. Mater. 2007, 19, 4404-4409).

In conclusion, PSeD-A100 is more capable at inducing neurite outgrowth than the corresponding first generation Ach-mimetic polymer PSA1L0 and Ach itself. Based on our observations in the first generation polymers, we expect that the PSeD-A100 analogs with moderate concentrations of Ach-like functional groups will be very efficient at inducing neuritogenesis. We will investigate the effect of adjusting the concentrations of Ach-like functional group on neurite outgrowth using non-acetylated groups (choline mimetics). In addition, we will examine potential biochemical pathways involved in the interactions between PSeD-A100 and neurons.

Example 5

A Versatile Synthetic Platform for Functionalized Biomaterials

The synthetic strategy—epoxide ring opening polymerization between various dicarboxylic acids and diepoxides using newly designed initiator to produce diverse functionalized polyesters is described herein. The polymerization tolerates various functional groups: alkenyl, aromatic, ether, ester, and free hydroxyl groups. The produced functional groups enable versatile post-functionalization. This platform delivers biomaterials with a wide range of properties: from water soluble to hydrophobic, from amorphous, to glassy or crystalline at body temperature, from neutral to negative, positive, or zwitterionic, from soft (Elastic modulus E=0.939±0.485 kPa) to tough (E=2.155±0.557 GPa, fracture strength a >207 MPa), from osteoconductive to neuroinductive. To the best of our knowledge, this is the first reported platform that can produce functionalized biomaterials in such a simple, versatile, and controlled way.

Biomaterials play a central role in medical device and regenerative medicine, and has made and will continue to make major impacts on healthcare. Active research in biomaterials is shifting from biostable to biodegradable. Convergence of biodegradability and functionality such as mechanical property and bioactivity is a major direction of new generation biomaterials. Among various synthetic biodegradable materials, polyester is perhaps the largest class with classic examples such as polylactide. However, synthetic polymers including polyesters are usually biologically inert and lack functional groups. Though there are significant efforts in making functionalized polyesters, the synthesis is typically tedious with protection and deprotection steps and relative limited scope of substrates. Furthermore, not only the functionalized structure of repeating units but also the precise sequence of repeating units are crucial for the function of biomacromolecules. However, defined control of repeating unit sequences is still a central challenge in contemporary polymer science. We set out to address these two critical barriers by designing a simple and versatile synthetic platform that yields functionalized polyesters with diverse physical, chemical, mechanical, and biological properties.

This platform is more efficient and versatile than existing synthetic methods of functionalized polyesters. This platform technology utilizes epoxide ring opening polymerization, where epoxy groups serve as both the reactive polymerizable functional groups and the precursor of the hydroxyl groups. Thus the polyester backbone and the free hydroxyl groups form in one step without protection and deprotection (generation 1 polymers), which are required for almost all existing chemical methods to synthesize functionalized polyesters. The hydroxyl group is a versatile modification site and can be easily converted to various functionalized generation 2 polymers. Further modification of the generation 2 polymers can produce more derivates (generation 3 and higher polymers). The abundant functional groups in various generations' polymers can be used to bioconjugate with various biomolecules such as peptide or crosslink to produce various functionalized polymeric networks. Essentially this synthetic platform provides an unlimited ability to produce functionalized polyesters. Furthermore, readily producing various alternating copolyesters exemplified the feasibility of controlling the sequence of repeating units using this synthetic platform. To best of our knowledge, it is the first example that can produce functionalized polymer with controlled sequence in such a simple (one step from commercially available materials) and versatile way. This synthetic platform overcomes critical barriers in biomaterial synthesis. We expect it will have a wide range of biomedical engineering applications.

Figure 24:
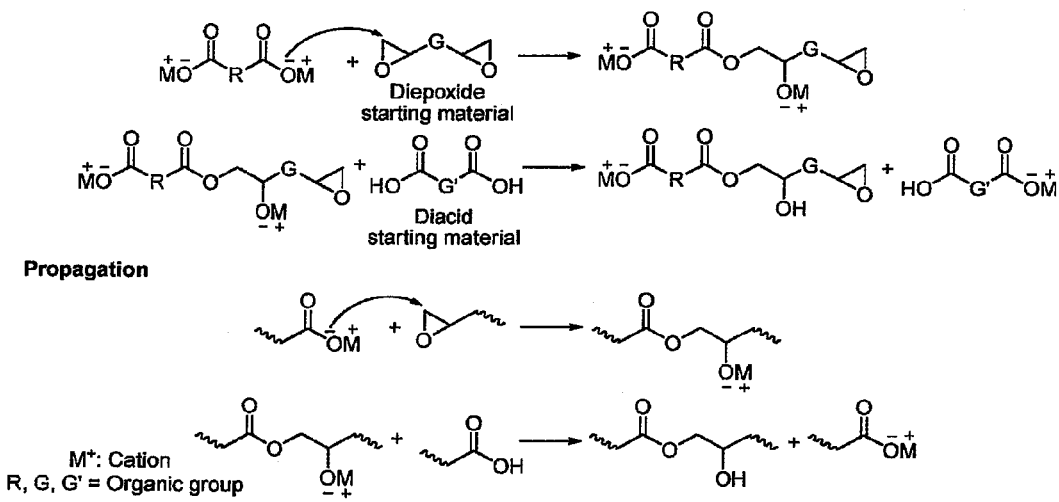
FIG. 24. Proposed mechanism of carboxylate initiated epoxide ring opening polymerization.

As indicated above, a difficulty of this synthetic platform is a potential side reaction between the epoxy groups and hydroxyl groups in the oligomers and polymers already produced in epoxide ring opening polymerization. Accordingly we designed a new initiator, bis(tetrabutylammonium) sebacate and optimized the reaction conditions including initiator dosage, heating method, reaction temperature and duration using polymer 1C as a model compound (FIGS. 23 and 24 and Tables 5-7).

TABLE 5

Solubility of the initiator - bis(tetrabutylammonium) sebacate.

| Hexane | Et$_2$O | CH$_2$Cl$_2$ | CHCl$_3$ | THF | Acetone | CH$_3$CN | C$_2$H$_5$OH | DMF | H$_2$O |
|---|---|---|---|---|---|---|---|---|---|
| − | − | + | + | + | + | + | + | + | + |

+: >10 g/l.
−: <1 g/l. (at ambient temperature)

TABLE 6

Reaction condition screen based on model polymerization between sebacic acid and diglycidyl sebacate.

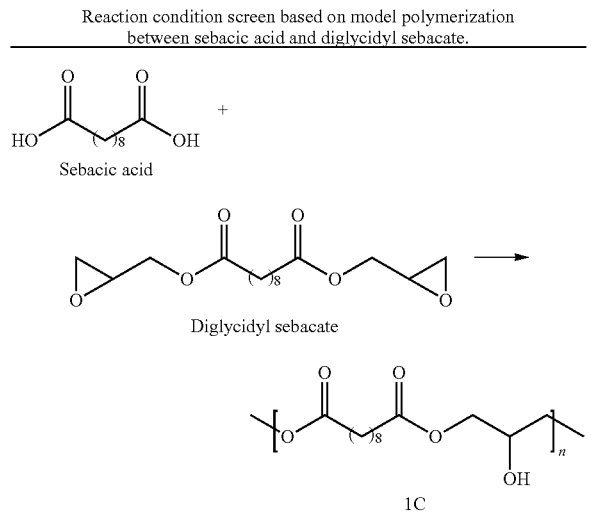

| Run[a] | Initiator (mol %) | Heating method[b] | Temp (° C.) | Time (hour) | Mn (kDa) | PDI | Yield |
|---|---|---|---|---|---|---|---|
| 1 | None | Microwave | 170[c] | 0.27 | 3.9 | 1.6 | 39% |
| 2 | 5 | Microwave | 170[c] | 0.27 | — | — | Gelation |
| 3 | 3 | Microwave | 170[c] | 0.27 | 6.5 | 2.5 | 88% |
| 4 | 1.5 | Microwave | 170[c] | 0.27 | 6.9 | 15 | 84% |
| 5 | 0.6 | Microwave | 170[c] | 0.27 | 13.0 | 1.4 | 80% |
| 6 | 0.2 | Microwave | 170[c] | 0.27 | 10.7 | 1.3 | 77% |
| 7 | 0.6 | Microwave | 170[c] | 0.42 | 7.0 | 1.5 | 82% |
| 8 | 0.6 | Microwave | 90 | 24 | 28.8 | 1.3 | 74% |
| 9 | 0.6 | Microwave | 90 | 48 | — | — | Gelation |
| 10 | 0.6 | Oil bath | 75 | 24 | 11.7 | 1.6 | 78% |
| 11 | 0.6 | Oil bath | 90 | 26 | 82 | 1.4 | 87% |

[a]After some initial testing, we selected DMF as the solvent to optimize the polymerization because DMF showed to be a good solvent for many reactants and its high boiling point allowed a wide reaction temperature range.
[b]We investigated microwave-assisting epoxide opening polymerization for quick screening the reaction conditions. However the enhanced viscosity of the reaction system with the increasing of the molecular weight and limited stirring ability of microwave reactor made the polymerization of high molecule weight polymers difficult. Thus we also tried the traditional heating method.
[c]The reaction was carried out at 100° C. for 10 min to mix the reactants well before subjected to 170° C.

TABLE 7

Tunable physical and thermal properties of generation 1 polymer 1A synthesized by different polymerization conditions.

| Conditions | Water solubility | Tg |
|---|---|---|
| 70° C., 17 h | >100 g/l | 9.7° C. |
| 90° C., 26 h | <1 g/l | 66.2° C. |

This platform is applicable to a wide range of substrates including short-chain (generation 1 polymer 1F) and long-chain (generation 1 polymer 1B-C), linear (generation 1 polymer 1A-E) and cyclic (generation 1 polymer 1F-H), aromatic (generation 1 polymer 1E, 1G) and aliphatic (other generation 1 polymer) to produce diverse functionalized polyesters with moderate molecular weight, low polydispersity index (PDI) and good yield (FIG. 23). The polymerization exhibits broad tolerance of various functional groups such as ether (generation 1 polymer 1B), ester (generation 1 polymer 1C-H), alkenyl (generation 1 polymer 1A, 1D), and even free hydroxyl (generation 1 polymer 1H). The good tolerance of functional groups makes it feasible to build subtle structures into starting materials—diacids and diepoxides. Consequently elegant polymeric architecture can achieve. For example, diacid reacts with diglycidyl ester to produce copolyester (such as generation 1 polymer 1F) with two different repeating units (succinoyl diglyceride and 1,2-cyclohexane diacyl diglyceride) in an alternating architecture. Simply employing different commercially available diacids can vary the structures of repeating units (generation 1 polymer 1F-H). This design provides a simple solution to a significant challenge in polymeric biomaterial synthesis—controlling the sequence of repeating units. Moreover, we can tailor the resultant polymers to be the functionalized counterpart of known biomaterials. For example, generation 1 polymer 1F is a hydroxylated poly(propylene fumarate), a photocrosslinkable polymer that have been widely used in tissue engineering scaffolds, drug delivery vehicles, orthopedic grafts, and cell transplantation vectors (F. K. Kasper, et al. *Nat Protoc* 4, 518 (2009)). Generation 1 polymer 1E can be viewed as the analog of polyethylene terephthalate), the third most produced polymer in the world that has been widely used in industry and clinic such as artifical vascular grafts. We expect that these functionalized counterparts will succeed the outstanding profile of the parent non-functionalized biomaterials and exhibits more sophisticated features.

Figure 25A:
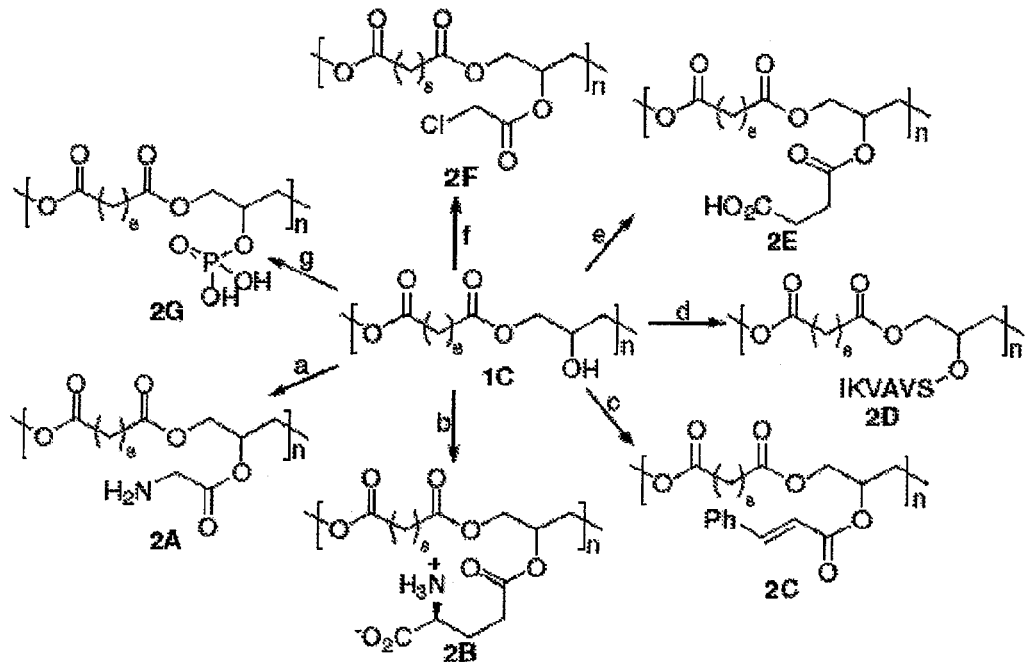
FIG. 25A-25C. Diverse post-functionalization of the polyesters.

In this design, we chose hydroxyl as the universal functional group of generation 1 polymers because of its established and easy modification methods. Using generation 1 polymer 1C as a foundation, we demonstrated the wide range of possible modifications of the hydroxyl groups (FIG. 25A, Table 8), which reacted with various functional groups such as acid (generation 2 polymer 2A-C, 2G), anhydride (generation 2 polymer 2D), acyl chloride (generation 2 polymer 2E), and phosphoryl chloride (generation 2 polymer 2F).

TABLE 8

Characterization of the derivates of generation 1 polymer 1C

| Compound | Expected functionalization % | Resultant functionalization %[a] |
|---|---|---|
| 2A | 100% | 95[b] |
| 2B | 100% | 90[b] |
| 2C | 100% | 70[b] |
| 2D | 30% | 25[b] |
| 2E | 100% | 100[b] |
| 2F | 100% | 100[b] |
| 2G | 50% | 17[c] |
| 3A | 100% | 100[b] |

[a]The percentage of the conversion from hydroxyl groups to corresponding functional groups. The reaction conditions were not optimized.
[b]According to relative integration analysis in $^1$H NMR spectra.
[c]According to ICP analysis of phosphorus.

Figure 25B:
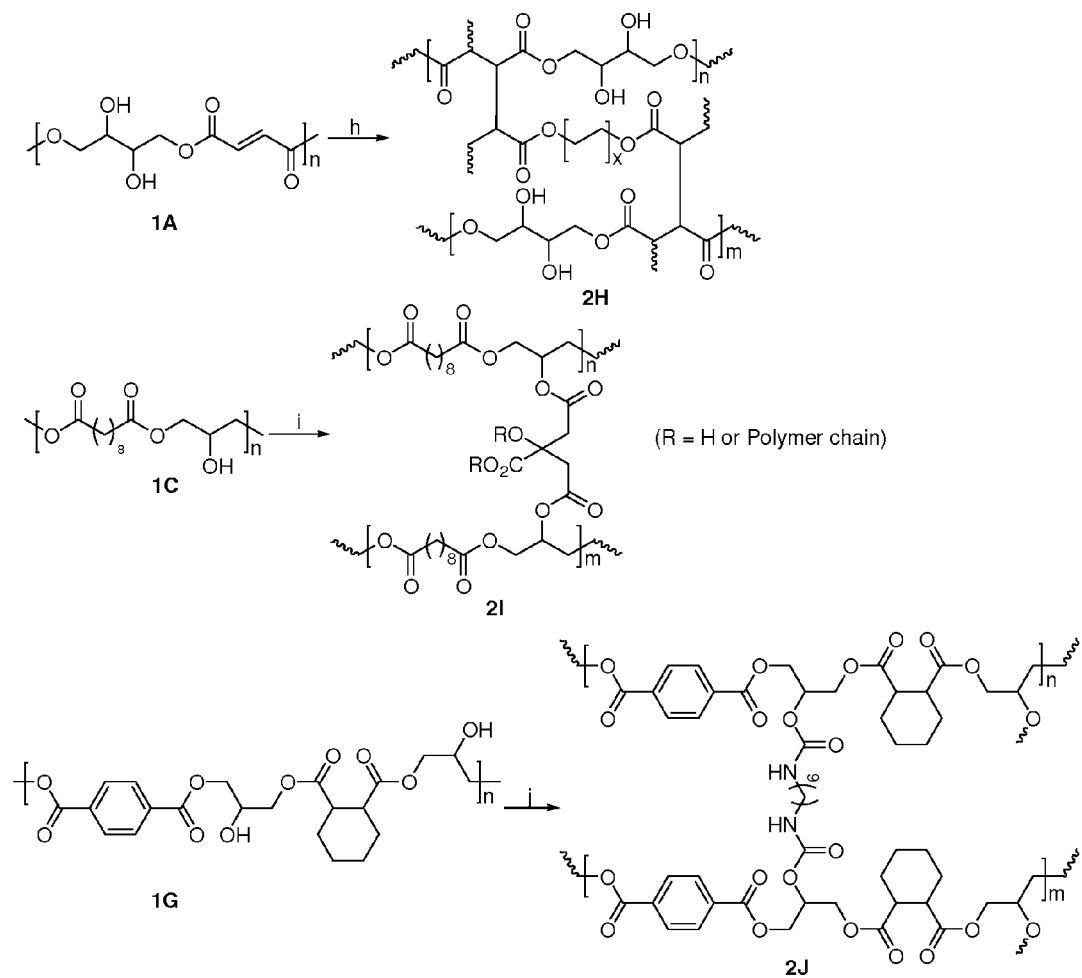
Figure 25C:
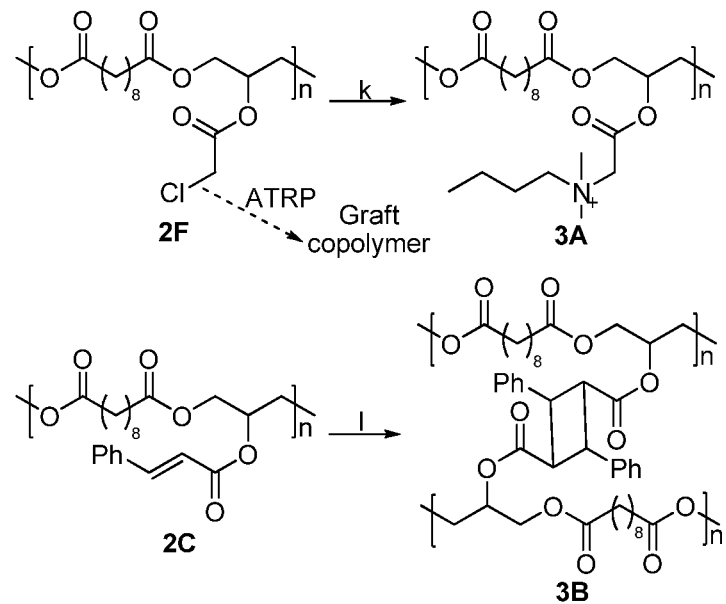
Figure 26A:
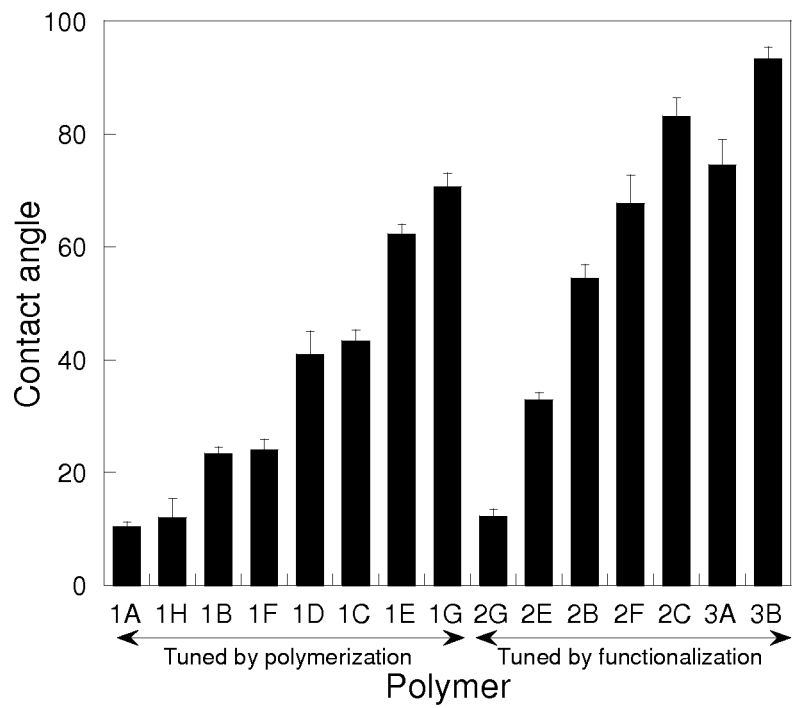
FIGS. 26A-26H. Diverse physical, thermal, mechanical, and biological properties of the resultant polymers. (A) Hydrophilicity characterized by water contact angle on polymer films. (B) Thermal properties according to differential scanning calorimeter analysis. (C) Charge properties of representative polymer 1C and its derivatives. (D) Tensile (2I)/compression (2H, 2J) properties of representative networks. $^a$The point at which the loading strength extended the capability of the mechanical tester. (E-H) Controlling bioactivity via representative biofunctionalizations: (E-F) Differentiated rat pheochromocytoma (PC12) cells (a common cell line for neuroactivity evaluation) on polymer 2D and laminin control (a standard substrate for neuron culture) at day 5. More extensive neurite network formed on polymer 2D than laminin. (G) The neurites of differentiated PC I2 cells on polymer 2D extended significantly in another day and was significantly longer than that on laminin. Twenty longest neurites from 10 images on each surface per day were measured. (H) The alkaline phosphatase (ALP) activity of rat osteoblast cells on polymer 2G surface were significantly greater than that on Tissue culture treated polystyrene (TCPS) surface at day 14 and 21 after seeding. The result was normalized by total protein content. Data represent mean±SD. * Statistical significance (Student's t test, $p<0.05$).
Figures 26B, 26C, 26D:
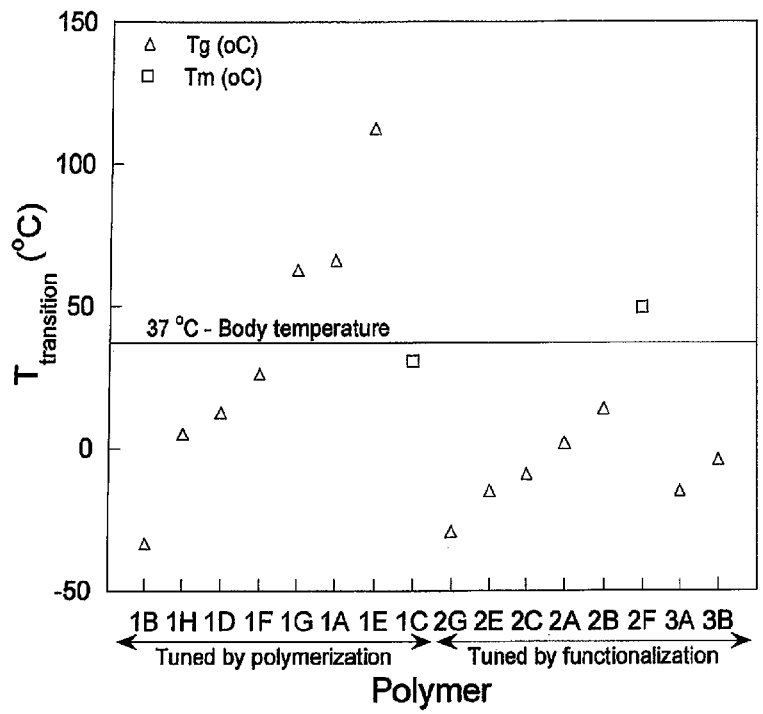
Figure 27:
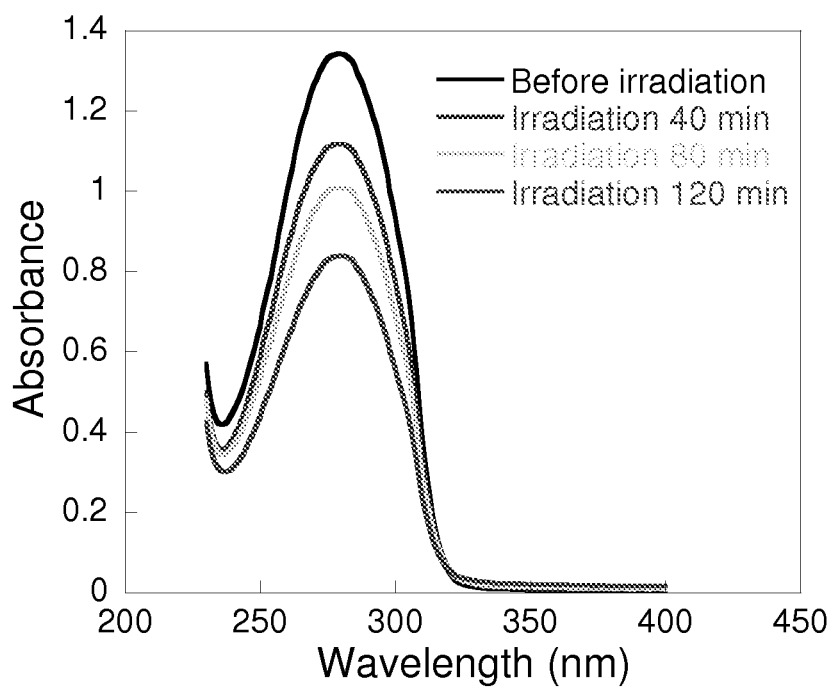
FIG. 27. Spectra characterization of the conversion from polymer 2C to 3B. Changes in the UV absorption spectra of the film of 2C with UV irradiation at $\lambda=365$ nm. The peak absorption at around 280 nm corresponding to the cinnamoyl groups decreased indicating the conversion of 2C to 3B.
Figure 28:
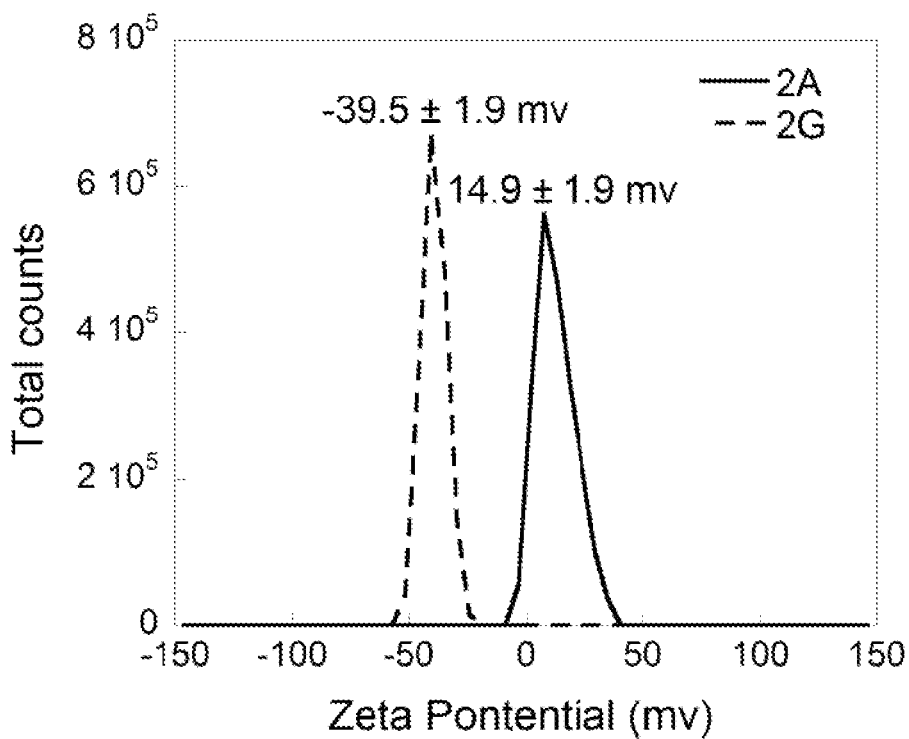
FIG. 28. Zeta potential distribution of polymer 2A and 2G in MeOH solution.

Hydroxyls can also be crosslinked by various reagents such as polyacid (2I), and diisocyanate (2J) to yield diverse three dimensions networks with tunable properties (FIGS. 25B and 26D). Besides hydroxyl, other functional groups in generation 1 polymer can further enrich the diversity obtainable with this synthetic platform. For example, photocrosslinking of alkenyl groups of generation 1 polymer 1A in an aqueous solution produced a hydrogel system 2H (FIGS. 25B and 26D), that might be hard to access via the modification of hydroxyl groups. Further, these modifications lead to diverse functional groups such as remaining hydroxyl groups, new produced amino, acid, and alkenyl groups in generation 2 polymers (FIGS. 25A and 25B), which provide robust ability for further functionalization. For example, a mild Menshutkin reaction of generation 2 polymer 2E produced a generation 3 polymer 3A (polycation) and the C—Cl bonds of 2E can also be used in atom transfer radical polymerization to yield sophisticated macromolecular architectures (see, e.g., Matyjaszewski, K et al. *Nature Chemistry* 1, 276 (July 2009)) (FIG. 25C). Generation 2 polymer 2C underwent initiator-free [2+2] photo-addition of the pendant cinnamyl groups providing an efficient method to engineer its properties in three dimensions (FIG. 25C, FIG. 27). Overall, this synthetic platform paves a new way to synthesize functionalized polyesters and will substantially accelerate and broaden the applications of functionalized biodegradable materials.

Figure 26E:
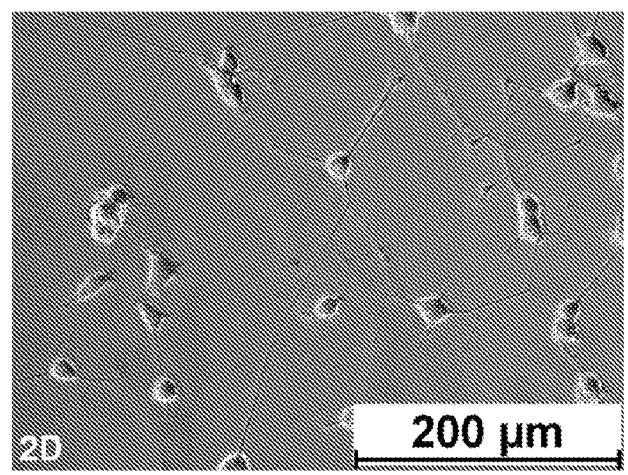
Figure 26F:
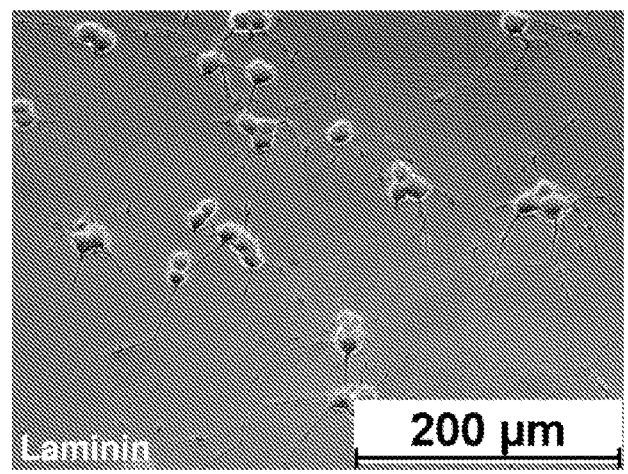
Figure 26G:
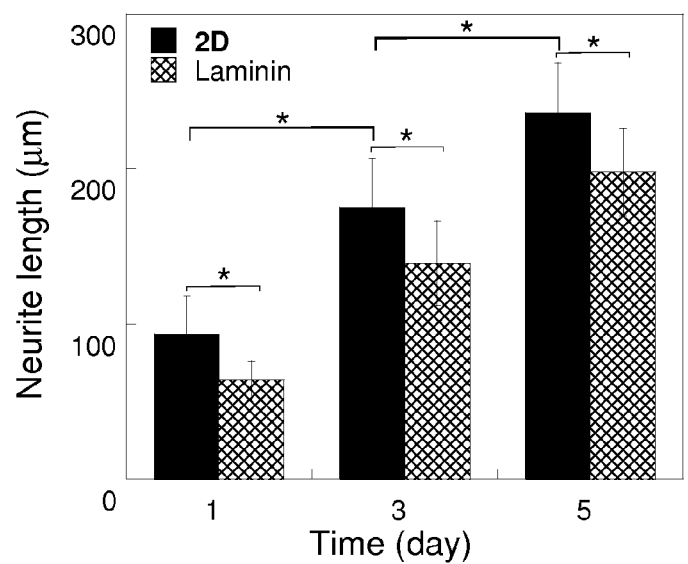
Figure 26H:
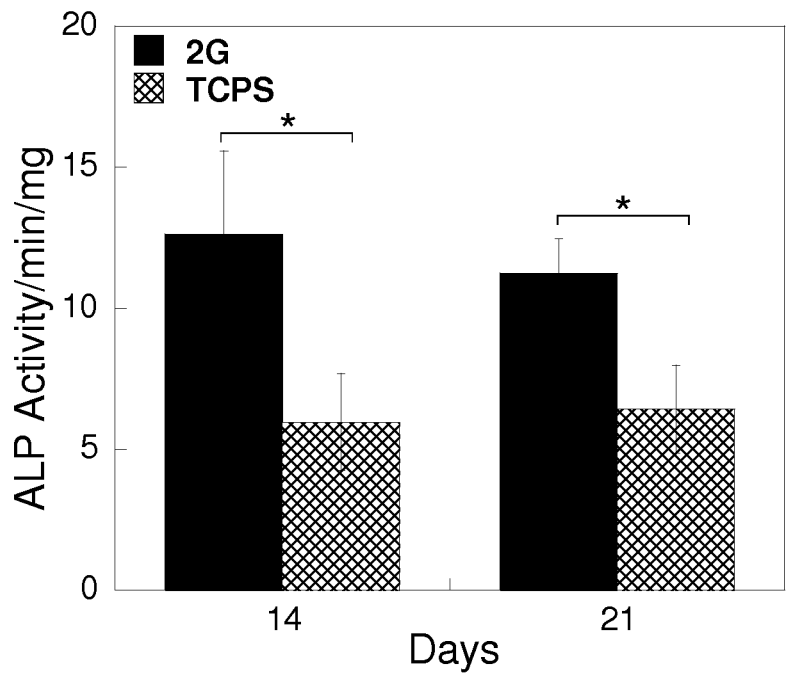
Figure 29A:
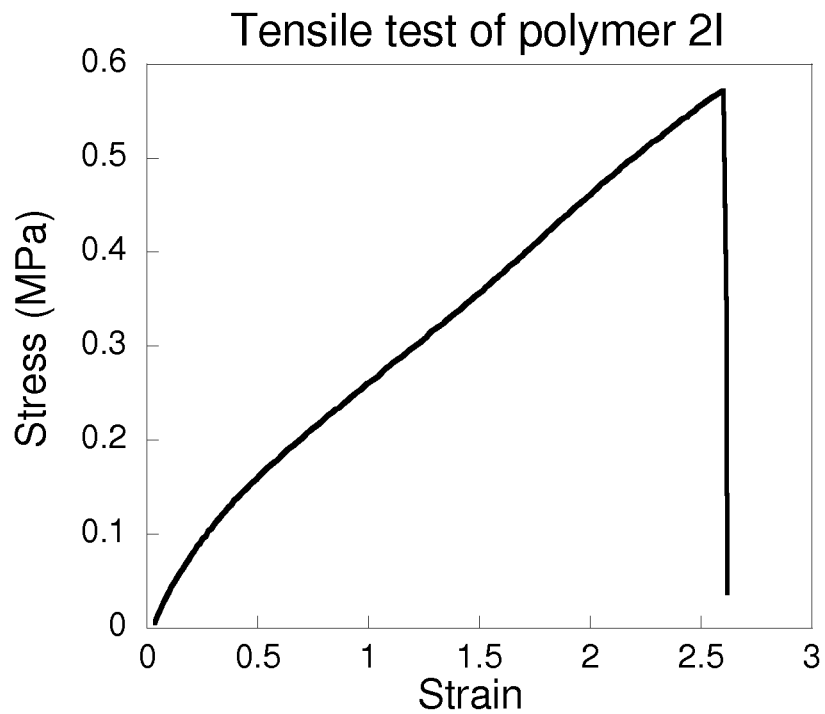
FIGS. 29A-29C Mechanical properties of representative polymeric networks. Typical stress-strain curves of polymer 2H (compression), 2I (tensile), and 2J (compression).
Figure 29B:
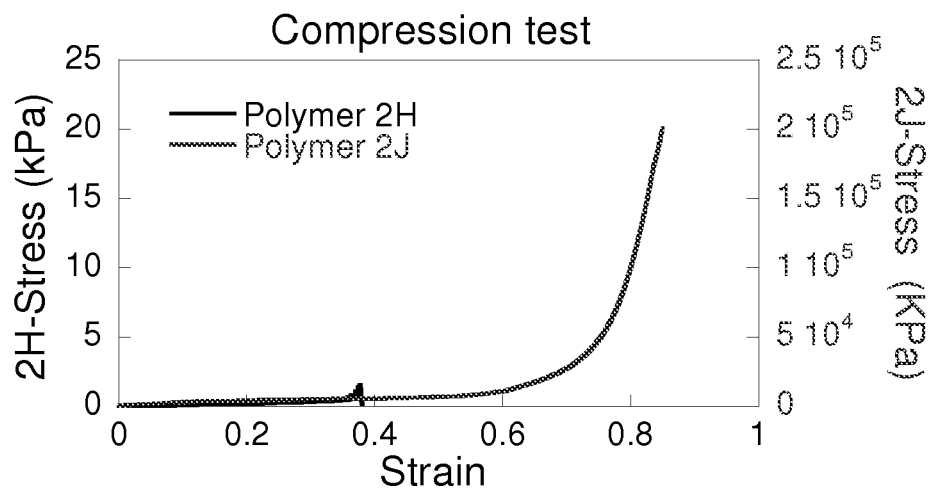
Figure 29C:
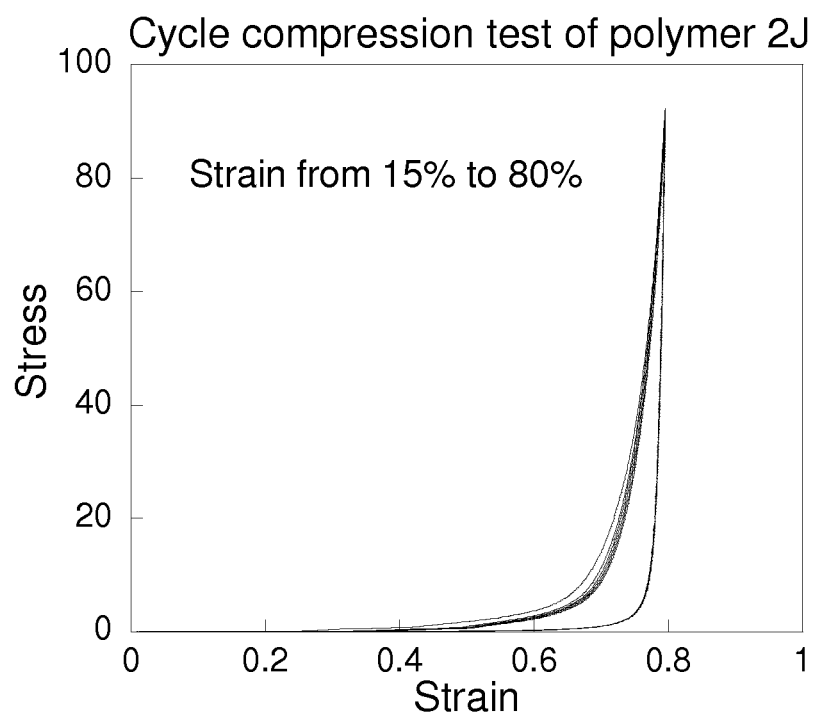

To improve the cell-material interaction, various methods have been developed to modify materials with various functionalities including biomolecules. Most of them focus on surface modification. Therefore the modulation of properties is limited to two dimensions and can't sustain upon degradation. Our motivation is to provide sustainable cell-material interaction in more physiologically relevant three dimensions environment during the whole degradation process. Thus we designed these functionalized polyesters to be amendable to bulk modification. Collectively the broadly applicable polymerization and facile post-modification strategies produce diverse polymers with a wide range of properties that will critically impact cell-material interaction. The controllable properties include but are not limited to: (1) Hydrophilicity (FIG. 26A) can be modulated either by tailoring backbone (1A-H) or modifying side chain (2A-G, 3A-B). The polymers could be hydrophobic, hydrophilic, or even water soluble (2A, low molecular weight 1A see Table 7,). (2) Thermal properties (FIG. 26B) can be controlled. The polymers can be made into semi-crystalline (2F), glassy (1A, 1E, 1G), or amorphous (Others) at body temperature. Therefore they range from stiff to pliable at physiological temperature amenable for different applications. In addition, we can control the polymers (1C, 1F) to have phase transition (melting or glassing) between room temperature (25° C.) and body temperature (37° C.) indicating that they might be used as shape memory polymers for smart medical devices. (3) Charge properties (FIGS. 26C and 30) of the polymers (1A-G) can be customized by modification of the free hydroxyl groups. For example, the neutral polymer 1C gave rise to polymers 2A-B, 2D, 2E, 2G, and 3A with totally different charges. (4) Mechanical properties (FIG. 26D FIG. 29) can be adjusted over 6 orders of magnitude: from soft (2H, modulus 0.939±0.485 kPa) to tough (2J, modulus 2.155±0.557 GPa). The maximum compressive strength of polymer 2J exceeded 207 MPa. To the best of our knowledge, polymer 2J was among the strongest polymeric materials reported (33). (5) Bioactivity (FIGS. 26E-H) can be efficiently tailored via modification with biomolecules such as peptides or even functional small molecules. For example, polymer 2D (FIGS. 26E-G) conjugated by a laminin epitope IKVAVS (SEQ ID NO: 13) and polymer 2G (FIG. 26H) tethered by phosphate groups showed robust neuroinductivity and osteoconductivity respectively.

In conclusion, we develop a platform technology to produce functionalized polyesters that are difficult to achieve by conventional methods. The resultant materials have a wide range of properties and thus are amenable to various applications (the data will be published elsewhere) such as tissue engineering (such as polymer 2D for nerve regeneration and 2G for bone regeneration), drug delivery (such as water soluble polycation 2A for gene delivery), and medical device (such as shape memory polymer IC as minimally invasive stent). We expect this research will pave a new way for design of functionalized biomaterials and discovery of a new generation biomaterials. In addition to biomedical applications, polyesters can be used in various fields such as fibers, films, packaging, textile, electronic devices. Particularly, polyesters have become an important environmentally friendly alternative to commodity plastics because polyester can be designed to be compostable. Thus this platform will be a powerful tool to engineer new eco-friendly materials for various applications. Further, introduction functionalities can also make more opportunities to tailor the material's properties and be more amenable to sophisticated applications such as nanotechnology. We expect this technology will have wide impact on modern materials.

Structures of the bis(tetrabutylammonium) sebacate initiator, the di-epoxides monomers incorporated into 1C, 1D, and 1E, and compounds 1A-H, 2A-G, 3A and 3B were confirmed by NMR and IR spectroscopy:

Bis(tetrabutylammonium) sebacate: $^1$H NMR (600 MHz, CDCl$_3$) δ 3.30-3.33 (m, 16H), 2.14 (t, J=8.1 Hz, 4H), 1.56-1.67 (m, 20H), 1.41-1.47 (m, 16H), 1.27-1.29 (m, 8H), 1 (t, J=7.2 Hz, 24H); ATR-FTIR $v_{max}$ 2958, 2928, 2873, 1563, 1378 cm$^{-1}$.

Diglycidyl sebacate: $^1$H NMR (400 MHz, CDCl$_3$) δ 4.42 (dd, J=12.6, 3.0 Hz, 2H), 3.91 (dd, J=11.8, 6.2 Hz, 2H), 3.19-3.23 (m, 2H), 2.85 (t, J=4.4 Hz, 2H), 2.65 (dd, J=5.2, 2.4 Hz, 2H), 2.35 (t, J=7.8 Hz, 4H), 1.60-1.65 (m, 4H), 1.25-1.31 (m, 8H)

Diglycidyl fumarate: $^1$H NMR (400 MHz, CDCl$_3$) δ 6.94 (s, 2H), 4.56 (dd, J=12.4, 3 Hz, 2H), 4.06 (dd, J=12.4, 1.6 Hz, 2H), 3.25-3.29 (m, 2H), 2.89 (dd, J=4.8, 4 Hz, 2H), 2.69 (dd, J=4.8, 2.4 Hz, 2H).

Diglycidyl terephthalate: $^1$H NMR (600 MHz, CDCl$_3$) δ 8.15 (s, 4H), 4.70 (dd, J=12.0, 3.0 Hz, 2H), 4.19 (dd, J=12.6, 6.6 Hz, 2H), 3.36-3.38 (m, 2H), 2.93 (t, J=4.8 Hz, 2H), 2.75 (dd, J=4.8, 3.0 Hz, 2H).

Compound 1A: $^1$H NMR (DMSO-d$_6$, 400 M) δ 6.57-6.84 (m, 2H), 3.20-5.27 (m, 6H); ATR-FTIR $v_{max}$ 3338, 1713, 1647, 1257, 978 cm$^{-1}$.

Compound 1B: $^1$H NMR (CDCl$_3$, 600M) δ 3.26-5.01 (m, 14H), 2.29-2.35 (m, 4H), 1.60-1.68 (m, 4H), 1.25-1.30 (m, 8H); ATR-FTIR $v_{max}$ 3373, 2927, 2857, 1732, 1127 cm$^{-1}$.

Compound 1C: $^1$H NMR (CDCl$_3$, 600M) δ 3.73-5.10 (m, 5H), 2.31-2.37 (m, 4H), 1.62-1.65 (m, 4H), 1.27-1.31 (m, 8H); ATR-FTIR $v_{max}$ 3436, 2926, 2852, 1732, 1165 cm$^{-1}$.

Compound 1D: $^1$H NMR (DMSO-d$_6$, 400 M) δ 8.74-8.85 (m, 2H), 3.61-5.44 (m, 5H); ATR-FTIR $v_{max}$ 3421, 3080, 2957, 1716, 1647, 1152, 975 cm$^{-1}$.

Compound 1E: $^1$H NMR (DMSO-d$_6$, 400 M) δ 8.03-8.09 (m, 4H), 3.77-5.79 (m, 5H); ATR-FTIR $v_{max}$ 3400, 1713, 1505, 1243 cm$^{-1}$.

Compound 1F: $^1$H NMR (DMSO-d$_6$, 400 M) δ 3.16-5,16 (m, 10H), 2.82-2.86 (m, 2H), 2.54-2.59 (m, 4H), 1.72-1.97 (m, 4H), 1.28-1.38 (m, 4H); ATR-FTIR $v_{max}$ 3400, 2925, 2855, 1724, 1156 cm$^{-1}$.

Compound 1G: $^1$H NMR (DMSO-d$_6$, 400 M) δ 7.95-8.07 (m, 4H), 3.18-5.18 (m, 10H), 2.77-2.89 (m, 2H), 1.55-1.93 (m, 4H), 1.22-1.35 (m, 4H); ATR-FTIR ν$_{max}$ 3433, 2939, 2859, 1716, 1600, 1505, 1100 cm$^{-1}$.

Compound 1H: $^1$H NMR (DMSO-d$_6$, 400 M) δ 5.15-5.80 (m, 2H), 3.5-4.95 (m, 10H), 2.76-2.85 (m, 2H), 1.71-1.97 (m, 4H), 1.29-1.38 (m, 4H); ATR-FTIR ν$_{max}$ 3398, 2939, 2860, 1723, 1173 cm$^{-1}$.

Compound 2A: $^1$H NMR (D$_2$O, 400 M) δ 5.32-5.33 (m, 0.95H), 4.18-4.46 (m, 4.05H), 3.92-3.94 (m, 1.90H), 2.29-2.34 (m, 4H), 1.50-1.56 (m, 4H), 1.27 (s, 8H); ATR-FTIR ν$_{max}$ 2929, 2856, 1737, 1674, 1415, 1128 cm$^-$.

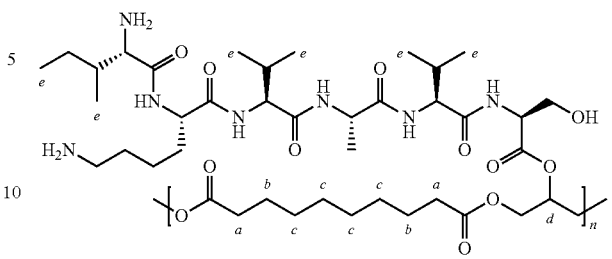

2D

Compound 2D: $^1$H NMR (MeOD-d$_4$, 600 M) δ 5.08-5.28 (m, Hd), 2.93-4.49 (m), 2.31-2.39 (m, Ha), 1.61-1.63 (m, Hb), 1.34 (s, Hc), 0.95-1.03 (m, He); ATR-FTIR ν$_{max}$ 3275, 2930, 2857, 1634, 1532, 1170, 1131 cm$^{-1}$.

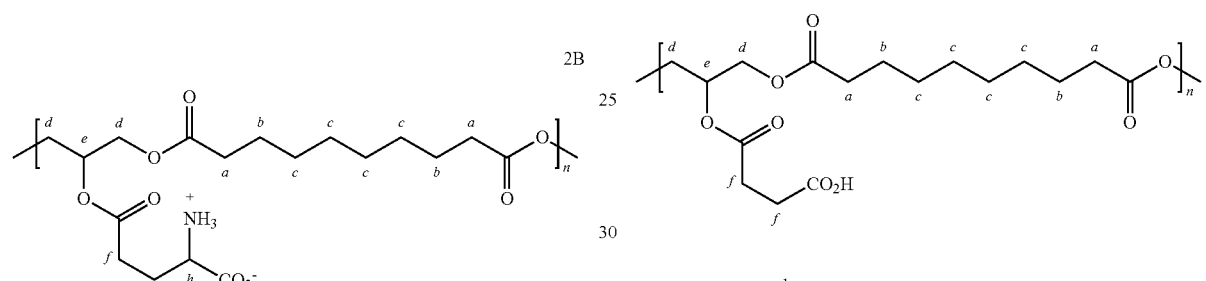

2B

2E

Compound 2E: $^1$H NMR (MeOD-d$_4$, 400 M) δ 5.27-5.32 (m, He), 4.17-4.40 (m, Hd), 2.61-2.62 (m, Hf), 2.35-2.39 (m, Ha), 1.62-1.65 (m, Hb), 1.35 (m, Hc); ATR-FTIR ν$_{max}$ 2929, 2855, 1733, 1711, 1150 cm$^{-1}$ Compound 2B: $^1$H NMR (MeOD-d$_4$, 600 M) δ 5.28-5.29 (m, He), 3.97-4.38 (m, Hd, h), 2.58-2.68 (m, Hg), 2.35-2.40 (m, Ha), 2.17-2.28 (m, Hf), 1.62 (m, Hb), 1.34 (s, Hc); ATR-FTIR ν$_{max}$ 3467, 2929, 2855, 1733, 1417, 1132 cm$^{-1}$.

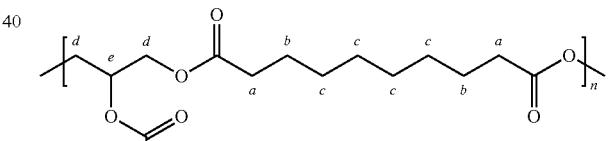

2F

2C

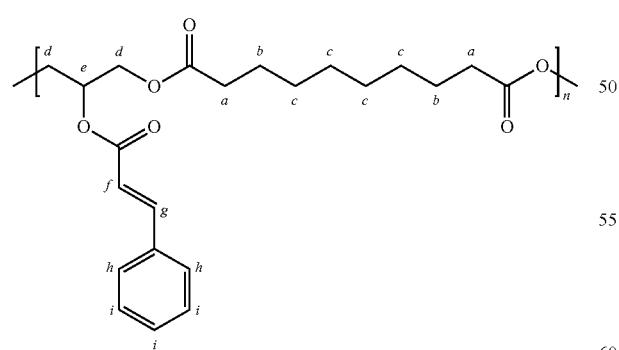

Compound 2$^1$H NMR (CDCl$_3$, 400 M) δ 5.25-5.35 (m, He), 4.11-4.49 (m, Hd), 4.07 (s, Hf), 2.31 (t, J=7.2 Hz, Ha), 1.58-1.62 (m, Hb), 1.25-1.29 (m, Hc); FTIR (thin film) ν$_{max}$ 2926, 2855, 1736, 1164, 786 cm$^{-1}$.

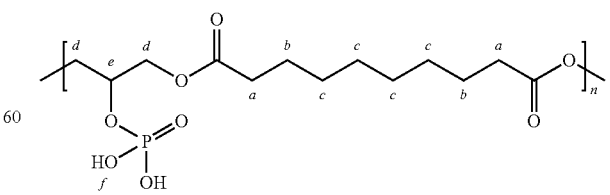

2G

Compound 2C: $^1$H NMR (CDCl$_3$, 400 M) δ 7.69-7.74 (m, Hg), 7.54 (s, Hh), 7.41 (s, Hi), 6.43-6.67 (m, Hf), 5.25-5.43 (m, He), 3.38-4.52 (m, Hd), 2.30-2.33 (m, Ha), 1.59-1.61 (m, Hb), 1.27-1.29 (s, Hc); ATR-FTIR ν$_{max}$ 3435, 2927, 2855, 1718, 1636, 1156, 982 cm$^{-1}$.

Compound 2G: $^1$H NMR (CDCl$_3$, 400 M) δ 5.09-5.31 (m, He), 3.47-3.58 (m, Hd), 2.66 (br s, Hf), 2.32-2.39 (m, Ha), 1.63-1.65 (m, Hb), 1.28-1.39 (m, Hc); $^{31}$P NMR (CDCl$_3$, 162M) δ 0.18; ATR-FTIR $v_{max}$ 3392, 2927, 2854, 1735, 1170 cm$^{-1}$.

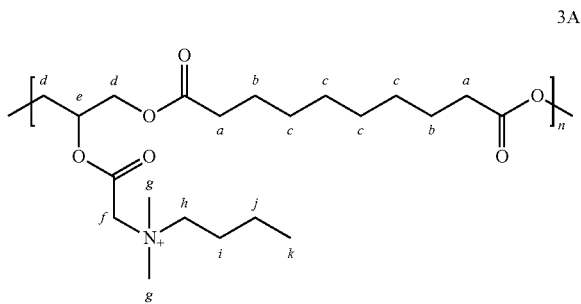

3A

Compound 3A: $^1$H NMR (DMSO-d$_6$, 600M) δ 5.16-5.40 (m, He), 3.89-4.89 (m, Hdf), 3.50-3.57 (m, Hh), 3.35 (s, Hg), 2.27-2.33 (m, Ha), 1.64-1.69 (m, Hi), 1.48-1.51 (m, Hb), 1.27-1.32 (m, Hj), 1.24 (s, Hc), 0.92 (t, J=7.2 Hz, Hk); ATR-FTIR $v_{max}$ 3383, 2931, 2856, 1736, 1167 cm$^{-1}$.
Compound 3B: ATR-FTIR $v_{max}$ 3468, 2928, 2855, 1732, 1635, 1154, 983 cm$^{-1}$.

Example 6

A Biocompatible Heparin-Binding Polycation as a Growth Factor Delivery Vehicle

Growth factor delivery is a promising therapeutic for regenerative medicine. Many efforts have been made in order to obtain appropriate delivery vehicles; however, none of them is able to fulfill all requirements. We used a biocompatible polycation, poly(ethylene argininylaspartate diglyceride) (PEAD), to form a complex with heparin. PEAD/heparin complex is able to encapsulate delivery growth factors with high efficiency and release the growth factors in a controlled fashion. Additionally, PEAD/heparin can sustain the bioactivity of the growth factor during long term culture.

Growth factor delivery is one of the main strategies for regenerative medicine. It has been examined widely and shows promising results for many indications including angiogenesis. Yet, before it can be applied further in clinically, challenging obstacles remain, among them: the short half time of the injected growth factor injected is the major one. The short half time makes high dosage or repeated injections necessary. Therefore designing a good delivery vehicle becomes critical for the success of the growth factor therapy. An optimal vehicle is thought to be biocompatible and biodegradable by itself. In addition it has to be able to protect growth factors from proteolytic degradation, control their release from the vehicle and also retain their bioactivity.

In this example, we used a biocompatible polycation to interact with heparin and formed a ternary complex with the growth factor bearing high or low heparin-binding ability. The system was examined for its ability to control the release and sustain the bioactivity of the growth factor.
Methods
Synthesis of PEAD—t-BOC protected aspartic acid (t-BOC Asp), t-BOC protected arginine (t-BOC-Arg) (EMD Chemicals, NJ), ethylene glycol diglycidyl ether (EGDE), trifluoroacetic acid (TFA) (TCI America, OR), anhydrous 1,4-dioxane and tetra-n-butylammonium bromide (TBAB) (Acros organics, Geel, Belgium), dicyclohexylcarbodiimide (DCC), N-hydroxysuccinimide (NHS) (Alfa Aesar, MA) and 4-dimethylaminopyridine (DMAP) (Avocado Research Chemicals Ltd, Lancaster, UK) were used for PEAD synthesis without purification.

The synthesis of PEAD was performed as follows. EGDE and t-BOC Asp were polymerized in 1,4-dioxane under the catalysis of TBAB. t-BOC protection was later removed by TFA to generate primary amine. t-BOC-Arg was conjugated by DCC/NHS/DMAP coupling followed by the second deprotection to yield PEAD. The chemical structure was confirmed using NMR and FT-IR. The molecular weight of PEAD was measured by PL-GPC 50 Plus-RI equipped with a PD 2020 light scattering detector (Varian, Mass.). Two Meso-Pore 300×7.5 mm columns and 0.1% of LiBr in DMF were used as solid phase and mobile phase, respectively.

zeta potential measurement—All polymer solution was prepared in pure water at the concentration of 1 mg/ml. 100 μl of heparin (Alfa Aesar, Mass.) solution was mixed with different volume of PEAD solution. The mixture was diluted in 1 ml of water then 750 μl of solution was taken for the measurement. Zeta potential was measured by Zetasizer Nano Z (Malvern, Mass.). The results showed the average of measurement (n=30).

Dimethylmethylene blue assay—Dimethylmethylene blue (DMB) has been used for quantification of sulfated glycosaminoglycan in the solution (de Jong, J. G., R. A. Wevers, et al. (1989). "Dimethylmethylene blue-based spectrophotometry of glycosaminoglycans in untreated urine: a rapid screening procedure for mucopolysaccharidoses." *Clinical Chemistry* 35(7): 1472-1477 and DeBlois, C., M.-F. Côté, et al. (1994). "Heparin-fibroblast growth factorfibrin complex: in vitro and in vivo applications to collagen-based materials." *Biomaterials* 15(9): 665-672). Briefly, 20 μl of heparin solution (1 mg/ml) was mixed with different volume of PEAD solution (1 mg/ml). H$_2$O was added to the complex solution to let the final volume become 200 μl. After centrifuge at 13,400 rpm for 5 min, 50 μl of supernatant was taken to interact with DMB working solution, 10.7 μg of 1,9-dimethylmethylene blue chloride (Polysciences, PA) in 55 mM formic acid. A series of standard solutions containing known concentrations of heparin were used to make a standard curve. The absorbance at 520 nm was determined.

Scanning electron microscopy—The SEM samples were prepared by mixing PEAD with heparin (mass ratio 5) to form the complex. The complex were dropped on an aluminum stub, sputtered with gold then viewed with Leo 1530 SEM (10 kV, 3 nm spot size).

Growth factor loading efficiency—PEAD and heparin were dissolved in saline to prepare 10 mg/ml solution. 100 or 500 ng of the unlabeled growth factor was mixed with the 125I-labeled growth factor followed by addition of 10 μl of heparin solution then 50 μl of PEAD solution. The growth factor loaded PEAD/heparin complex was precipitated by centrifugation at 13,400 rpm for 5 min. The supernatant was collected for radioactivity measurement by the gamma counter.

For loading efficiency determined by enzyme-linked immunosorbent assay (ELISA), two different methods were adopted, indirect and sandwich ELISA. For FGF-2, PEAD/heparin-complexed FGF-2 was coated onto a 96-well plate for overnight. An anti-FGF-2 polyclonal antibody (Pepro-Tech, NJ) was used for recognition. For NGF, a sandwich ELISA was conducted using NGF Emax® ImmunoAssay Systems (Promega, WI).

Growth factor release profile—After the removal of the supernatant for testing the loading efficiency, 500 μl of saline was added to cover the pellet. At different time points (day 1, 4, 7, 14, 19, 28, 33 and 42), the supernatant was collected and fresh saline was filled again. The radioactivity of the collected supernatant was measured to determine the amount of the growth factor released.

FGF-2 bioactivity—FGF-2 bioactivity was determined by its stimulation of human aortic endothelial cells (HAECs) proliferation. Briefly, HAECs were cultured on a 24-well plate with MCDB 131 containing 10% fetal bovine serum (FBS), 1% L-glutamine and 50 pg/ml ascorbic acid. A cell culture insert (BD Biosciences, MA) with pore size 1.0 μm was placed on each well. Bolus FGF-2 or PEAD/heparin-complexed FGF-2 100 ng was added into the insert (Chen, P.-R., et al. (2005). "Release characteristics and bioactivity of gelatin-tricalcium phosphate membranes covalently immobilized with nerve growth factors." *Biomaterials* 26(33): 6579-6587). Endothelial cell (EC) culture supplement (Sigma, MO) included 1 ng/ml epithelial growth factor (EGF), 2 ng/ml FGF-2, 2 ng/ml insulin-like growth factor-1 (IGF-1), 1 ng/ml vascular endothelial growth factor (VEGF) and 1 μg/ml hydrocortisone. After culturing for 4 days, the proliferation of HAEC was determined by CyQuant Cell Proliferation Assays (Invitrogen, CA). All results were normalized to the control group which has no supplemental growth factors.

NGF bioactivity—NGF bioactivity was determined by its stimulation of the differentiation of PC-12 cells. PC-12 cells were maintained in Dulbecco's Modified Eagle Medium (DMEM) supplemented with 1.0% horse serum (HS) and 0.5% FBS. Bolus NGF, heparin-stabilized NGF or PEAD/heparin-complexed NGF 10 ng was added into the cell culture insert. On day 4 and day 7, the phase contrast images were taken. The neurite lengths were measured using NIH ImageJ version 1.42. The longest ten neurites were shown as the average value along with the standard deviation.

Statistical analysis—Student's t-test was used as a statistical tool to analyze the bioactivity of FGF-2 and NGF. p value<0.05 was marked a significant difference. Data represent mean±SD.

Results

Figure 30:
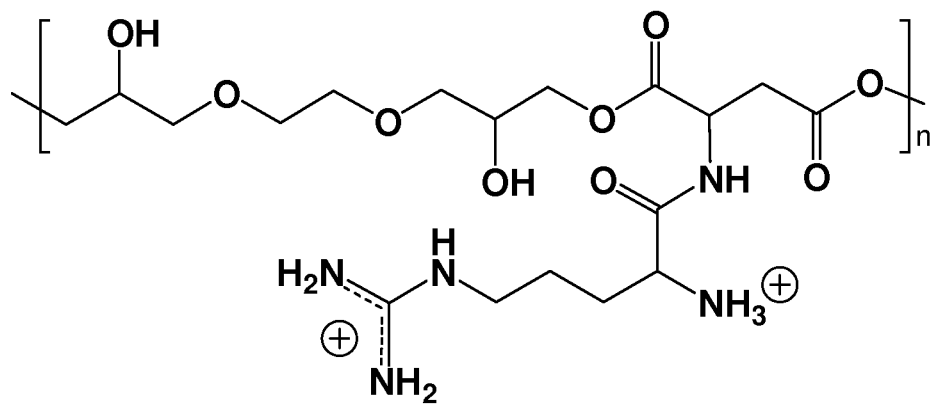
FIG. 30. Chemical structure of poly(ethylene argininylaspartate diglyceride), PEAD FIG. 31. Binding ability of PEAD to heparin (FIG. 31A) zeta potential measurement (FIG. 31B) DMB binding assay FIG. 32. Scanning electron microscopic images of PEAD/heparin complex (FIG. 32A) low magnification (2,000×) (FIG. 32B) high magnification (10,000×).

The synthesis of PEAD initiated from the polycondensation of aspartic acid and ethylene glycol diglycidyl ether (EGDE) followed by the conjugation of arginine which provides positive charges for the polymer. PEAD has +2 charges per monomer at the physiological condition owning to the primary amino group and the guanidinium group of arginine (FIG. 30). The weight-average molecular weight (Mw) is 30,337 Da with polydispersity index (PDI) 2.28.

Figure 31A:
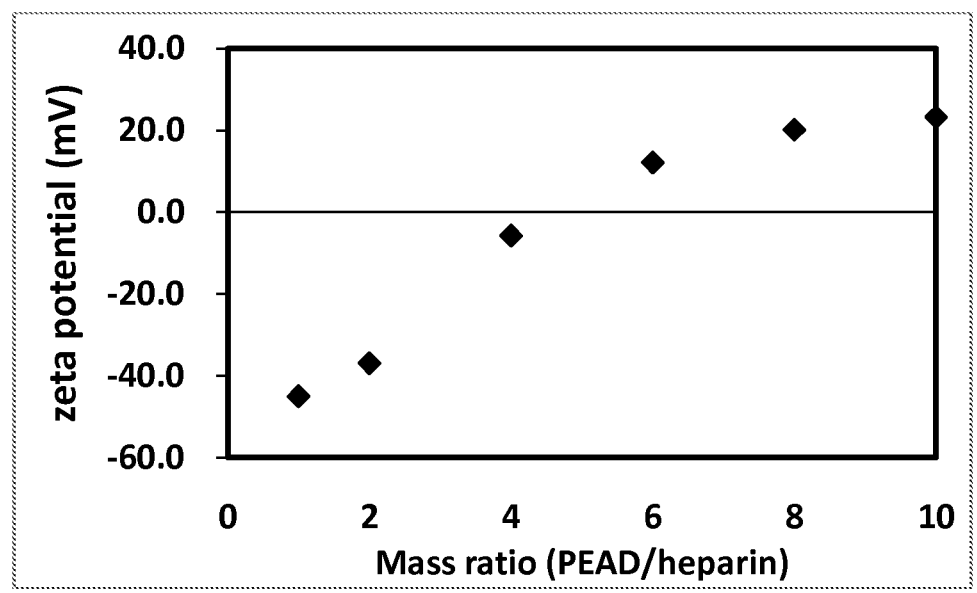

Since PEAD is a positively-charged molecule, addition of PEAD into heparin solution should neutralize the negative charge of heparin and forms PEAD/heparin complex. To test the binding ability of PEAD to heparin, zeta potential measurement was performed. The result (FIG. 31A) shows with the increase of the mass ratio of PEAD to heparin, the zeta potential of the complex shifted from negatively-charged (−45 mV) at ratio 1 to positively-charged (+23.2 mV) at ratio 10. Continuing adding more PEAD did not change the zeta potential and +23.2 mV is close to the zeta potential of PEAD itself. It suggests after ratio 10 the complex was all covered by PEAD. Besides it also shows at ratio 5 PEAD almost neutralized all negative charges of heparin. From the macroscopic observation, below ratio 5 the addition of PEAD let the heparin solution became more turbid and precipitate was seen after a few minutes. Whereas the ratio was over 5, the addition of PEAD would let the solution become clear again.

Figure 31B:
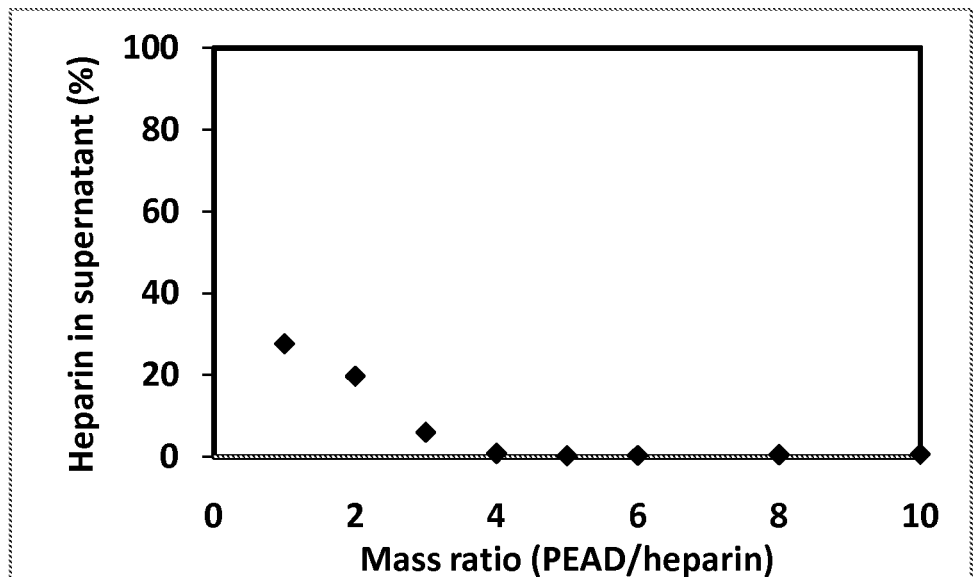

Further confirming the binding ability, we mixed different amounts of PEAD to heparin solutions then precipitated the complex by centrifugation. Because the neutralization of the negative-charged heparin favors the formation of precipitate, we measured the amount of heparin left in the supernatant to determine the binding affinity between PEAD and heparin. For this assay, we applied a heparin binding dye, dimethylmethylene blue (DMB) to detect free heparin by measuring the absorption of DMB at 520 nm. The result (FIG. 31B) shows the amount of heparin in the supernatant was gradually lowered with the addition of PEAD. When the ratio of PEAD to heparin is over 3, >90% of heparin was precipitated through centrifugation. At the ratio 5, that would be >99% of heparin. This result has a good correlation with that of zeta potential measurement because both experiments suggest at ratio 5 PEAD and heparin has the maximum interaction. Therefore this ratio was used for the remaining experiment.

Figure 32A:
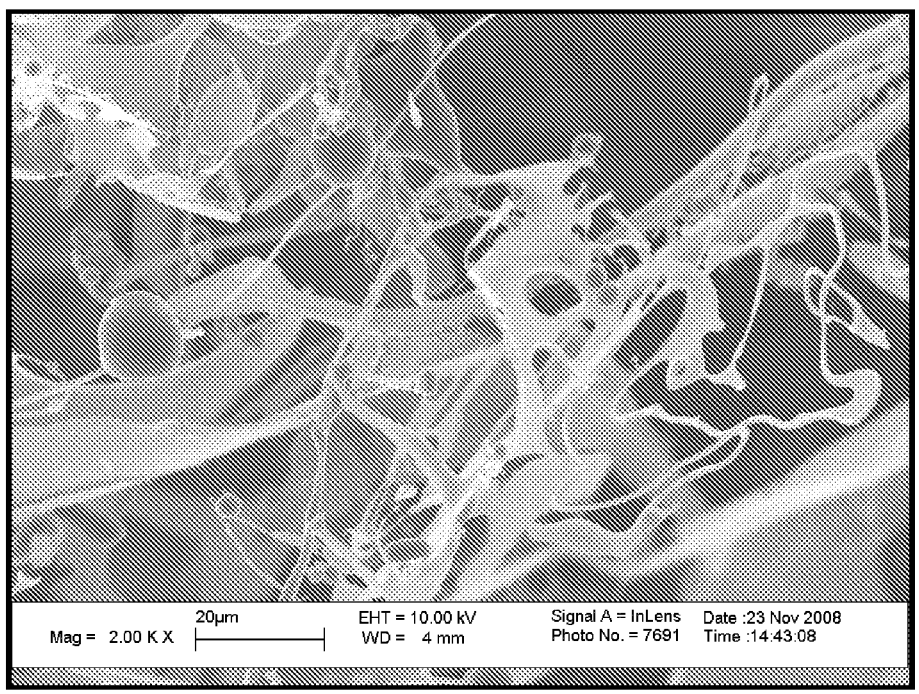
Figure 32B:
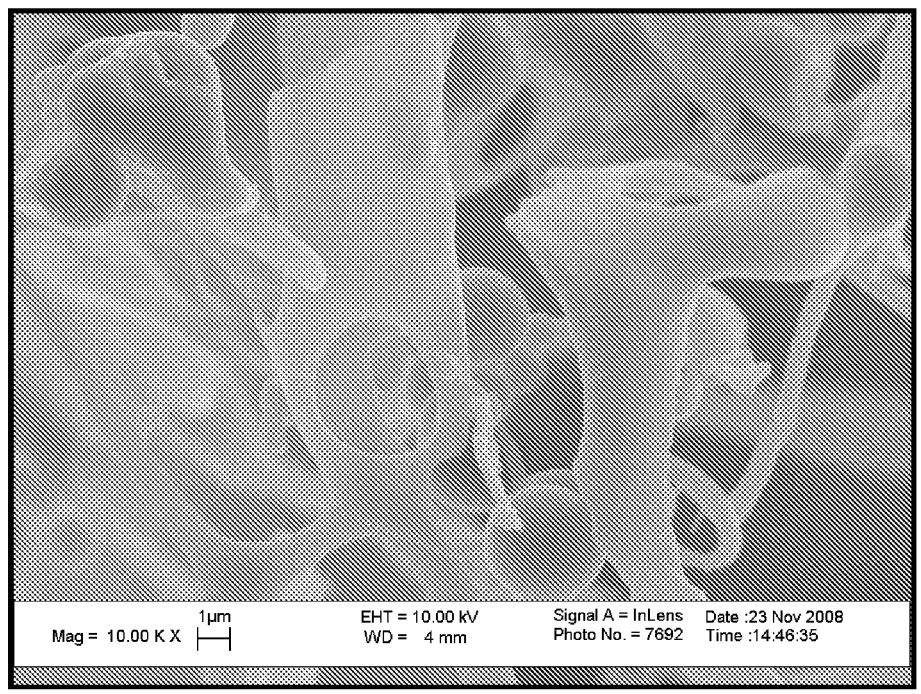

According to the chemical structure, PEAD has a linear backbone connected to positively-charged brushes, arginine, to interact with heparin. To understand the morphology of PEAD/heparin complex, we took pictures under scanning electron microscope (SEM) (FIG. 32). The pictures reveal the morphology of PEAD/heparin complex has fibrous structure with many small globular domains. The diameter of fibers covers a wide range from μm to nm.

Figure 33A:
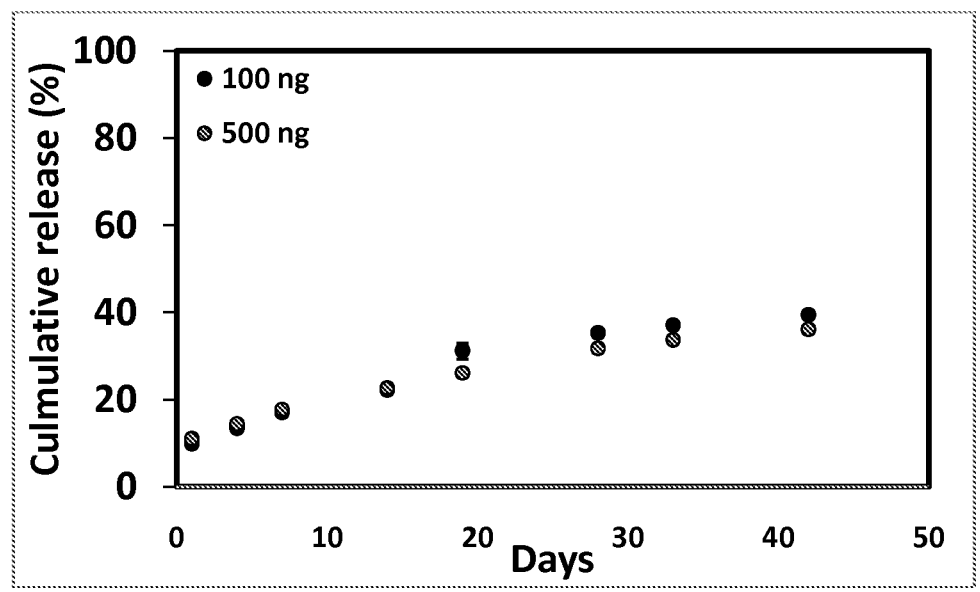
FIG. 33. Release profiles of PEAD/heparin-complexed growth factor (FIG. 33A) FGF-2 (FIG. 33B) NGF.
Figure 33B:
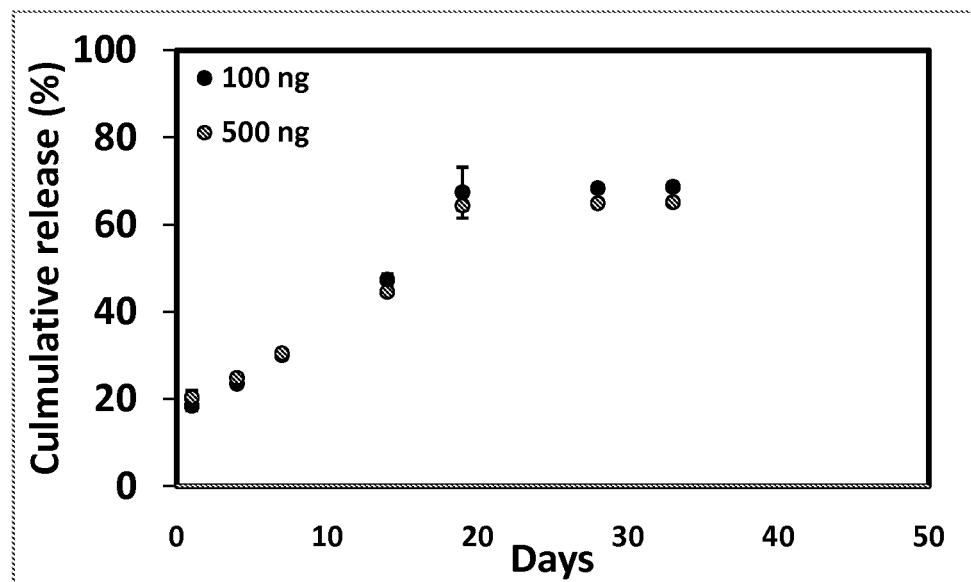

It is understood that a variety of growth factors can bind to heparin with the dissociation constant (Kd) from μM to nM. We propose that PEAD, with its high heparin-binding ability, should be able to incorporate heparin-binding growth factors as well. Hence we began to examine the loading efficiency of growth factors to PEAD/heparin complex. In this experiment 100 or 500 ng of fibroblast growth factor-2 (FGF-2) plus 125I-labeled FGF-2 used as a tracer were mixed with heparin then added into PEAD solution. After staying at room temperature for 2 hr, centrifugation was used to precipitate PEAD/heparin/FGF-2. The amount of unloaded FGF-2 remaining in the supernatant can be determined by a gamma counter. The result (Table 9) shows PEAD/heparin loaded ~68% of FGF-2 for both high and low amounts of FGF-2. The other growth factor, NGF, the release (FIG. 33B) is clearly faster. The initial burst reached almost 20%. The release sustained till day 20 and reached a plateau corresponding to ~30% of the loaded NGF.

TABLE 9

Loading efficiency determined by radioactivity measurement

|  | AVE (%) | STDEV (%) |
| --- | --- | --- |
| 100 ng FGF-2 | 68.87 | 0.15 |
| 500 ng FGF-2 | 67.68 | 0.30 |
| 100 ng NGF | 60.64 | 1.08 |
| 500 ng NGF | 53.63 | 0.15 |

In addition to the method above, enzyme-linked immunosorbant assay (ELISA) is also a common method used to examine the loading efficiency. Here, after PEAD/heparin/FGF-2 formation, this solution was coated onto the plate for overnight. An anti-FGF-2 polyclonal antibody was later applied for detection. The result (Table 10) shows when FGF-2 was added into PEAD/heparin complex, less than 99% of FGF-2 can be detected by the antibody. For NGF, a sandwich ELISA was applied for the experiment. A NGF-specific monoclonal antibody was coated on the plate first followed by PEAD/heparin/NGF incubation. Another anti-NGF antibody was then added for detection. Similar as the result of FGF-2, less than 98% of NGF can be detected by ELISA. Combined the results of radioactivity, we appreciate when either FGF-2 or NGF was loaded into PEAD/heparin complex; more than half percent of FGF-2 or NGF would be precipitated down and formed the pellet after centrifugation. However even for the growth factor not precipitated, it should not maintain in a free form but bind to heparin or PEAD/heparin. Consequently, it cannot be recognized by the antibody.

TABLE 10

Loading efficiency determined by ELISA

|  | Ave (%) | STDEV (%) |
|---|---|---|
| 100 ng FGF-2 | 99.99 | 2.8E−05 |
| 100 ng NGF | 99.98 | 0.0038 |

Once FGF-2 or NGF was loaded into PEAD/heparin complex, the bulk solution was filled, collected and refilled at different time points. The radioactivity of the collected solution was used to calculate the amount of growth factor released from PEAD/heparin and generate the release profile. For FGF-2, the result (FIG. 33A) shows an initial burst of ~10% of release after the first day. Thereafter, the release was close to linear and sustained for six weeks. After six weeks, PEAD/heparin still contained ~30% of FGF-2. For the higher dosage of FGF-2, the release was slower, but there is no huge difference. The other growth factor, NGF, the release (FIG. 33B) is clearly faster. The initial burst reached almost 20%. The release sustained till day 20 and reached a plateau which contained ~30% of loaded NGF.

Figure 34:
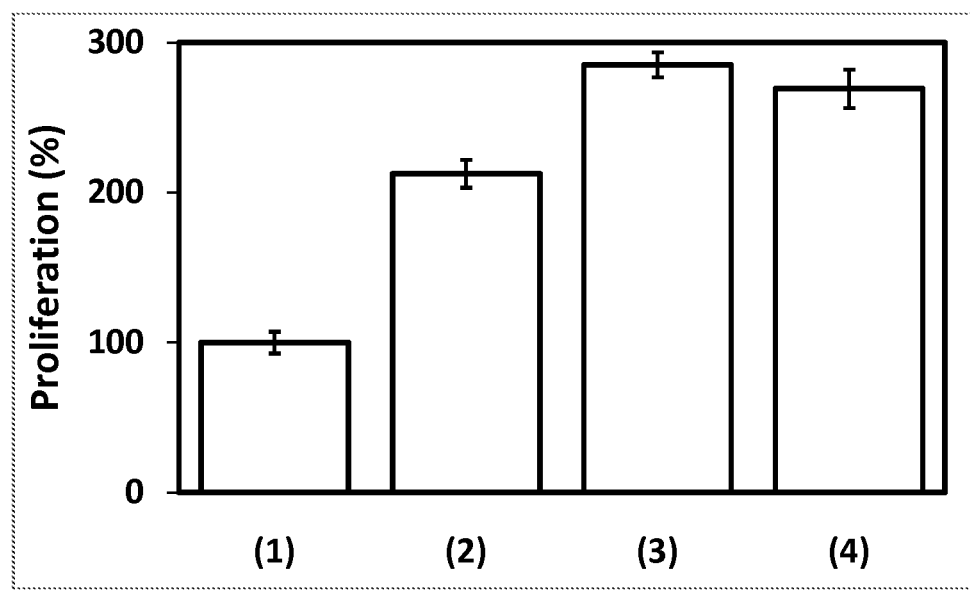
FIG. 34. HAECs proliferation promoted by FGF-2: (1) control, (2) EC culture supplement, (3) bolus FGF-2 and (4) PEAD/heparin-complexed FGF-2.

The loading efficiency and release profile indicated PEAD/heparin complex has good affinity toward the growth factors. To support this system can be applied for growth factor delivery furthermore, we tested the bioactivity of the growth factor released from the complex. For FGF-2 bioactivity, the proliferation of human aortic endothelial cells (HAECs) was compared between the control which is no supplemental growth factors, bolus FGF-2, PEAD/heparin-complexed FGF-2 and endothelial cell (EC) culture supplement which contained low concentrations of epithelial growth factor (EGF), FGF-2, insulin-like growth factor-1 (IGF-1), vascular endothelial growth factor (VEGF) and hydrocortisone. In this experiment HAECs were cultured on the lower chamber and different conditions of FGF-2 or supplement was added in a cell culture insert. If FGF-2 released from PEAD/heparin complex was still bioactive, it would pass through the pore of the insert to promote HAEC proliferation. The result (FIG. 34) which was 4 days' culture shows both bolus FGF-2 and complexed FGF-2 had higher proliferation than the control and EC culture supplement. The proliferation of complexed FGF-2 was 2.69 fold of that of control and 1.26 fold of that of EC culture supplement. Noteworthily, there is no statistical difference between bolus FGF-2 and PEAD/heparin-complexed FGF-2.

Figure 35A:
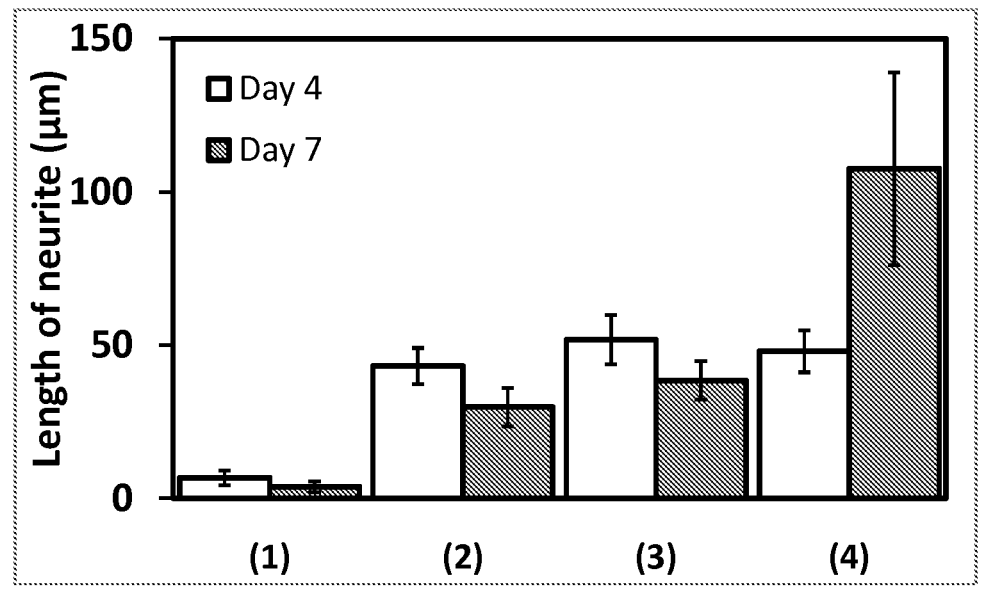
FIG. 35. PC-12 differentiation stimulated by NGF: (1) control, (2) bolus NGF, (3) heparin-stabilized NGF and (4) PEAD/heparin-complexed NGF (FIG. 35A) quantification of neurite lengths (FIG. 35B) phase contract images after 7 days.
Figure 35B:
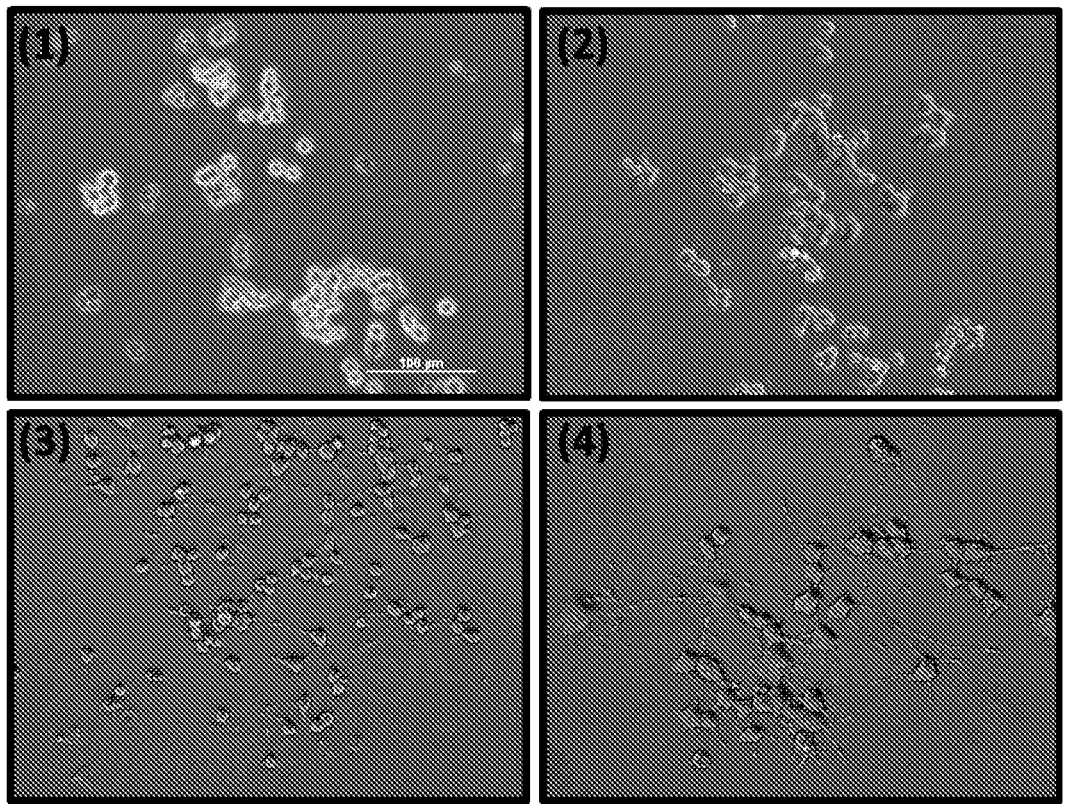

For the bioactivity of NGF, a common cell line, PC-12 cells, was chosen as a model in this study. With the stimulation of NGF, PC-12 cells would start differentiation and grow neurites. Therefore, the lengths of neurites were utilized as an index for determining the bioactivity. The study included four groups, control which was no NGF, bolus NGF, heparin-stabilized NGF and PEAD/heparin-complexed NGF. The result (FIG. 35A) shows after 4 days culture, all three experimental groups had significant longer neurites than the control group. Among them, heparin-stabilized NGF had the longest neurite length. Complexed NGF had the neurite length between bolus and heparin-stabilized NGF but shows no statistical difference with those two. Continue observing till one week, we found even prominent differences between each group (FIGS. 35A and 35B). The control group still had the shortest neurite length. However for bolus NGF and heparin-stabilized NGF, the neurite lengths all became shorter compared with 4 days' culture. PEAD/heparin-complexed NGF, on the contrary, continued stimulating the neurite growth and reached over double length of 4 days' culture (48 μm vs. 108 μm). This result reveals PEAD/heparin-complexed NGF has higher bioactivity for long term culture.

Discussion

Growth factor therapy holds great potentials in biomedicine. However, questions of how to deliver the growth factor to the target site, control its release and maintain its bioactivity make design of a suitable vehicle very challenging. In our study, we used a new polycation, PEAD, to interact with heparin and heparin-binding growth factors as a delivery system. Compared with many existing polycations, PEAD has high in vitro and in vivo biocompatibility, which supports its potential for biological aspects (Fischer, D., Y. X. Li, et al. (2003). "In vitro cytotoxicity testing of polycations: influence of polymer structure on cell viability and hemolysis." *Biomaterials* 24(7): 1121-1131). The monomer of PEAD containing a primary amino group and a guanidinium group has +2 charges at the physiological condition; therefore it has strong binding affinity with heparin which has the highest negative charge density among biomolecules. Utilizing zeta potential measurement and DMB binding assay, we determined the maximum interaction between the two molecules is at PEAD to heparin mass ratio equals to 5. Lower or higher than this ratio would bring the complex extra net charges. Since the two molecules have the maximum interaction, we believe the complex should be more stable than the complexes formed by other mass ratios. Therefore, this ratio was used for the incorporation of the growth factors in the remaining experiments.

Using PEAD/heparin as a delivery vehicle, heparin-binding growth factors were successfully loaded into the complex. Two growth factors with different heparin-binding ability were examined here. FGF-2 is a well known for its high affinity toward heparin (Kd 39 nM), whereas the affinity of NGF to heparin is much lower (Sakiyama-Elbert, S. E. et al. (2000). "Controlled release of nerve growth factor from a heparin-containing fibrin-based cell ingrowth matrix." *Journal of Controlled Release* 69(1): 149-158). Here, the affinity clearly reflects their individual loading efficiency to PEAD/heparin. FGF-2 showed higher loading efficiency into PEAD/heparin complex than NGF. Further, the release of FGF-2 was significantly slower than that of NGF. Therefore, we believe when different kinds of heparin-binding growth factors are encapsulated into PEAD/heparin complex, both the loaded amount and the release trend may follow their affinity to heparin. Growth factors with higher affinity would be loaded more and stay longer as well. In addition, for both FGF-2 and NGF, the amounts (100 ng or 500 ng) of growth factors did not change the release profiles obviously. Therefore, we should be able to propose at this combination of PEAD/heparin complex at least 500 ng of the growth factor can be delivered. In the future, even higher amount of the growth factor can also be added to test the loading capacity of PEAD/heparin complex. By the way, from the viewpoint of polymer synthesis, the molecular weight and charge density of PEAD can be altered easily; therefore it affinity with heparin can also be tailored. The affinity between PEAD and heparin is believed to adjust the loading and release of the growth factor as well.

In addition to loading experiment done by the measurement of radioactivity, we also used ELISA to detect the biological state of FGF-2 and NGF. We found for both cases the antibody was not able to recognize either FGF-2 or NGF after it was added into PEAD/heparin complex. Here we performed two different kinds of ELISA experiments in order to avoid the bias and compare the results. The failure of recognition by the antibody may support the possibility that the growth factor was completely encapsulated or shielded by heparin or PEAD/heparin complex.

In order to test if PEAD/heparin can maintain the bioactivity of the growth factor, we showed PEAD/heparin-complexed FGF-2 promoted HAECs proliferation to the same level as bolus FGF-2. Since the population of HAECs already reached confluence, we stopped growth factor incubation after 4 days. If we follow the release profile, we would appreciate not all complexed FGF-2 was released to promote HAECs proliferation. Therefore, compared to bolus FGF-2, PEAD/heparin-complexed FGF-2 might not reach its highest efficacy. Actually, when we compared PC-12 differentiation stimulated by NGF, the result clearly supports that PEAD/heparin-complexed NGF has higher bioactivity than bolus or heparin-stabilized NGF. Here, we saw the effect at 7 days' culture instead of 4 days'. We also found for both bolus and heparin-stabilized NGF the neurite lengths of 7 days' culture were all shorter than those of day 4's. We anticipate over 7 days the neurite lengths will keep shortening for these two groups. However for complexed-NGF, it is very likely the neurites will continue growing.

Three possible mechanisms support the high bioactivity of PEAD/heparin-complexed growth factors. First, the growth factor was released in a controlled fashion and can stimulate target cells for longer time. Second, PEAD/heparin complex encapsulates the growth factors and can protect the growth factors from being degraded by protease in the culture medium. Therefore it prolongs the half time of the growth factors. Last, the binding of the growth factors to PEAD/heparin complex concentrates the growth factors in the medium, and consequently more growth factors can stimulate the target cells simultaneously.

Heparin has been widely used for growth factor delivery due to its high affinity to a variety of growth factors. For example, Tae, G. et al. functionalized heparin with hydroxybenzotriazole (HObt) to crosslink with polyethylene glycol (PEG) to form a hydrogel (Tae, G., M. Scatena, et al. (2006). "PEG-cross-linked heparin is an affinity hydrogel for sustained release of vascular endothelial growth factor." *Journal of Biomaterials Science-Polymer Edition* 17(1-2): 187-197). Nilasaroya, A. et al. modified heparin with glycidyl methacrylate then photopolymerized with PEG dimethacrylate (Nilasaroya, A., L. A. Poole-Warren, et al. (2008). "Structural and functional characterisation of poly(vinyl alcohol) and heparin hydrogels." *Biomaterials* 29(35): 4658-4664). Seal, B. L. et al. attached a heparin-binding sequence to PEG arms in order to interact with heparin (Seal, B. L. and A. Panitch (2003). "Physical polymer matrices based on affinity interactions between peptides and polysaccharides." *Biomacromolecules* 4(6): 1572-1582). Similarly, Rajangam, K. et al. used self-assembly nanofiber bearing heparin-binding sequence to bind heparin on the surface of nanofiber (Rajangam, K., H. A. Behanna, et al. (2006). "Heparin binding nanostructures to promote growth of blood vessels." *Nano Letters* 6(9): 2086-2090). The advantage of the last two methods is that heparin was not modified but interacted with the target directly. The bioactivity of heparin is likely well preserved. Here, PEAD interacted with heparin directly without modification as well. In addition, because of the high biocompatibility of PEAD, high amounts of heparin and heparin-binding growth factors can be easily incorporated through increasing the amount of PEAD. Finally, PEAD/heparin-complexed growth factors are solution-based and hence injectable. Once the formation of precipitate at the injected site, the micro- to nano-metered structure may keep the growth factor remain for controlled release.

In conclusion, a new biocompatible polycation, PEAD, shows high affinity to heparin. Through this affinity PEAD/heparin complex was tested its ability for being a growth factor delivery vehicle. We showed PEAD/heparin could control the release of the growth factor. Furthermore, PEAD/heparin-complexed growth factors can preserve equal or superior bioactivity compared to bolus growth factors.

Example 7

Enhancement of Angiogenesis and Vascular Maturity Via an Injectable Delivery Matrix Enhancing the maturity of newly formed blood vessels is a critical factor determining the success of therapeutic angiogenesis. The maturation of vasculature relies mainly on the sustained stabilization of endothelium by mural cells. Here, an injectable delivery matrix, [polycation:Heparin:FGF-2], is employed to stimulate nascent vessel formation. At very low dosage of FGF-2, the delivery matrix was able to elicit comprehensive angiogenic phenomena. In addition to the significant increase of endothelial cells and hemoglobin, the histological analysis revealed that the mural cells were highly involved throughout the neovasculaturization. For the short term, the delivery matrix recruited pericytes to interact with endothelial cells. For the long term, it enhanced the functions of smooth muscle cells to support the nascent blood vessels. This strategy potentially provided a new option for therapeutic angiogenesis.

Angiogenesis is a physiological process involving the formation of nascent vasculature from existing blood vessels. The complex interaction between two distinctive cell types composing vascular walls, endothelial cells and mural cells, are highly coordinated by different signals. From the perspective of therapeutics, promoting angiogenesis is intriguing because it provides potential treatments for many human diseases especially coronary and peripheral ischemia. Among the approaches to stimulate blood vessel formation, delivery of growth factors is a promising one because it can avoid the immunogenicity of viral vectors used in angiogenic gene therapy and also the difficulty and variation of cell sources applied in cell therapy. However, current strategies do not allow the long term efficacy of the delivered growth factors. High dosage or repeated administration which is required to sustain angiogenic processes and also stabilize the newly formed blood vessels makes it clinically unpractical. Controlled delivery provides a solution for this obstacle by prolonging the release of the growth factors. Therefore development of optimal delivery vehicles now becomes a critical issue for the success of therapeutic angiogenesis.

In the natural environment, most secretory growth factors do not reside in a free form but are associating with extracellular matrix including glycosaminoglycans (GAGs). All GAGs are negatively charged linear polysaccharides but can have different composition, function and distribution in the animal body. GAGs have a fundamental function of providing substratum for cell attachment, but their interaction with growth factors also involves in many biological processes such as development and cancer progression. Among GAG components, heparin/heparan sulfate (HS) are well studied for their high affinity to a variety of growth factors including epithelial growth factor (EGF), fibroblast growth factor (FGF) and vascular endothelial growth factor (VEGF) families. The interaction involved is able to modulate the conformation of the growth factor (Aviezer D, et al. (1994) Differential structural requirements of heparin and heparan-sulfate proteoglycans that promote binding of basic fibroblast growth-factor to its receptor. J Biol Chem 269(1):114-121 and Moy F J, et al. (1997) Properly oriented heparin-decasaccharide-induced dimers are the biologically active form of basic fibroblast growth factor. Biochemistry 36(16):4782-4791), protect it from proteolytic cleavage (Saksela O, Moscatelli D, Sommer A, & Rifkin D B (1988) Endothelial cell-derived heparan-sulfate binds basic fibroblast growth-factor and protect it from proteolytic degradation. J Cell Biol 107 (2):743-751) and enhance its bioactivity (Park J E, Keller G A, & Ferrara N (1993) Vascular endothelial growth-factor (VEGF) isoforms—differential deposition into the subepthelial extracellular-matrix and bioactivity of extracellular matrix-bound. Mol Biol Cell 4(12):1317-1326). Incorporation of heparin/HS in the delivery vehicle is therefore a reasonable and promising approach to preserve the original property of the delivered growth factors.

Here, a polycation, poly(ethylene argininylaspartate diglyceride) (PEAD), heparin and a potent angiogenic factor, FGF-2, are employed to form a delivery matrix, [PEAD:Heparin:FGF-2]. Our underlying hypothesis is that charge interaction between PEAD and heparin can well preserve the original property of heparin and maximize its affinity to heparin-binding factors compared to covalent modification of heparin on the materials. When the growth factor is released from the delivery matrix, heparin can also protect the growth factor from proteolysis and maintain its bioactivity. In vitro results have pointed out by this approach the efficacy of the growth factors was well preserved or even enhanced compared to naked growth factors. Here, we further demonstrated this delivery matrix was able to stimulate neovascularization from multiple aspects from quantity, quality to functionality.

Materials and Methods

Synthesis of PEAD—PEAD was synthesized essentially as described in Example 6. The chemical structure was characterized using an UltraShield Plus 600 NMR (Bruker BioSpin) and a Nicolet iS10 spectrometer (Thermo Fisher Scientific).

Delivery vehicle preparation and scanning electron microscopy—For preparation of the delivery vehicle, PEAD dissolved in the deionized water was mixed with heparin solution under the stirring condition. The complex was dropped on an aluminum stub, lyophilized, sputtered with gold, and the morphology was viewed with a Jeol 9335 field emission gun SEM (Jeol).

Western blotting—Both PEAD and heparin were dissolve in normal saline (0.9% $NaCl_{aq}$) to prepare the concentration of 10 mg/ml. For preparation of the delivery matrix, 500 ng of FGF-2 was first mixed with 10 μl of heparin solution and then 50 μl of PEAD solution. 20× of normal saline and deionized water were used to adjust the desired ionic strength to obtain the delivery vehicle in 1×, 2× and 5× of saline. The delivery matrix was equilibrated at room temperature for 15 min followed by the centrifugation at 12,100 g for 10 min. The supernatant was collected, mixed with the common sample buffer and denatured at 95° C. for 5 min. 15% of sodium dodecyl sulfate polyacrylamide gel electrophoresis (SDS-PAGE) was utilized for separation followed by protein blotting on a polyvinylidene fluoride (PVDF) membrane. A rabbit anti-human FGF-2 polyclonal antibody (Peprotech) was applied for recognition followed by a secondary horse peroxidase conjugated anti-rabbit IgG antibody (Sigma).

Tube formation of HUVECs in fibrin gel—HUVECs (Lonza) were maintained in EGM-2 basal medium supplemented with growth factors according to the instruction. For tube formation, $8 \times 10^4$ cells (passage 7) were mixed with fibrinogen solution containing FGF-2 (100 ng) or the same amount of FGF-2 in the delivery matrix. After addition of thrombin, the whole solution was gelled at 37° C. for 30 min. The gel was last overlaid with 600 μl of the basal medium to provide the basic nutrient. After incubation for 3 days, the phase contrast images were taken by an inverted microscope Eclipse Ti (Nikon).

Animal care and subcutaneous injection—Under isoflurane anesthesia, 65 μl of saline, the delivery vehicle (500 μg of PEAD and 100 μg of heparin), the bolus FGF-2 (500 ng of FGF-2) or the delivery matrix (500 μg of PEAD, 100 μg of heparin and 500 ng of FGF-2) was subcutaneously injected in the left back of Male Balb/cJ mice with an average age of 6-7 weeks. The right back which did not receive injection was later utilized as the contralateral site. All groups contained 4 to 8 mice.

Hemoglobin quantification—The animals were sacrificed at post-injection week 1, 2 and 4. The subcutaneous tissue having a dimension of 1.5 cm×1.5 cm was harvested at the injection site and the contralateral site. The hemoglobin in the harvested tissue was extracted by addition of in 500 μl of the hemolysis buffer containing 17 mM of Tris-HCl (pH 7.4) and 0.75 wt % ammonium chloride and incubation for 24 h. The absorbance at 410 nm corresponding to the hemoglobin Soret band was recorded by a SynergyMX plate reader (Biotek). All values were normalized to the one of the saline injection.

Immunofluorescent analysis—The harvested subcutaneous tissue was embedded and frozen in Tissue-Tek OCT compound (Sakura Finetek USA). Sections of 5 μm thickness were cut with a cryo-microtome and stored at −80° C. For staining CD31-positive cells, a rat anti-mouse CD31 monoclonal antibody (BD Biosciences) was applied first followed by a Cy3-conjugated anti-rat IgG polyclonal antibody. For staining alpha-SMA-positive cells, a FITC-conjugated anti-SMA monoclonal antibody (Sigma) was utilized according to the provided instruction. For vWF-positive cells, a FITC-conjugated anti-vWF antibody was used for staining. All slides were last counterstained with DAPI (Invitrogen). The fluorescent images were taken using a Fluoview 1000 Confocal microscope (Olympus).

Quantification of CD31— and alpha-SMA-positive cells— For the 4-week slides, random fields were chosen for comparison between each condition. The number of CD31- or alpha-SMA-positive cells were counted and confirmed by DAPI-positive nuclei. The value was divided by the area of the tissue and normalized to that of the control group.

Statistical analysis—ANOVA followed by post-hoc Bonferroni test was utilized to compare the number of CD31- and alpha-SMA-positive cells between all conditions. Data is presented as mean±standard deviations. *p value<0.05; **p value<0.01.

Results

Figure 36:
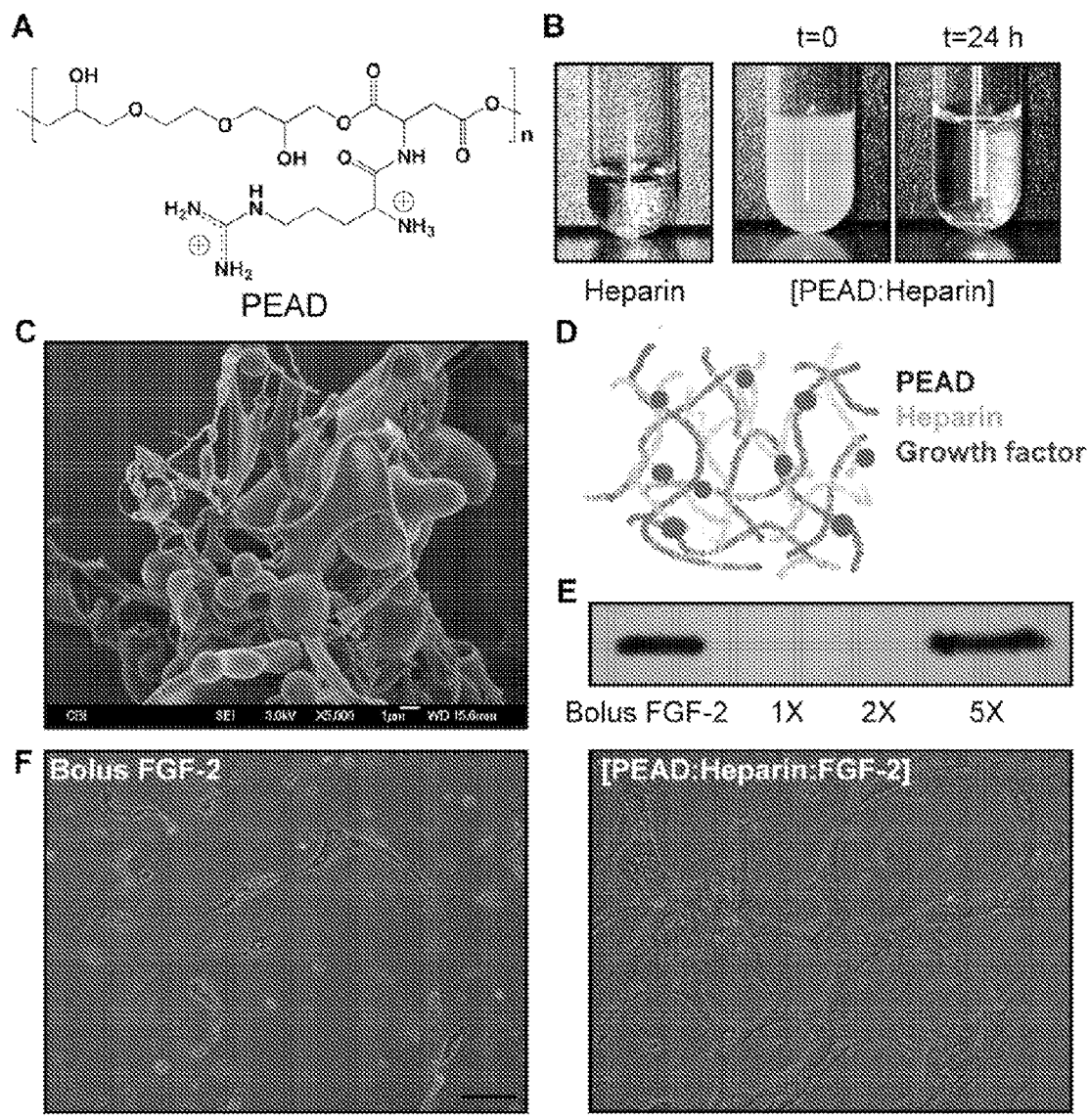
FIGS. 36A-36F.

Interaction between [PEAD:Heparin] and FGF-2—Polycations have many biological applications but their low biocompatibility may compromise the clinical potentials. Solving this problem, we have synthesized new generation of polycaitons. We propose that the polycations composed of natural building blocks and connected by hydrolysable linkage can have better biocompatibility. One biocompatible polycation, poly(ethylene argininylaspartate diglyceride) (PEAD), is composed of aspartyl, arginyl and diglyceride moieties (FIG. 36A). The repeating unit of PEAD is linked by hydrolysable ester bonds. PEAD has advantages including the superior biocompatibility examined by in vitro and in vivo tests. The amino and guanidine groups which are protonated under the physiological condition render PEAD the ability to interact strongly with natural polyanions, such as heparin and hyaluronic acid. Macroscopic observation found that PEAD lowered the solubility of heparin in the aqueous solution by forming [PEAD:Heparin] complex through charge interaction (FIG. 36B). [PEAD:Heparin] complex continued aggregation and sedimented to the bottom of the test tube. The speed of sediment depended on the concentration of the solution and also the mass ratio of individual polymer. Generally, a coacervate was completely formed after 24 h incubation. The coacervate can be resuspended easily and reversed to the turbid state. The microscopic picture revealed that the morphology of the [PEAD:Heparin] complex was mainly composed of globular and fibrous domains (FIG. 36C). The diameters of the domains covered a range from pm to sub-pm. Our prior study examined that the morphology of [PEAD:Heparin] complex was dependent on the mass ratio individual polymer. The globular domains were contributed by heparin whereas the fibrous ones were from PEAD.

Due to the high affinity of heparin to many growth factors, we propose the mechanism that [PEAD:heparin] complex is able to incorporate high amounts of growth factors through their heparin-binding domains (FIG. 36D). With the increase of the ionic strength of the solution, the binding between PEAD, heparin and heparin-binding growth factors is reduced and therefore the growth factors would released from the complex. This hypothesis was later confirmed by the loading experiment of FGF-2 (FIG. 36E). Under normal saline condition (0.9% $NaCl_{(aq)}$), FGF-2 (500 ng) was completely precipitated by [PEAD:Heparin] complex. While increasing the ionic strength to 2 folds of the normal saline did not change the result, 5 folds of the normal saline broke the charge interaction between the polymers and FGF-2. Therefore, [PEAD:Heparin] complex was no longer able to precipitate FGF-2 at this condition.

Comparing the bioactivity of the bolus and the delivery matrix, we applied the established method trapping human umbilical vein endothelial cells (HUVECs) together with the bolus FGF-2 or the delivery matrix. The culture medium was overlaid on the gel to provide necessary nutrients and allow materials exchange. After three days, we observed significant differences between the bolus FGF-2 and the delivery matrix groups (FIG. 36F). The bolus FGF-2 induced very less degree of differentiation of HUVECs. Most cells were rounded and scattered in the gel. On the other hand, in the delivery matrix group, HUVECs completely differentiated and aligned to develop a complex mesh. The result strongly indicated the higher bioactivity of the delivery matrix. We expected the possible mechanism that FGF-2 which had high affinity with heparin was confined in the gel by the [PEAD:heparin] complex. Some of the bolus FGF-2 in the gel, however, had diffused to the overlaid medium and was not able to stimulate cells efficiently.

Figure 37:
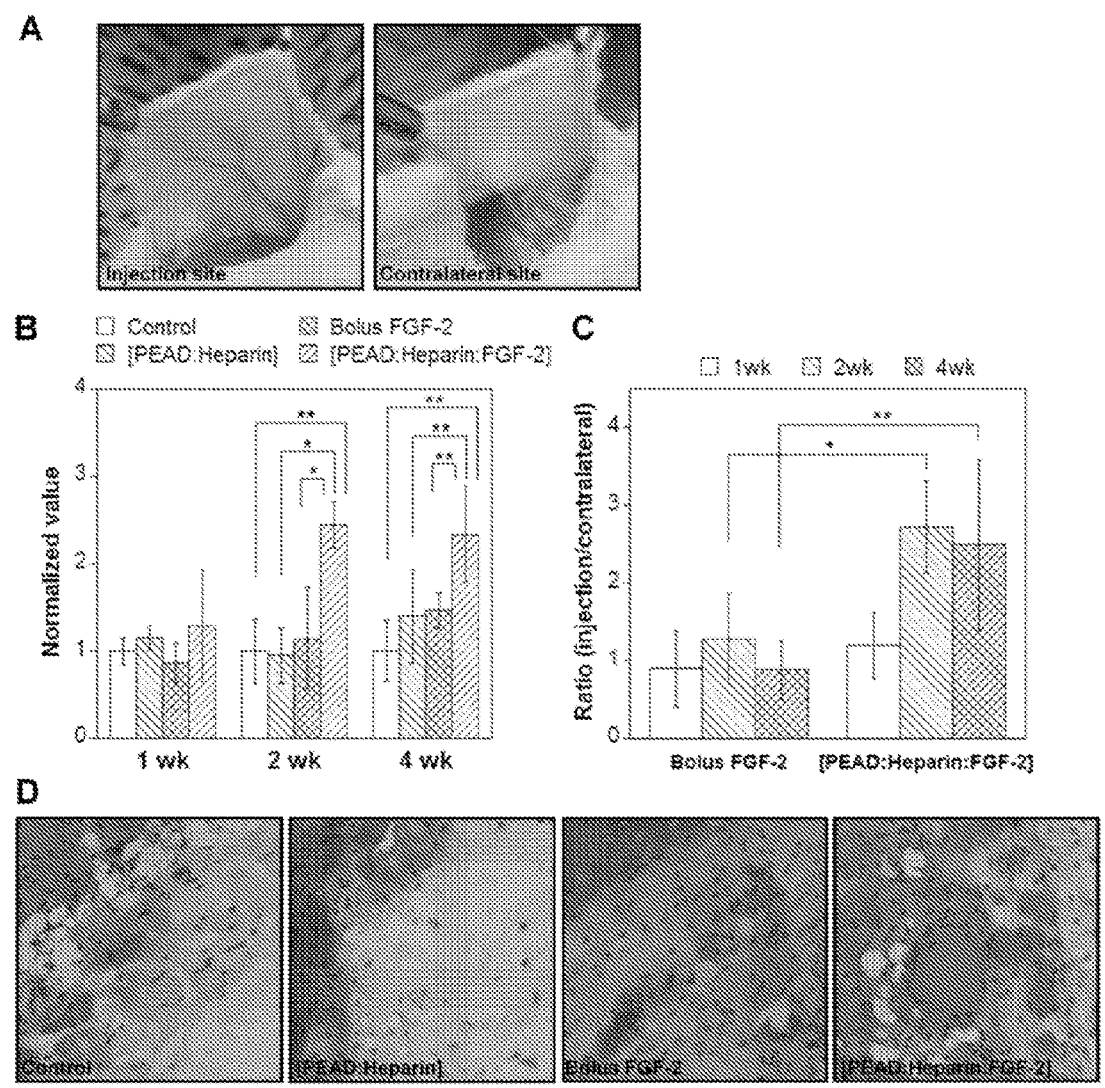
FIGS. 37A-37D (FIG. 37A) Macroscopic observation of subcutaneous tissue showed that delivered matrix clearly induced blood vessel formation at the injection site. 2-week pictures from the same mouse were shown.

[PEAD:Heparin:FGF-2] promotes higher angiogenesis than bolus FGF-2—To examine the in vivo ability of the delivery matrix, we subcutaneously injected the delivery matrix containing 500 ng of FGF-2 in the back of male BALB/cJ mice. The angiogenic effect was compared between the control, the delivery vehicle and 500 ng of FGF-2. Macroscopic observation of the tissue found extensive formation of blood vessels at the injection site whereas the contralateral showed no obvious effect (FIG. 37A). The pictures indicated the efficacy of the delivery matrix to promote angiogenesis and also localize the distribution of FGF-2. Quantitative comparison of the concentration of hemoglobin at three time points revealed that the delivery matrix group had higher amounts of hemoglobin from 2 weeks post-injection (FIG. 37B). On the other hand, the bolus FGF-2 did not have statistical difference with the control and the delivery vehicle groups. After 4 weeks, the delivery matrix group still yielded a significantly higher amount of hemoglobin than other three groups. Possibly it reflected the long term stability of blood vessels or the long term bioactivity of the delivery matrix. Further comparing the ratio of hemoglobin at the injection site and the contralateral site, we found the ratios were significantly larger than 1 after 2 weeks (FIG. 37C). It correlated with the macroscopic observation that the angiogenic activity of the delivery matrix was confined at the injection site. The bolus group, however, had the ratio close to 1 for every time point and was significantly lower than the delivery matrix after 2 weeks.

Hematoxylin and eosin staining revealed the gross appearance of the delivery vehicle and the control groups having similar feature suggesting the delivery vehicle had no angiogenic effect (FIG. 37D). For the bolus FGF-2, we observed cells aggregated together in the hypodermis region. Muscle fibers were also found together with aggregated cells. Yet, clear blood vessel feature was rarely seen in all tissue sections. On the contrary, the delivery matrix showed significant blood vessel formation. Circular and closed pattern of nucleated cells surrounded by the muscle bundles were clearly observed. The lumen of vessel was filled with red cells further supporting the function of the nascent blood vessel.

Figure 38:
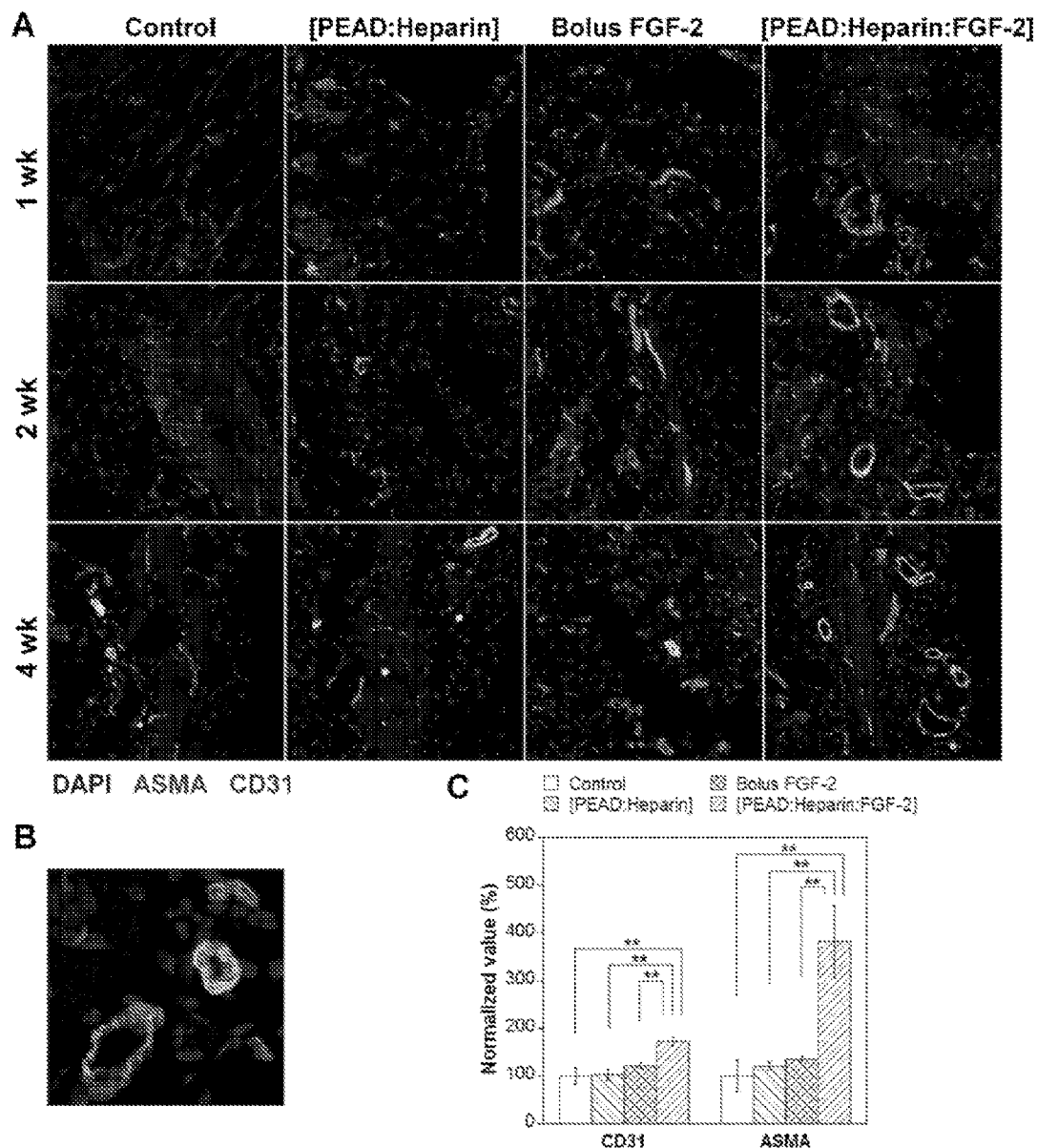
FIG. 38A-38C The delivery matrix induced a higher extent of angiogenesis revealed by immunofluorescent analysis.

[PEAD:Heparin:FGF-2] stimulates proliferation of endothelial cells and mural cells—We later studied the extent of angiogenesis by immunofluorescent analysis. Two specific markers, CD31 and α-smooth muscle actin (alpha-SMA), were stained for the angiogenic effect and maturation of blood vessels induced by the delivery matrix. After 1 week, both the delivery matrix and bolus FGF-2 induced more CD31-positive cells than the control (FIG. 38A). This can be explained by the proliferation of endothelial cells stimulated by FGF-2. On the other hand very low numbers of alpha-SMA-positive cells were observed for all groups. After 2 weeks, higher amounts of endothelial cells can still be found in the delivery matrix and bolus FGF-2 whereas only the delivery matrix induced a significant amount of alpha-SMA-positive cells. In addition, the blood vessels were also well organized as the circular features of endothelial cells lined by the mural cells. These features became more significant after 4 weeks revealed by the number of blood vessels in the field. Compared to the delivery matrix, other three groups had similar features that most endothelial cells were naked without the surrounding of mural cells. The higher magnified micrograph further confirmed the complete structure of blood vessels having a distinctive alignment of endothelial cells and mural cells (FIGS. 38A-38C).

[PEAD:Heparin:FGF-2] induced higher amounts of CD31- and alpha-SMA-positive cells—To get statistical comparison, random fields were chosen for quantifying the number of endothelial cells and mural cells. The result suggested that the delivery matrix increased 72% of the number of CD-31 positive cells of the control, 69% of the number of the delivery vehicle and 41% of that of the bolus FGF-2 (FIG. 38C). All the comparisons were statistically significant with p values lower than 0.01. On the other hand, although the average number of the bolus group was higher, there was not statistical difference with the control and the delivery vehicle groups. Consistent with the qualitative observation, the delivery matrix induced more proliferation of the endothelial cells. More striking difference was the number of alpha-SMA-positive cells. Very few alpha-SMA-positive were found in the field beside the delivery matrix. The quantitative result also pointed that the delivery matrix group was 3.81 folds of that of the control, 3.15 folds of the delivery vehicle and 2.82 folds of the bolus FGF-2. All comparison had p values lower than 0.01. Again no statistical difference was revealed among other three groups. Collectively, both angiogenic markers strongly supported the higher extent of blood vessel formation stimulated by the delivery matrix.

Figure 39:
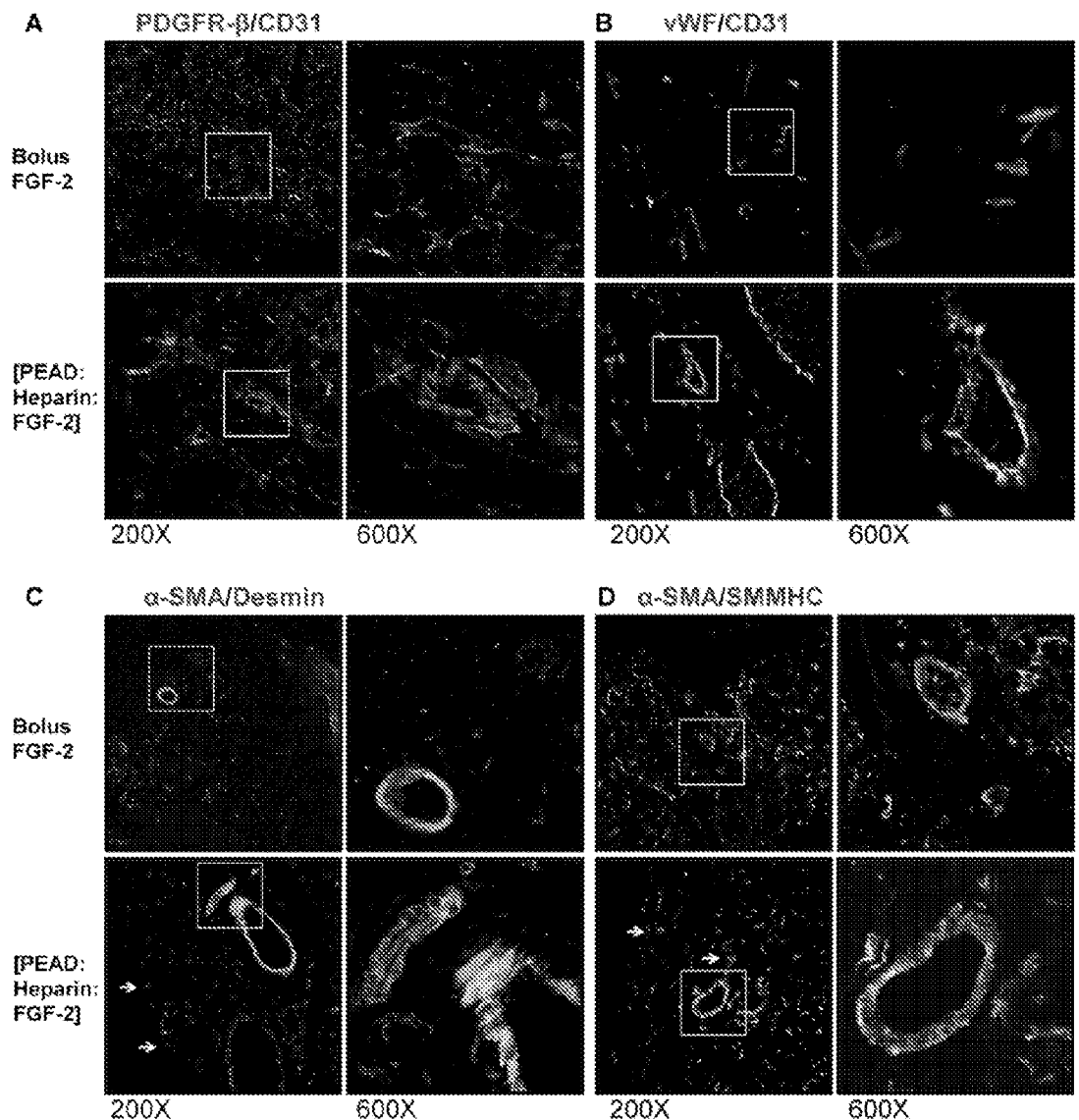
FIG. 39A-39D Enhanced maturity of the nascent blood vessels by the delivery matrix.

[PEAD:Heparin:FGF-2] supports maturity of nascent blood vessels—Further examining the maturity of the newly formed blood vessels induced by the delivery matrix, we stained a series of blood vessel associated markers. Desmin, a component of intermediate filament, is a commonly used marker for mural cells. We observed desmin co-expressed in alpha-SMA-positive blood vessels (FIG. 39C). Additionally, alpha-SMA-negative but desmin-positive blood vessels were also found in the field. It possibly reflected the heterogeneity of pericytes which had low alpha-SMA expression at capillaries (Nehls V et al. (1991) Heterogeneity of microvascular pericytes for smooth muscle type alpha-actin. *J Cell Biol* 113(1):147-154). Von Willebrand factor (vWF) being an important molecule participating in hemostasis was stained to prove the thrombotic ability of the nascent blood vessels. We found that the delivery matrix induced rich expression of vWF (FIG. 39B). The evident overlap of CD31 and vWF signals confirmed the nascent endothelial cells were fully functional. Last, smooth muscle myosin heavy chain (SMMHC) representing the contractibility of smooth muscle cells was co-stained with alpha-SMA to evaluate the functionality of nascent blood vessels. The result indicated the blood vessels induced bolus FGF-2 were smaller and did not have obvious expression of SMMHC even with the ones having abundant expression of alpha-SMA (FIG. 39D). For the delivery matrix, smaller blood vessels did not express SMMHC as was the case of bolus FGF-2, but more importantly, it also contained bigger blood vessels having significant overlap of alpha-SMA and SMMHC.

[PEAD:Heparin:FGF-2] promote stabilization of endothelial cells by pericytes at early stage—The above results support that for the long term the delivery matrix is able to enhance the maturity of the nascent blood vessels especially by increasing the number of smooth muscle cells and enhancing their functions. To investigate its effect to pericytes which are important mediators involving in the early stage of the angigenic process, CD31 was co-stained with the pericyte specific marker, platelet derived growth factor β (PDGFR β) (Lindahl P, et al. (1997) Pericyte loss and microaneurysm formation in PDGF-B-deficient mice. *Science* 277(5323):242-245). We observed after 1 week many CD31-positive endothelial cells clustered with PDGFR β-positive cells in the delivery matrix group whereas no overlap was seen in the bolus FGF-2 group (FIG. 39A). The association supposedly indicated the interaction between pericytes and endothelial cells.

Discussion

Therapeutic angiogenesis via exogenous growth factor has been examined extensively in human ischemic diseases (Laham R J, et al. (1999) Local perivascular delivery of basic fibroblast growth factor in patients undergoing coronary bypass surgery: results of a phase I randomized, double-blind, placebo-controlled trial. *Circulation* 100(18):1865-1871 and Sellke F W et al. (2003) Vascular growth factors and angiogenesis in cardiac surgery. *Ann Thorac Surg* 75(2): S685-690) but so far has not brought satisfactory results (van Royen N, et al. (2009) A critical review of clinical arteriogenesis research. *J Am Coll Cardiol* 55(1):17-25). The treatment groups showed improvement at the early stage but had no significant difference from the placebo group for the long term observation. It clearly indicated that the nascent blood vessels did not have enough stability. Although the idea of stimulating tissue repair or regeneration by administering angiogenic factors is reasonable and promising, difficulty exists in the delivered strategies and maintaining the activity of delivered factors. Currently, two approaches are being applied to solve the obstacles. One is co-delivery of multiple growth factors to boost the long term stability of neovasculature (Cao R, a al. (2003) Angiogenic synergism, vascular stability and improvement of hind-limb ischemia by a combination of PDGF-BB and FGF-2. *Nat Med* 9(5):604-613 and Saif J, et al. (2010) Combination of Injectable Multiple Growth Factor-Releasing Scaffolds and Cell Therapy as an Advanced Modality to Enhance Tissue Neovascularization. *Arterioscler Thromb Vasc Biol* 30(10):1897-1904). The other is improving delivery vehicles to maintain the bioactivity of growth factors. From a different perspective of view, an angiogenic factor like most other growth factors has ability to affect different cells rather than confining its influence to one specific type of cells. It means an individual growth factor is able to stimulate various sorts of cells although the extents can be different. The stimulation allows a wide range of cells to collaborate together to generate tissue, heal the wound or even initiate tumorigenesis. Specifically for FGF-2, the signaling pathway has been studied extensively (Cross M J et al. (2001) FGF and VEGF function in angiogenesis: signalling pathways, biological responses and therapeutic inhibition. *Trends Pharmacol Sci* 22(4):201-207). It is a potent mediator promoting the proliferation, migration and differentiation of endothelial cells. Additionally, the interplay between FGF-2 and PDGF-BB is important for the survival, proliferation and function of mural cells (Millette E, et al. (2005) Platelet-derived growth factor-BB-induced human smooth muscle cell proliferation depends on basic FGF release and FGFR-1 activation. *Circ Res* 96(2):172-179 and Kano M R, et al. (2005) VEGF-A and FGF-2 synergistically promote neoangiogenesis through enhancement of endogenous PDGF-B-PDGFRβ signaling. *J Cell Sci* 118(16):3759-3768). However, if the bioactivity of the administered FGF-2 is not well maintained, its effects would be compromised. High dosage becomes indispensable to booster or sustains these processes.

Here we evaluated the angiogenic activity of our delivery matrix by a simple animal model to avoid the variation caused by the complicated surgery. Consequently, the results provided a solid proof for the efficacy of this novel delivery strategy. Here, we saw a significant increase of the proliferation of both endothelial cells and smooth muscle cells stimulated by the delivery matrix. The evident pattern of blood vessels was observed at 2 weeks post-injection. Further monitoring till 4 weeks, the delivery matrix revealed overwhelmingly higher angiogenic activity than the bolus FGF-2. Enhancing the maturity of the nascent vasculature is currently a target which requires the significant involvement of mural cells. The delivery matrix clearly increased the function of mural cells by promoting the number of mural cells surrounding the nascent blood vessels, upregulating the expression of components associated with maturity including alpha-SMA, desmin, SMMHC and PDGFR 3. The mature vasculature also yielded a higher blood flow determined by the local amount of hemoglobin.

It is worth noting that the dose of FGF-2 we injected was much lower than that of most research groups used. Presumably due to the low dosage, the bolus FGF-2 did not vary significantly between the control and the delivery vehicle. Even though the immunofluorescent staining revealed the bolus FGF-2 may induce more endothelial cells at 1 week post injection, the concentration of hemoglobin was not higher than that of the control and the number had no statistically higher after 4 weeks. This result again implied the importance of the long term efficacy of the angiogenic factor to complete angiogenesis.

Contributed by the great efforts of various research groups, many strategies have been developed to deliver growth factors. Currently, hydrogels, poly(lactic-co-glycolic acid) (PLGA) microspheres and nanofibers are mainstreams adopted for controlled delivery of growth factors. Hydrogels composed of biological materials, such as gelatin and alginate, or synthetic materials, such as poly(ethylene glycol), embed growth factors inside and allow the diffusion-dependent release of growth factors to activate surrounding cells. However, without protection, the released growth factors are naked and therefore are vulnerable to the extracellular proteases. Additionally, the release profile is not easily controlled. The initial burst can reach 50% of the loaded growth factors. PLGA is a highly biocompatible material and have been approved by the Food and Drug Administration. Nevertheless, the incorporation of growth factors requires organic solvents which have high tendency to denature growth factors. The loading efficiency is still unsatisfactory (Wang X, et al. (2007) Silk coatings on PLGA and alginate microspheres for protein delivery. *Biomaterials* 28(28):4161-4169). Even though nanofibers have shown promising in vivo results (Hsieh P C H, et al. (2006) Controlled delivery of PDGF-BB for myocardial protection using injectable self-assembling peptide nanofibers. *J Clin Invest* 116(1):237-248)), the extremely high cost to synthesize peptide may compromise their clinical potentials. As such, we are developing a new formula for growth factor delivery.

Our strategy which applies a biocompatible polycation, heparin and heparin-binding growth factors to form a delivery matrix has shown satisfying effects revealed by in vitro studies and the current in vivo study. We demonstrated the loading efficiency can be extremely high according to the results of ELISA and western blot. We also proposed that the release profiles can be adjusted by tailoring the properties of PEAD especially its charges and size. Corresponding experiments are undergoing to prove this idea. Moreover, this delivery matrix has great potential to be combined with current hydrogel systems for cell-based therapy. Examined by the tube formation of HUVECs here, the delivery matrix not only maintains the viability the cells but also enhances the bioactivity of the incorporated growth factor. We therefore believe the delivery matrix can be mixed with cells and hydrogels and enhance the proliferation or differentiation of the encapsulated cells.

In conclusion, we demonstrated our delivery matrix can maximize the bioactivity of FGF-2 in the angiogenic processes. The nascent vasculature has substantial maturity which is among the most critical elements determining the success of therapeutic angiogenesis. Currently, we are applying this delivery matrix in various aspects especially animal ischemic models.

Example 8

A functionalized Polymer Designed for Orthopedic Applications

Polymeric biomaterials play an important role in the success of hard tissue engineering. Ideally, polymers used in hard tissue engineering should have good biocompatibility, controlled biodegradability, sufficient mechanical strength, and defined bioactivity. Natural biological polymers, such as collagen, chitin, chitosan, alginate have been adopted in tissue engineering due to their good biocompatibility. However, their biological and mechanical properties are hard to adjust and their mechanical strength is relatively low to be utilized alone in hard tissue regeneration. They may lead to immunorejection and disease transmission. batch variation. Synthetic polymers and their composites have the advantage of good control of batch variation, easy handling, controlled degradation and cost effectiveness. Aliphatic polyesters such as Poly (lactide) (PLA), poly(glycolide) (PGA), PPF and their copolymers are the most widely used polymeric materials for hard tissue engineering. However, most of these polyesters are hydrophobic, biologically inert, and lack of free functional group(s) for further modification by biomolecules. They are hard to modify and lack cell recognition sites, and hence are unlikely to induce cell adhesion and tissue formation. Introduction of functional groups such as hydroxyl and carboxylate groups in polyesters, which can increase polyesters' hydrophilicity and degradability, modulate their mechanical, chemical, and biologic properties, may be a useful way to address these drawbacks. However, both pre-functionalization via polymerization of functionalized monomer and post-polymerization functionalization via modification of non-functionalized polyester approaches ate complicated processes with low yield and may be associated with degradation in intense transformation after polymerization. Also the incorporation of biomolecules such as peptides and growth factors does not allow extreme temperature ranges or aggressive chemical conditions during processing. Thus developing efficient synthesis of functionalizable polyesters with controlled mechanical properties and bioactive groups are highly desirable for tissue engineering.

Figure 40:
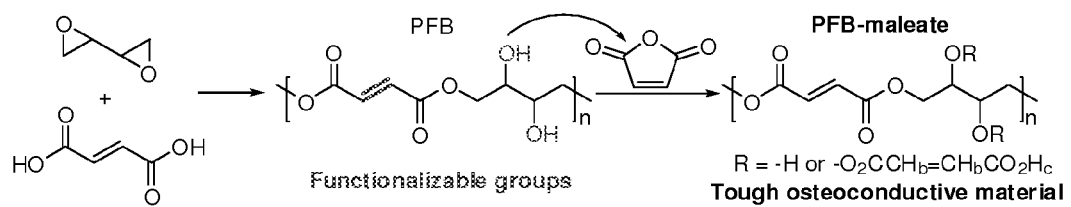
FIG. 40 Design of functionalized material for orthopedic applications.

Here, we chose poly(fumaroyl bioxirane) (PFB) and tailored it for orthopedic applications via introduction of a maleate group (FIG. 40). Our design principles are:

(1) Biodegradability—Aliphatic polyesters have defined biodegradability, the chemical properties of these polymers allow for hydrolytic degradation through de-esterification which can be metabolized and removed from the body via naturally pathways. Polyester bonds construct both the backbone and side chain of PFB-maleate and ensure its good biodegradability.

(2) Osteocompatibility. The extensive hydroxyl and carboxylic groups will provide cell recognition sites for cell adhesion, proliferation and differentiation, and have potentially beneficial effect on hard tissue formation and growth (Kawai T, Ohtsuki C, Kamitakahara M, Hosoya K, Tanihara M, Miyazaki T, et al. In vitro apatite formation on polyamide containing carboxyl groups modified with silanol groups. Journal of Materials Science-Materials in Medicine 2007 June; 18(6):1037-1042 and Miyazaki T, Ohtsuki C, Akioka Y, Tanihara M, Nakao J, Sakaguchi Y, et al. Apatite deposition on polyamide films containing carboxyl group in a biomimetic solution. Journal of Materials Science-Materials in Medicine 2003 July; 14(7):569-574). The free carboxylic acid group can mimic ECM protein to provide a mineralization sites to induce biominerlized tissue regrowth (Phadke A, Zhang C, Hwang Y, Vecchio K, Varghese S. Templated Mineralization of Synthetic Hydrogels for Bone-Like Composite Materials: Role of Matrix Hydrophobicity. Biomacromolecules 2010 August; 11(8): 2060-2068). In addition, material charge plays an important role in cell adhesion, proliferation and differentiation. The carboxylic groups will make the polymer negatively charged and may make it better than neutual charged precursor PFB (Kumar D, Gittings J P, Turner I G, Bowen C R, Hidalgo-Bastida L A, Cartmell S H. Polarization of hydroxyapatite: Influence on osteoblast cell proliferation (vol 6, pg 1549, 2010). Acta Biomater 2010 November; 6(11):4456-4456).

(3) Functionalizability. The free hydroxyl, alkenyl, and carboxylic groups in PFB-maleate enable facile biofunctionalization with biomolecules and diverse crosslinking. The structural flexibility can lead to tunable material properties that will impact material biointerface and also enable facile conjugation with various biomolecules resulting in bioactive polymers. Mechanical properties can also be modulated by photo crosslinking the hydroxyl groups and carboxylic groups or radical crosslinking the double bond it contains. Specific biological functions can be pre-programmed into the polymer by introducing a variety of molecules, including ligands, peptides, proteins, nucleotides by modification of its hydroxyl and carboxylic groups.

(4) Simplicity. PFB-maleate can be produced in two step from commercially available reagents. That makes it easy to scale up and amenable for wide applications.

Thus PFB-maleate should be a very useful biomaterial for hard tissue engineering. As the preliminary study on PFB-maleate, we report its synthesis, characterization, and in vitro osteocompatibility.

Materials and methods

Synthesis: Poly(fumaroyl bioxirane) synthesized as previously described in example 6 was mixed with maleic anhydride and dissolved in anhydrous DMF in a Schelnk flask in a glove box filled with nitrogen. The flask was sealed, transferred out of the glove box, and connected to a Schlenk line. The flask was heated at 80° C. and its contents were stirred under a nitrogen atmosphere for 4.5 hours. The reaction mixture was purified via precipitation in di-$H_2O$ and freeze-dried under a vacuum at ambient temperature to produce PFB-maleate.

Compression testing: Test was conducted on an Instron 5564 mechanical analyzer equipped with a 2 kN load cell according to ASTM standard D695-02a. Three cylinder-shaped samples (Diameter:Height=1:2) were tested and averaged. Test speed was 1 mm/min. The samples were compressed to reach the maximum ability of the loading cell.

In vitro degradation: Cholesterol esterase isolated from bovine pancreas was purchased from Sigma Aldrich Spectrophotometric assays of enzyme activity were conducted using a p-nitrophenol acetate substrate. Solutions were incubated at 37° C. and pH of 7.0 for up to 60 min and read at 410 nm. One unit of CE was defined as the concentration of enzyme required to generate 1 μmol/min of p-nitrophenol from the hydrolysis of p-nitrophenol acetate. Disk-shaped specimens (4 mm in diameter, around 30 mg) was put in 10 ml solution of cholesterol esterase in DPBS (0.4 unit/ml) and incubated at 37° C. with gentle shake using Thermo Scientific Thermal Rocker. 100 μl Concentrated chlosterol esterase DPBS solution (40 unit/ml) was added every three days to keep the concentration of cholesterol esterase. ul stock solution of was added to keep the concentration of Cholesterol esterase.

Cell culture—Osteoblasts were isolated by sequential trypsin-collagenase digestion of calvaria of neonatal (2-3 days old) Sprague-Dawley rats. Briefly Neonatal rat calvariaes were dissected free along the edge. The edges, connective tissues and periosteum were cut away. The calvariaes were placed in a Petri dish with DPBS and cut into 1 mm*1 mm pieces. Then transfer the pieces to a 25 mL tube with DPBS. After being rinsed with DPBS twice 4 mL of digestion solution (Add 1 mL of 0.25% trypsin solution and 3.2 mg of collagenase II to 4 mL of PBS. Make fresh) was added into the tube, digested on a shaker at 37° C. for 30 min. Then add 700 ul FCS to stop disgestion, centrifuge cell population for 5 min at 1000 rpm. Discard the supernatant, resuspend the cell population with 4 ml DMED with 10% FCS, Pipet in a 25 ml culture flask. Repeat the entire procedure four times to obtain population Nos. 1-4. Cells were cultured in a fully humidified incubator(37° C., 5% $CO_2$). The culture medium was changed Id after isolation of osteoblasts. Within approx 5-7 d cells will reach subconfluency and were passaged. Passage 4 osteoblasts were used to do all cell functional tests.

Cell Adhesion—For quantitative evaluation of cell adhesion, osteoblasts were cultured for 1 h, 4 h and 8 h both on PFB-maleate coated 24-well culture plate and uncoated TCPS (n=5), enzymatically (0.25% trypsin-0.1% EDTA—Gibco) detached and counted using a hemocytometer. Cell adhesion rate was expressed as percentage of initial number of seeded cells ($2\times10^4$ cells/ml).

Cell Morphology—1 ml of osteoblasts cell suspension ($2\times10^4$ /ml) was seeded and cultured on PFB-maleate coated and uncoated 24-well plate in a humidified incubator. 1 h, 4 h and 24 h after cell seeding microscopic electro photos were taken and comparative analyzed (Nikon).

Cell Proliferation & Viability—The proliferation of osteoblast on PFB-maleate and TCPS was determined using the MTT assay. Osteoblasts suspension were seeded on 96-well microplate (2000/well, n=8). Firstly remove the medium and replace with 100 μl of MTT solution (5 mg MTT powder in 1 ml DMEM without phenol red, make fresh). Following incubation for 4 h in a fully humidified incubator, MTT was taken up by active cells and reduced in the mitochondria to insoluble purple formazan granules. Subsequently the precipitated formazan was dissolved in 100 μl dimethyl sulfoxide solution (10 g SDS powder in 10 ml 0.01% HCl, make fresh). Then read absorbance at a wave-length of 570 nm by using a microplate spectrophotometer (Bioteck, USA). The analytical assays were performed every other day (1, 3, 5, 7 d).

Total Protein Synthesis—Total protein content was calculated 7, 14, and 21 days after osteoblast culture. Remove the culture medium, rinse the cells with DPBS and add 200 ul cell lysis (0.1% titon-X100+0.01% SDS) to each well. After 15 min incubation on ice, scrape the cells and collect the lysis solution in EP tube. Centrifuge for 15 minutes at 12000 rpm, 4° C., collect the suspend and store at −80° C. for further assay. Pierce 660 nm protein assay Kit (Thermo Scientific) was used to calculate the total protein content. According to the commercial product instructions: add 10 μl of each replicate of standard, unknown sample and the appropriate blank sample into a microplate well; add 150 ul reagent into each well, cover plate and mix on a plate shaker at medium speed for 1 minute; and incubate at room temperature for 5 minutes. The absorbance was then measured at 660 nm (Bioteck, USA) and the total protein content was calculated from the standard curve and expressed as micrograms per milliliter.

Alkaline Phosphatase Activity Assay—Alkaline phosphatase (ALP) activity was assayed by using a commercial kit (Sigma). The kit uses p-nitrophenyl phosphate (pNPP) as a phosphatase substrate which turns yellow when dephosphorylated by ALP. Samples of the same solutions used for calculating total protein content were assayed for measuring ALP activity according to the manufacturer's instructions. Briefly, 100 ul pNPP reagent was mixed with 10ul sample each well, then reacted at room temperature in dark for 30 minutes. This substrate produces a soluble end product that is yellow in color and was spectrophotometrically at 405 nm. ALP activity was measured after 7, 14, and 21 days culture and normalized by total protein concentration and minutes.

Statistical analysis—Statistical analysis was performed using a two-tailed Student's t test with a minimum confidence level of p<0.05 for statistical significance. All values are reported as mean±standard deviation.

Results

Figure 41A:
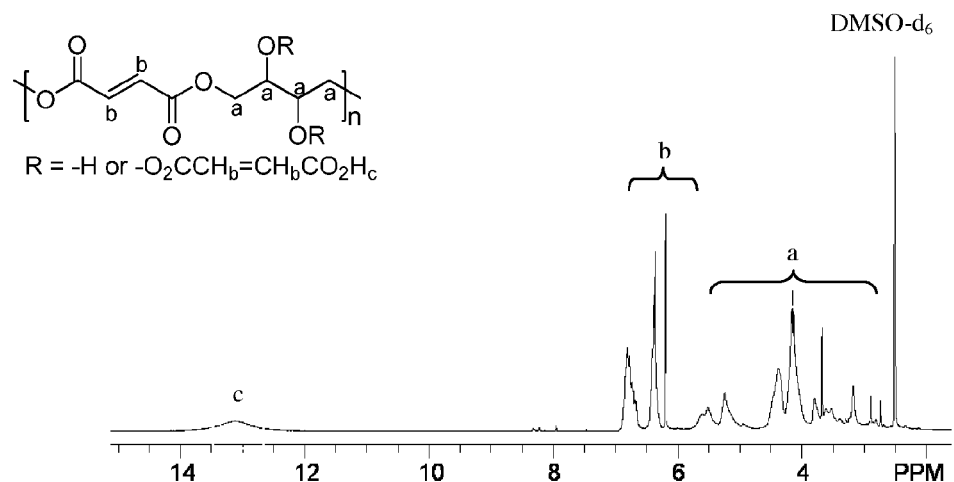
FIGS. 41A and 41B.
Figure 41B:
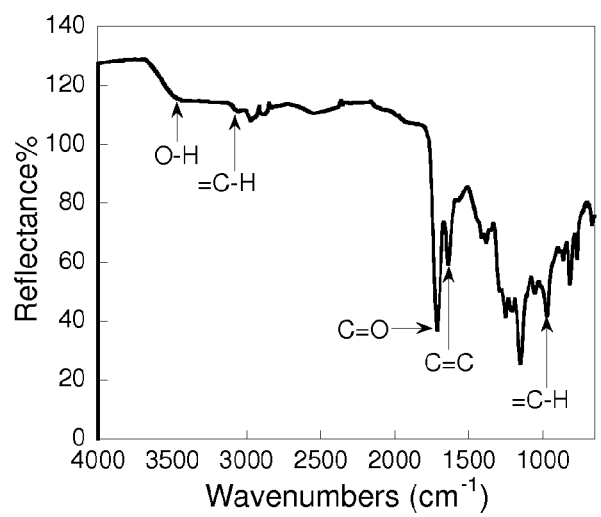

Polymer synthesis and characterization—poly(fumaroyl bioxirane) (PFB) was prepared in nearly quantitative yield as the method described in example 6. Partial esterification of the hydroxyl groups using maleic anhydride produced PFB-maleate with moderate molecular weight (Mn=32.5 kDa) and narrow polydispersity (PDI=1.8). The good solubility of PFB-maleate in normal organic sovlent such as methanol, THF, DMF, DMSO indicated no apparent crosslinking during the whole procedure. NMR spectrum demonstrated the structure of PFB-maleate corroboratively (FIG. 41A). The signal at chemical shift 3.17-5.60 marked 'a' corresponded to the protons of the butane-1,2,3,4-tetraol moiety in the polymer backbone. The signal at chemical shift 6.20-6.84 marked 'b' corresponded to the alkenyl protons of the fumaroyl moiety in the polymer backbone and maleate groups in the side chain. The broad peak at chemical shift around 13.14 marked 'c' corresponded to the protons of free carboxylic acid groups in maleate moiety ($-O_2CCH=CHCO_2H$). Comparison of the relative integrations of the protons in different moieties of PFB-maleate suggested around 26% —OH groups in PFB were converted to maleate groups. FTIR spectrum further confirmed the presence of characteristic functional groups (FIG. 41B). The broad peak at around 3489 $cm^{-1}$ corresponded to O—H bond stretch vibration. The peaks at 3055 and 974 $cm^{-1}$ corresponded to the stretch and bend vibration of C—H bond in alkenyl groups, respectively. The intense peaks at 1715 and 1642 corresponded to the stretch vibration of C=O and C=C groups, respectively. Various physical properties of PFB-maleate were investigated. The glass transition temperature of PFB-maleate was 101.4° C. indicating that it was a hard material at body temperature (37° C.) and might be amenable to load bearing applications for hard tissue engineering. Water contact angle of PFB-maleate was 13.2±1.2°, revealing that it was hydrophilic and might have good cytophilicity. Zeta potential of PFB-maleate in methanol was −27.9±3.4 mV confirming that it was negatively charged as designed.

Figure 42:
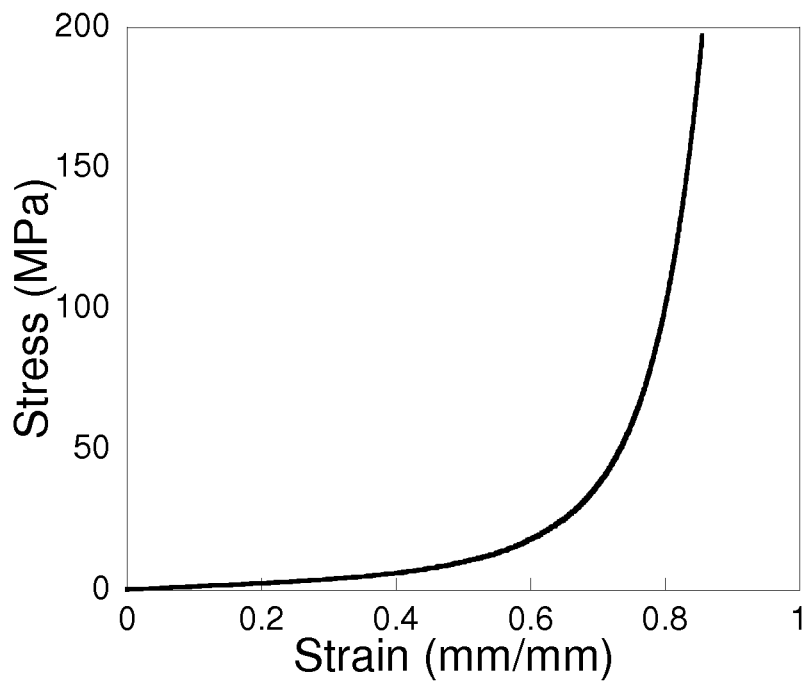
FIG. 42 Representative stress-strain curve (compression) of PFB-maleate. * Load (1800 N) exceeded the load cell capability.

Mechanical properties—The compression test revealed that PFB-maleate was a tough material with interesting strain-dependent moduluses (FIG. 42). The modulus increased with the increase of strain. The stress-strain curve showed a biphasic profile with an inflexion at around 0.70 strain. At the first region it was a relatively soft material with E=8.83±1.54 MPa at the linear portion of strain 0-0.05 and underwent large strain with moderate stress. This region endowed flexibility to PFB-maleate with fracture strain up to 0.86±0.02. The modulus increased dramatically in the second region and reached 1170±340 MPa (more than 130 times higher than initial E) at the linear portion of strain 0.80-0.84. This region endowed toughness to PFB-maleate with fracture stress up to 165.4±29.9 MPa.

In vitro degradation—We expect that the polyester backbone of PFB-maleate can degrade through hydrolysis. Therefore, we investigated the in vitro degradation in the solution of hydrolytic enzyme. Concentrated cholesterol esterase DPBS solution was used to accelerate degradation. PFB-maleate revealed significant mass loss: 48.6±3.0% and 95.6±1.1% mass loss at day 6 and day 12, respectively. It confirmed the good biodegradability of PFB-maleate and indicated the ester groups might be primary degradable group for in vivo applications.

Biocompatibility Test

Figure 43:
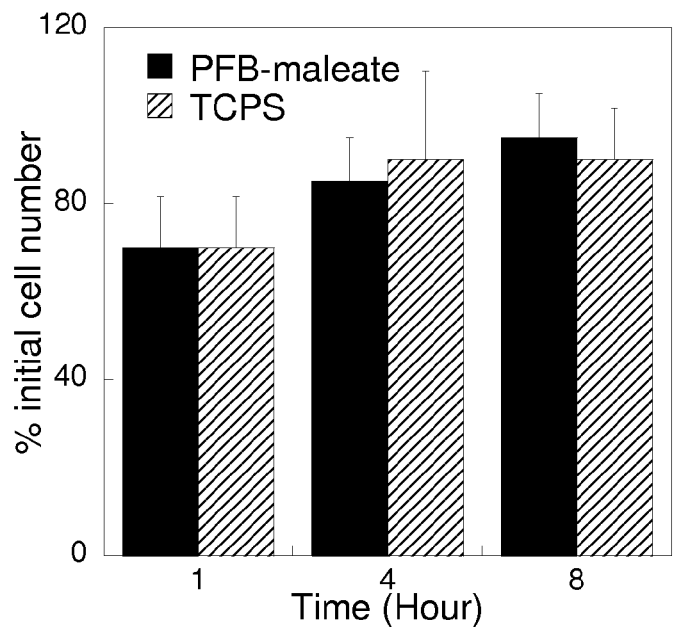
FIG. 43 Cell adhesion rate after 1, 4, 8 h cell seeding (no significant difference between the adhered cell rate on PFB-maleate and that on TCPS at each time point (1 h, 4 h, 8 h) (P>0.05)).

Cell adhesion—There was no significant difference between the adhered cell rate on PFB-maleate and that on TCPS at each time point (1 h, 4 h, 8 h) (P>0.05). Osteoblasts were easy to attach to the polymer coating, the rate of adhered cell number had reached about 70% 1 h after cell seeding. (FIG. 43)

Figure 44:
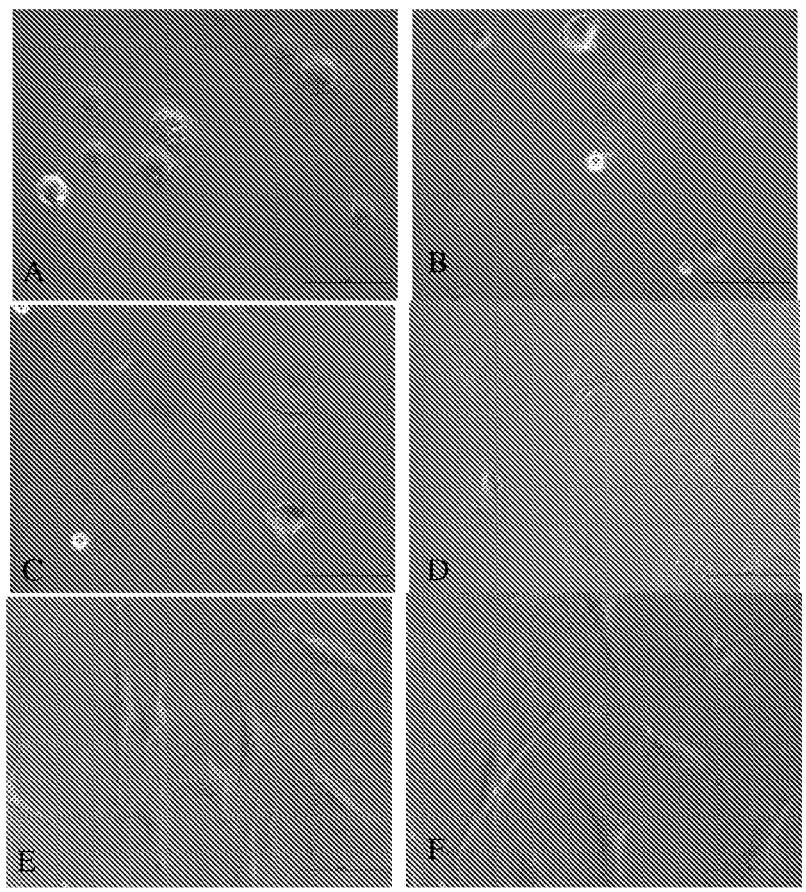
FIG. 44 Cell morphology (A: 1 h after cell seeding on TCPS; B: 1 h after cell seeding on PFB-maleate; C: 4 h after cell seeding on TCPS; D: 4 h after cell seeding on PFB-maleate; E: 24 h after cell seeding on TCPS; F: 24 h after cell seeding on PFB-maleate) (×100).

Cell morphology—1 h after cell seeding, osteoblasts began to adhere to the PFB-maleate, osteoblasts have expanded well 4 h after cell seeding, displayed polygonal shape. Cell size became larger even 2 to 3 times larger than primary size. From the pictures we found at every time point the cell morphology between PFB-maleate and TCPS were similar. 24 h after cell attachment the typical morphology of osteoblasts which is large, polygonal and podite could be seen at all microscopic fields. (FIG. 44)

Figure 45:
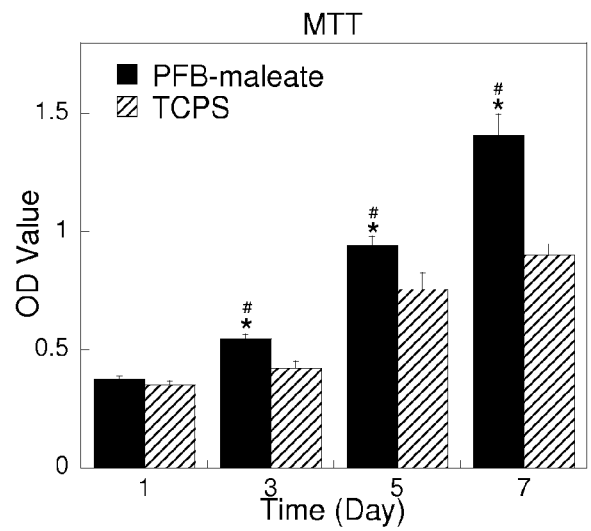
FIG. 45 MTT assay of osteoblasts cultured on PFB-maleate and TCPS.

Cell proliferation & viability—The MTT assay was used to evaluate the cytotoxicity of the PFB-maleate and its influence of cell growth and proliferation. OD values of osteoblasts on both PFB-maleate and TCPS were shown in FIG. 45. It can be seen that the OD value of cells cultured on PFB-M and TCPS increased with the time of culture, which indicates that our polymer has no significant negative effect on the viability of osteoblasts and has a good biocompatibility. The OD value of PFB-maleate is significantly higher than that of TCPS after 3, 5 and 7 days culture (P<0.05). This indicates the percent of viable cells on PFB-maleate is significant higher than on TCPS during culture. There is no significant difference appears at 1 day culture.

Figure 46:
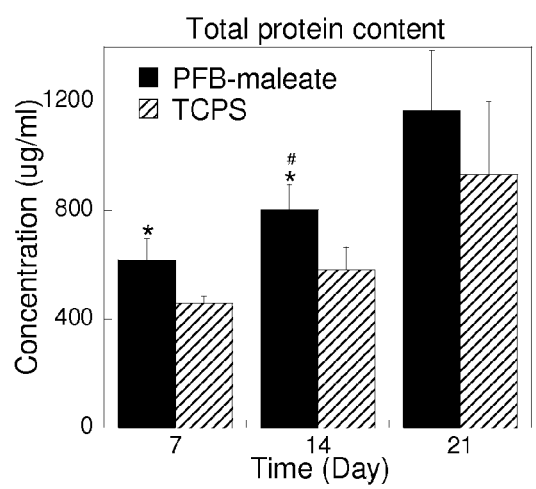
FIG. 46 Total protein content of osteoblasts cultured on on PFB-maleate and TCPS.

Total Protein synthesis—Total protein content was affected by the period of culture (p<0.05) as follows: 7 days<14 days<21 days (FIG. 46). Total protein content was higher (p<0.05) on PFB-maleate than on TCPS and was affected by the period of culture (p<0.05) as follows: 7 days<14 days (FIG. 46). Though the mean protein content was higher on polymer than on TCPS there was no statistical significance at 21 days.

Figure 47:
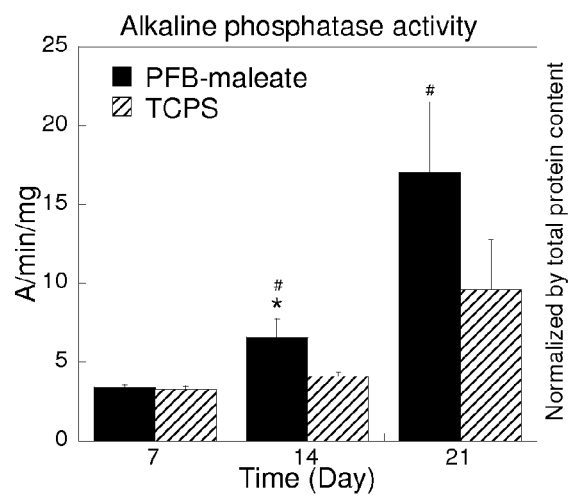
FIG. 47 ALP activity assay of osteoblasts cultured on on PFB-maleate and TCPS

Alkaline phosphatase activity Assay—ALP activity was significantly higher (p<0.05) on PFB-maleate than on TCPS after 14 days culture and was affected by the period of culture (p<0.05) as follows: 7 days<14 days<21 days. Mean ALP activity was higher on PFB-maleate coating than that on TCPS at 21 days however there was no statistical significance. (FIG. 47)

Discussion—We present a good example to functionalize PFB, a functionalizable platform recently developed in our group, for orthopedic applications. The synthetic method is simple and efficient. It takes only two steps to synthesize functionalized PFB-maleate from commercially-available materials under mild conditions. The procedures do not involve any protection and deprotection step, which are required for almost all chemical methods to synthesize similar functionalized polyesters containing free hydroxyl or carboxylic acid groups. Therefore the process is easy to scale up. Catalyst-free esterification using maleic anhydride provides a clean way to introduce maleate group. This reaction does not require the use of cytotoxic additives. The maleic anhydride is the only reagent. Unreacted maleic anhydride can be quenched and washed away by water. This is a significant advantage for biomedical applications. Modulation of the feed ratio of maleic anhydride, reaction temperature and duration may control the extent of esterification.

In terms of bioactivity, the aim of this preliminary in vitro investigation of the biofunctionalable polymer, PFB-maleate, was to study and evaluate the biocompatibility and osteocompatibility of the novel material in hard tissue engineering. Cell adhesion and cell morphology showed PFB-maleate has good biocompatibility, did not appear to differ significantly between PFB-maleate and TCPS that were examined. MIT assay and total protein content proved that osteoblasts proliferated faster on PFB-maleate than on TCPS. ALP activity assay showed PFB-maleate has better osteogenetic ability compare to TCPS.

Osteoblasts are the cells that support the formation, secretion and mineralization of the extracellular bone matrix, providing important parameters in study of the biomaterial/cell interaction. The rat primary culture of osteoblasts is a well-established model to investigate biocompatibility and osteocompatability of biomaterials. Based on these considerations, the present preliminary in vitro study investigated the biological properties of rat osteoblasts cultured on our desired functionalizable polymer PFB-maleate. Cellular interaction with biomaterials is a basic issue considered when evaluating materials. Cell adhesion, which directly influences cell morphology, proliferation, and differentiation, is an important factor for the use of polymeric materials in tissue engineering applications. It may be affected by several factors, such as material chemical components, surface charge and hydrophilicity or hydrophobicity. Hydrophilicity can significantly improved the protein adsorption and has great influence on initial cell adhesion, spreading, and cytoskeletal organization. Thus an optimal hydrophilicity is required to promote cell adhesion and spreading. In this study, cells exhibited a well-spread morphology on PFB-maleate, which is hydrophilic, after 4 h seeding, even just after 1 h seeding osteoblasts began to adhere well on the surface of the polymer and some of them began to spread (FIG. 44). Also surface charge play a big role on cell adhesion and proliferation, both negative and positive charge is better than neutral charge for a material to induce cell adhere and spreading. The hydrophilic PFB-maleate has negative charge while TCPS has positive charge, the osteoblasts adhesion rate and spreading have no significant difference between them.

MTT assay and Total protein concentration measurements showed a similar trend of gradually growing trend of cell population. Osteoblasts on PFB-maleate proliferated much faster than on TCPS, and total protein concentrations were lower on TCPS when compared with PFB-maleate at 7 days and 14 days. As reported, both positive and negative charge on material surface are beneficial for the proliferation of osteoblasts (Kawai T, Ohtsuki C, Kamitakahara M, Hosoya K, Tanihara M, Miyazaki T, et al. In vitro apatite formation on polyamide containing carboxyl groups modified with silanol groups. Journal of Materials Science-Materials in Medicine 2007 June; 18(6):1037-1042). At 14 days, Protein concentrations of cells on PFB-maleate were significantly higher than those on TCPS while at 21 days there was no significant difference between the two groups, the attenuation in the concentration of protein suggests that the cells on PFB-maleate reached confluency state while cells on TCPS were still proliferating. These results indicate that our polymer PFB-maleate are good substrates for osteoblast adhesion and proliferation.

ALP is an indicator of osteoblast cell maturity. As shown in FIG. 47, cells expressed higher ALP activity on PFB-maleate when compared with TCPS after 14 days culture which indicates increased osteoblast maturity and function. Over the period of 21 days, the gradually elevated phenotypic expressions of osteoblast indicated the progression of cell maturity on PFB-maleate. Such observed cell proliferation and ALP expression trends on PFB-maleate are in line with sequential proliferation and differentiation phases of osteoblasts. As reported in the literature, material's mechanical and chemical properties play an important role in cell differentration (Huebsch N, Arany P R, Mao A S, Shvartsman D, Ali O A, Bencherif S A, et al. Harnessing traction-mediated manipulation of the cell/matrix interface to control stem-cell fate. Nature Materials 2010 June; 9(6):518-526 and Nakaoka R, Yamakoshi Y, Isama K, Tsuchiya T. Effects of surface chemistry prepared by self-assembled monolayers on osteoblast behavior. J Biomed Mater Res A 2010 August; 94A(2):524-532). The enhanced maturation of osteoblasts on PFB-maleate might be attributed to the increased calcium concentration due to the COOH- groups, which could potentially activate calcium channels in the osteoblast plasma membrane and regulate the intracellular activities (Miyazaki T, Ohtsuki C, Akioka Y, Tanihara M, Nakao J, Sakaguchi Y, et al. Apatite deposition on polyamide films containing carboxyl group in a biomimetic solution. Journal of Materials Science-Materials in Medicine 2003 July; 14(7):569-574). The bone formation in direct contact with negatively charged ceramic surfaces suggests that the negative charges enhanced the osteobonding ability of the HAp ceramics. Our polymer manifests negative charge due to contained —COOHgroups can improve osteoblast maturation and bone formation as proved in our study. Furthermore the group here can also be changed with other type of groups or peptides which can improve the function we desired.

In conclusion, we developed a novel functionalized polymer, PFB-maleate. The presence of —COOH could enhance the phenotypic expression of the primary rat osteoblast cells. PFB-maleate supported osteoblast adhesion, proliferation, and differentiation in vitro. Calcification of carboxylic acid in PFB-maleate will result in PFB-maleate-Ca and further phosphorylation of PFB-maleate-Ca will produce PFB-maleate-CaP. This chemically binded organic/inorganic composite will be more useful for bone regeneration. The materials based on PFB-maleate will be a promising resource for orthopedic applications. Further, the diverse functional groups of PFB-maleate enable diverse functionalization and consequently its physical, mechanical, biological properties can be modulated in a wide range. For example, its mechanical properties can be adjusted by crosslinking methods and its bioactivity can be modulated by conjuated various biomolecules. We expect it will be a good candidate for a variety of tissue regeneration applications. In this example, we demonstrated that the biodegradable and biofunctionalzed polymer, PFB-maleate, has good biocompatibility and osteocompatability and will be a promising polymeric materials for developing bone substitute materials.

Example 9

A Phosphorated Polyester—an Osteoconductive Material

Bone tissue defects due to trauma, tumor and other diseases is a troublesome challenge for surgeons. Though autologous bone graft transplantation is still the golden standard for bone defect reconstruction, the main problem is that patients need to sacrifice their healthy tissue. Meanwhile allografts are extremely limited in clinic use for high incidence of immune rejection and lack of donor sources. Recently tissue engineering approach has manifested its effective roles on bone tissue regeneration. It provides a potential alternative means to solve the difficult clinical problem. Biomaterials play an important role in the success of bone tissue engineering. Advances in biomaterial research have raised expectations of discovery of clinically useful bench markers. However, functional biomaterial research and functional restoration of damaged bone tissues are still major challenges in medicine. Ossification is the critical step in bone regeneration. The availability of extracellular phosphate is a critical requirement for ossification.

Here, we design a phosphorylated polyester, poly(sebacoyl diglyceride) phosphate (PSeD-P). We expect PSeD-P can recapitulate the essence of phosphorylated glycoproteins critical for bone mineralization and promote bone integration. PSeD-P showed good in vitro osteocompatibility.

Figure 48A:
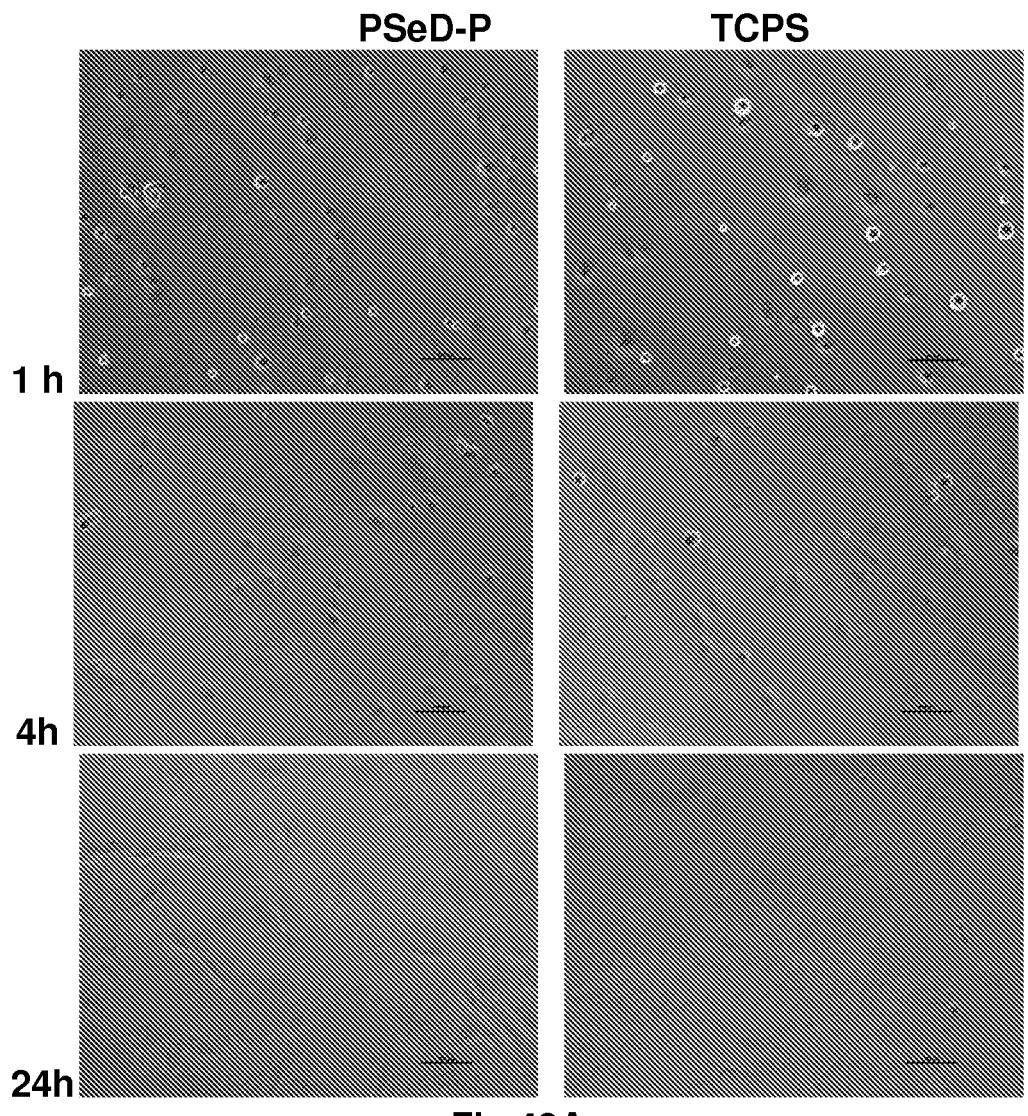
FIGS. 48A and 48B show the results of cell adhesion assays for Example 9.
Figure 48B:
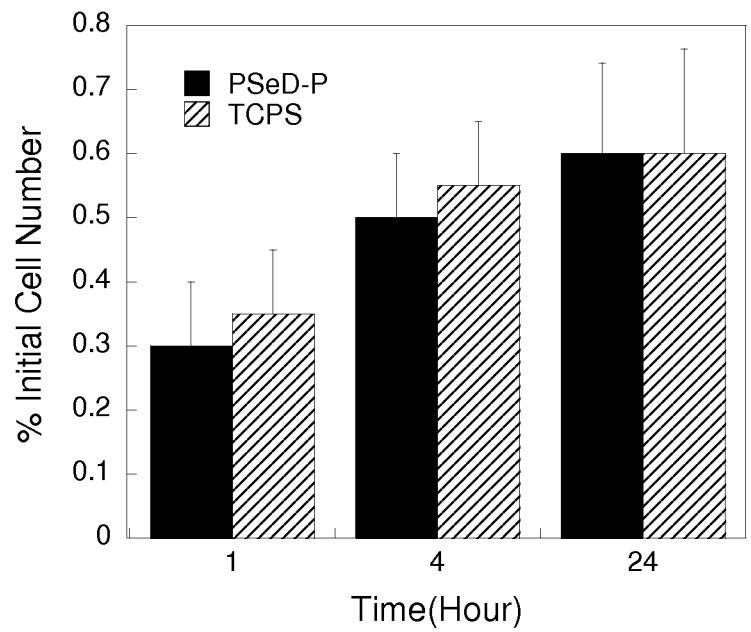
Figure 49:
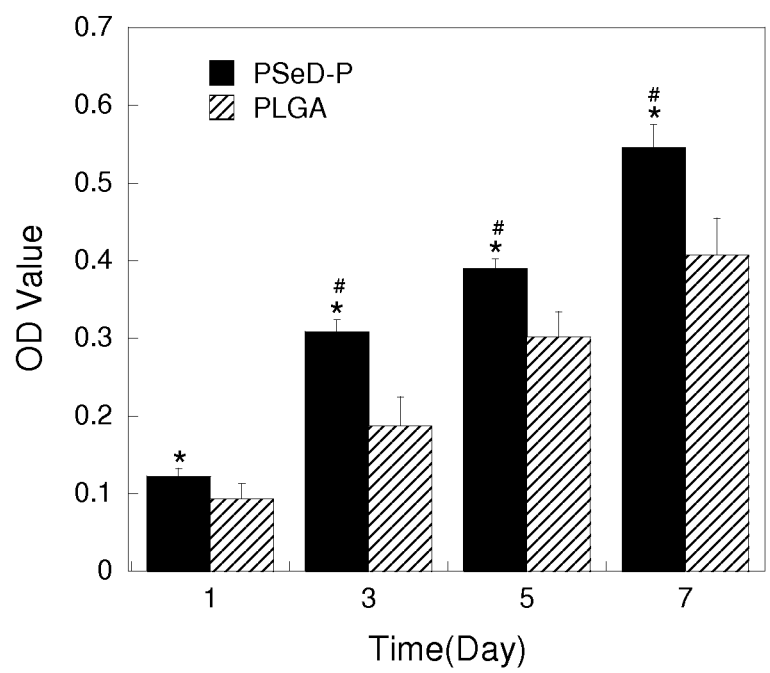
FIG. 49 is a graph showing the results of an MTT Assay for Example 9.
Figure 50:
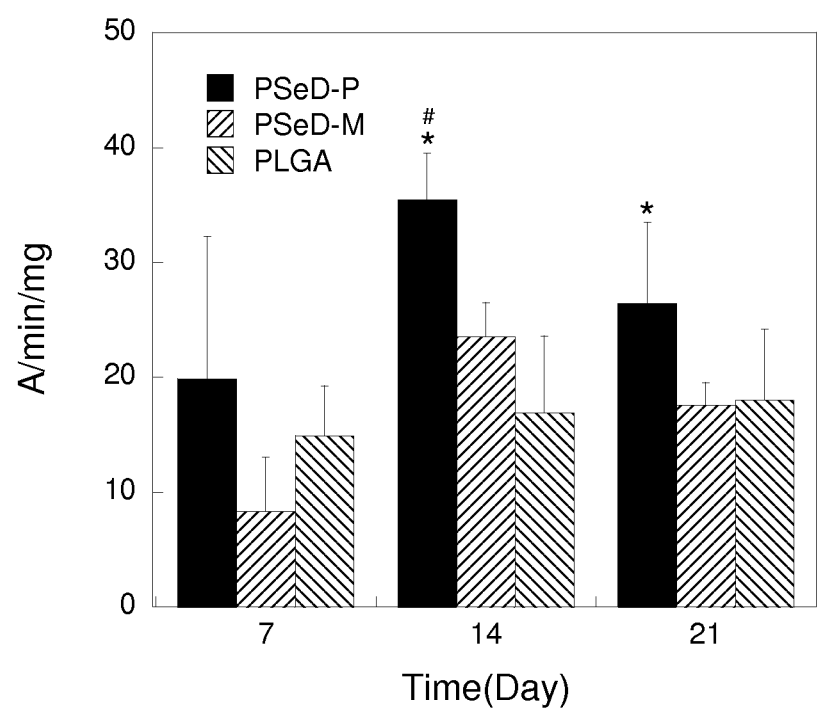
FIG. 50 is a graph demonstrating alkaline phosphatase (ALP) activity assay of osteobleasts for Example 9.

Materials and methods:
Synthesis and characterization. PSeD-P was synthesized and characterized as described in example 6 (compound 2G).
Evaluation of osteocompatibility. We performed adhesion, MTT, and alkaline phosphatase (ALP) activity assays of primary osteoblast cultured on PSeD-P using TCPS and PLGA as controls. The procedures are essentially same as described in example 9.
FIGS. 48A and 50B show the results of cell adhesion assays. FIGS. 48A and 48B indicate that there is no significant difference between PSeD-P and TCPS of the ratio of adhered osteoblasts.
FIG. 49 is a graph showing the results of an MTT Assay. The graph illustrates that the number of metabolically active osteoblasts cultured on PSeD-P significantly increased in another day (#$p<0.05$) and is significantly higher than that on PLGA at all time points. (*$P<0.05$) These indicate that PSeD-P has no significant negative effect on the metabolism of osteoblasts and has a better cytocompatibility than PLGA. PLGA.
Cell metabolic activity. FIG. 50 is a graph demonstrating ALP activity assay of osteobleasts. ALP activity of osteoblasts cultured on PSeD-P was significantly higher than on PSeD-M [poly(sebacoyl diglyceride) maleate synthesized as described in example 1] and PLGA at 14 days culture. (*$P<0.05$); ALP activity of osteoblasts cultured on PSeD-P was affected by the period of culture as follows: 7 d<14 d>21 d (#$p<0.05$)). These results demonstrates superior osteogenic ability of PSeD-P as compared to PLGA and even PSeD-M. It indicates that phosphate group may be a better functionality than carboxylate group to promote osteogenesis.

Example 10

Wound Healing

The purpose of this study is to investigate controlled release of growth factors in a murine wound healing model. The study includes two control groups with mice that receive no treatment (saline) and mice that receive the delivery vehicle only, and two experimental groups (delivery vehicle+EGF; bolus EGF).

Female C57BL/6 mice of 14-16 g body weight are selected. Subjects are anesthetized with 40 mg/kg sodium pentobarbital and two identical full-thickness dorsal wounds are made with a round 6 mm skin biopsy punch in each animal. Wounds are covered by an occlusive dressing. After 12 hours and bleeding has ceased, subjects receive test solutions by sterile pipette and dressing is re-applied to contain solutions in the wound site. Control groups incl: no treatment, receiving 200 μl saline, and delivery vehicle only, and receiving 100 μl delivery matrix in 100 μl saline. Experimental groups each receive 500 ng EGF or FGF-2 delivered either by bolus in 200 μl saline, or by 100 μl delivery matrix in 100 μl saline.

Data are taken at 6 different time points on days 0, 3, 5, 7, 9, and 11 when the wound size is measured and the wounded and surrounding tissue is harvested for immunostaining.

Controlled growth factor release is expected to result in wound healing and increased tissue viability at the site of the wound. It is also likely that controlled release of EGF will lead to less scar or even scarless healing.

The invention claimed is:

1. A polymer composition comprising at least one moiety selected from the following:
   (a) [—OC(O)—CH(NHY)—CH$_2$—C(O)O—CH$_2$—CH(O—R1)—CH$_2$—O—CH$_2$—CH$_2$—O—CH$_2$—CH(O—R2)—CH$_2$—]$_n$,
   (b) [—OC(O)—CH$_2$—CH(NHY)—C(O)O—CH$_2$—CH(O—R1)—CH$_2$—O—CH$_2$—CH$_2$—O—CH$_2$—CH(O—R2)—CH$_2$]$_n$,
   (c) [—OC(O)—CH(NHY)—CH$_2$—CH$_2$—C(O)O—CH2—CH(O—R1)—CH$_2$—O—CH$_2$—CH$_2$—O—CH$_2$—CH(O—R2)—CH$_2$]$_n$, and/or
   (d) [—OC(O)—CH$_2$—CH$_2$—CH(NHY)—C(O)O—CH2—CH(O—R1)—CH$_2$—O—CH$_2$—CH$_2$—O—CH$_2$—CH(O—R2)—CH$_2$—]$_n$,
   wherein Y is —C(O)—CH(NH$_3^+$)—(CH$_2$)$_3$—NH—C(NH$_2$)$_2^+$ or —C(O)—CH(NH$_3^+$)—(CH$_2$)$_4$—(NH$_3$)$^+$, and R1 and R2 are the same or different and are independently selected from the group consisting of hydrogen,

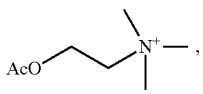

a carboxy-containing group, an α, β unsaturated carboxylic acid, a cinnamic acid containing group, a p-coumaric acid containing group, a ferulic acid containing group, a caffeic acid containing group, an amine-containing group, a quaternary ammonium containing group, maleic acid, a peptide, maleate, succinate, a phosphate-containing group, and a halo-containing group.

2. The composition of claim 1 having a polydispersity index of less than 3.0.

3. The composition of claim 1 having a polydispersity index of less than 2.0.

4. The composition of claim 1 in which one or both of R1 and R2 are charged.

5. The composition of claim 1 in which one or both of R1 and R2 are a phosphate-containing group.

6. The composition of claim 1, attached non-covalently to a calcium phosphate selected from the group consisting of hydroxyapatite, apatite, tricalcium phosphate, octacalcium phosphate, calcium hydrogen phosphate, and calcium dihydrogen phosphate.

7. The composition of claim 1, in which R1 and R2 are selected from the group consisting of Ile-Lys-Val-Ala-Val (IKVAV) (SEQ ID NO: 1), Arg-Gly-Asp (RGD), Arg-Gly-Asp-Ser (RGDS) (SEQ ID NO: 2), Ala-Gly-Asp (AGD), Lys-Gln-Ala-Gly-Asp-Val (KQAGDV) (SEQ ID NO: 3), Val-Ala-Pro-Gly-Val-Gly (VAPGVG) (SEQ ID NO: 4), APGVGV (SEQ ID NO: 5), PGVGVA (SEQ ID NO: 6), VAP, GVGVA (SEQ ID NO: 7), VAPG (SEQ ID NO: 8), VGVAPG (SEQ ID NO: 9), VGVA (SEQ ID NO: 10), VAPGV (SEQ ID NO: 11) and GVAPGV (SEQ ID NO: 12)).

8. The composition of claim 1, complexed with heparin or heparan sulfate.

9. The composition of claim 8, further complexed with a growth factor.

10. The composition of claim 1 in which one or both of R1 and R2 are maleate or phosphate.

11. The composition of claim 1 wherein the at least one polymer is selected from formulae (a) or (b).

12. The composition of claim 11, wherein Y is —C(O)—CH(NH$_3^+$)—(CH$_2$)$_4$—(NH$_3$)$^+$.

13. The composition of claim 11, wherein Y is —C(O)—CH(NH$_3^{30}$)—(CH$_2$)$_3$—NH—C(NH$_2$)$_2^\pm$.

14. The composition of claim 1, wherein Y is —C(O)—CH(NH$_3^+$)—(CH$_2$)$_4$—(NH$_3$)$^+$.

15. The composition of claim 1, wherein Y is —C(O)—CH(NH$_3^+$)—(CH$_2$)$_3$—NH—C(NH$_2$)$_2^\pm$.

16. The composition of claim 1 in which one or both of R1 and R2 are

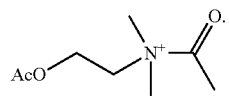

17. The composition of claim 12 in which R1 is hydrogen.
18. The composition of claim 13 in which R1 is hydrogen.
19. The composition of claim 1 wherein the at least one polymer is selected from formulae (c) or (d).
20. The composition of claim 19, wherein Y is —C(O)—CH(NH$_3^+$)—(CH$_2$)$_3$—NH—C(NH$_2$)$_2^\pm$.
21. The composition of claim 20 in which R1 is hydrogen.
22. The composition of claim 19, wherein Y is —C(O)—CH(NH$_3^+$)—(CH$_2$)$_4$—$_{(NH3)}^+$.
23. The composition of claim 22 in which R1 is hydrogen.
24. The composition of claim 19 in which one or both of R1 and R2 is

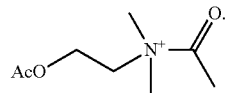

25. The composition of claim 19 in which one or both of R1 and R2 are charged.
26. The composition of claim 25 in which one or both of R1 and R2 are maleate or phosphate.
27. The composition of claim 19 in which one or both of R1 and R2 are a phosphate-containing group.
28. The composition of claim 19, attached non-covalently to a calcium phosphate selected from the group consisting of hydroxyapatite, apatite, tricalcium phoshate, octacalcium phosphate, calcium hydrogen phosphate, and calcium dihydrogen phosphate.
29. The composition of claim 19, in which R1 and R2 are selected from the group consisting of Ile-Lys-Val-Ala-Val (IKVAV) (SEQ ID NO: 1), Arg-Gly-Asp (RGD), Arg-Gly-Asp-Ser (RGDS) (SEQ ID NO: 2), Ala-Gly-Asp (AGD), Lys-Gln-Ala-Gly-Asp-Val (KQAGDV) (SEQ ID NO: 3), Val-Ala-Pro-Gly-Val-Gly (VAPGVG) (SEQ ID NO: 4), APGVGV (SEQ ID NO: 5), PGVGVA (SEQ ID NO: 6), VAP, GVGVA (SEQ ID NO: 7), VAPG (SEQ ID NO: 8), VGVAPG (SEQ ID NO: 9), VGVA (SEQ ID NO: 10), VAPGV (SEQ ID NO: 11) and GVAPGV (SEQ ID NO: 12)).
30. The composition of claim 19, complexed with heparin or heparan sulfate.
31. The composition of claim 30, further complexed with a growth factor.
32. The composition of claim 19 having a polydispersity index of less than 3.0.
33. The composition of claim 19 having a polydispersity index of less than 2.0.
34. The composition of claim 11 in which one or both of R1 and R2 are

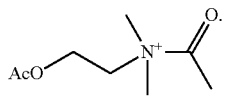

35. The composition of claim 11 in which one or both of R1 and R2 are charged.

36. The composition of claim 35 in which one or both of R1 and R2 are maleate or phosphate.

37. The composition of claim 11 in which one or both of R1 and R2 are a phosphate-containing group.

38. The composition of claim 11, attached non-covalently to a calcium phosphate selected from the group consisting of hydroxyapatite, apatite, tricalcium phosphate, octacalcium phosphate, calcium hydrogen phosphate, and calcium dihydrogen phosphate.

39. The composition of claim 11, in which R1 and R2 are selected from the group consisting of Ile-Lys-Val-Ala-Val (IKVAV) (SEQ ID NO: 1), Arg-Gly-Asp (RGD), Arg-Gly-Asp-Ser (RGDS) (SEQ ID NO: 2), Ala-Gly-Asp (AGD), Lys-Gln-Ala-Gly-Asp-Val (KQAGDV) (SEQ ID NO: 3), Val-Ala-Pro-Gly-Val-Gly (VAPGVG) (SEQ ID NO: 4), APGVGV (SEQ ID NO: 5), PGVGVA (SEQ ID NO: 6), VAP, GVGVA (SEQ ID NO: 7), VAPG (SEQ ID NO: 8), VGVAPG (SEQ ID NO: 9), VGVA (SEQ ID NO: 10), VAPGV (SEQ ID NO: 11) and GVAPGV (SEQ ID NO: 12)).

40. The composition of claim 11, complexed with heparin or heparan sulfate.

41. The composition of claim 40, further complexed with a growth factor.

42. The composition of claim 11 having a polydispersity index of less than 3.0.

43. The composition of claim 11 having a polydispersity index of less than 2.0.

44. The composition of claim 18, further complexed with heparin or heparin sulfate to produce a vehicle.

45. The composition of claim 44, further comprising an active agent complexed with the vehicle.

46. The composition of claim 45, wherein the active agent is a growth factor.

47. The composition of claim 46, wherein the growth factor is one or more of a FGF, an EGF and VEGF.

48. A biological scaffold comprising a polymer composition according to claim 1.

49. A drug delivery vehicle comprising a polymer composition according to claim 1.

50. A biological scaffold comprising a polymer composition according to claim 19.

51. A drug delivery vehicle comprising a polymer composition according to claim 19.

52. A biological scaffold comprising a polymer composition according to claim 11.

53. A drug delivery vehicle comprising a polymer composition according to claim 11.

54. A method of growing cells, comprising culturing cells on the scaffold of claim 48.

55. A method of inducing neurite formation in a neuron comprising contacting a neuron with a composition according to claim 16.

56. A method of growing cells, comprising culturing cells on the scaffold of claim 50.

57. A method of inducing neurite formation in a neuron comprising contacting a neuron with a composition according to claim 24.

58. A method of growing cells, comprising culturing cells on the scaffold of claim 52.

59. A method of inducing neurite formation in a neuron comprising contacting a neuron with a composition according to claim 34.

* * * * *

UNITED STATES PATENT AND TRADEMARK OFFICE
CERTIFICATE OF CORRECTION

PATENT NO.         : 9,023,972 B2                                            Page 1 of 1
APPLICATION NO.    : 13/522996
DATED              : May 5, 2015
INVENTOR(S)        : Chu et al.

It is certified that error appears in the above-identified patent and that said Letters Patent is hereby corrected as shown below:

In the claims

Column 69, Line 9, Claim 1, delete " — $CH_2]_n$," and insert -- — $CH_2$—$]_n$, --

Column 69, Line 12, Claim 1, delete " — $CH_2]_n$," and insert -- — $CH_2$—$]_n$, --

Column 69, Line 57, Claim 7, delete "12))." and insert -- 12). --

Column 70, Lines 1-2, Claim 13, delete "—C(O)—CH($NH_3^{30}$)—($CH_2$)$_3$—NH—C($NH_2$)$_2^{\pm}$." and insert -- —C(O)—CH($NH_3^+$)—($CH_2$)$_3$—NH—C($NH_2$)$_2^+$. --

Column 70, Lines 5-6, Claim 15, delete "—C(O)—CH($NH_3^+$)—($CH_2$)$_3$—NH—C($NH_2$)$_2^{\pm}$." and insert -- —C(O)—CH($NH_3^+$)—($CH_2$)$_3$—NH—C($NH_2$)$_2^+$. --

Column 70, Lines 20-21, Claim 20, delete "—C(O)—CH($NH_3^+$)—($CH_2$)$_3$—NH—C($NH_2$)$_2^{\pm}$." and insert -- —C(O)—CH($NH_3^+$)—($CH_2$)$_3$—NH—C($NH_2$)$_2^+$. --

Column 70, Lines 23-24, Claim 22, delete "—C(O)—CH($NH_3^+$)—($CH_2$)$_4$—$(NH_3)^+$." and insert -- —C(O)—CH($NH_3^+$)—($CH_2$)$_4$—$(NH_3)^+$. --

Column 70, Line 57, Claim 29, delete "12))." and insert -- 12). --

Column 71, Line 28, Claim 39, delete "12))." and insert -- 12). --

Signed and Sealed this
Fifteenth Day of December, 2015

Michelle K. Lee
*Director of the United States Patent and Trademark Office*